(12) United States Patent
Boppart et al.

(10) Patent No.: US 8,115,934 B2
(45) Date of Patent: Feb. 14, 2012

(54) DEVICE AND METHOD FOR IMAGING THE EAR USING OPTICAL COHERENCE TOMOGRAPHY

(75) Inventors: Stephen A. Boppart, Champaign, IL (US); Chuanwu Xi, Ann Arbor, MI (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 444 days.

(21) Appl. No.: 12/040,539

(22) Filed: Feb. 29, 2008

(65) Prior Publication Data

US 2009/0185191 A1 Jul. 23, 2009

Related U.S. Application Data

(60) Provisional application No. 61/022,297, filed on Jan. 18, 2008.

(51) Int. Cl.
*G01B 9/02* (2006.01)
*G01B 11/02* (2006.01)

(52) U.S. Cl. .......................... 356/479; 356/497

(58) Field of Classification Search ................... 356/479, 356/497

See application file for complete search history.

(56) References Cited

U.S. PATENT DOCUMENTS

| | | |
|---|---|---|
| 4,522,811 A | 6/1985 | Eppstein et al. |
| 4,930,516 A | 6/1990 | Alfano et al. |
| 5,095,487 A | 3/1992 | Meyerhofer et al. |
| 5,199,431 A | 4/1993 | Kittrell et al. |
| 5,247,343 A | 9/1993 | Burch |
| 5,280,788 A | 1/1994 | Janes et al. |
| 5,303,710 A | 4/1994 | Bashkansky et al. |
| 5,362,478 A | 11/1994 | Desai et al. |
| 5,439,686 A | 8/1995 | Desai et al. |
| 5,451,785 A | 9/1995 | Faris |
| 5,459,570 A | 10/1995 | Swanson et al. |
| 5,491,524 A | 2/1996 | Hellmuth et al. |
| 5,498,421 A | 3/1996 | Grinstaff et al. |
| 5,505,932 A | 4/1996 | Grinstaff et al. |
| 5,508,021 A | 4/1996 | Grinstaff et al. |
| 5,512,268 A | 4/1996 | Grinstaff et al. |
| 5,560,933 A | 10/1996 | Soon-Shiong et al. |
| 5,635,207 A | 6/1997 | Grinstaff et al. |

(Continued)

FOREIGN PATENT DOCUMENTS

EP 1 154 224 11/2001

(Continued)

OTHER PUBLICATIONS

Xi et al., "High-resolution three-dimensional imaging of biofilm development using optical coherence tomography" Journal of Biomedical Optics, May/Jun. 2006, vol. 11(3), pp. 034001-1-034001-6.*

(Continued)

*Primary Examiner* — Patrick J Connolly
(74) *Attorney, Agent, or Firm* — Sunstein Kann Murphy & Timbers LLP

(57) ABSTRACT

A method of forming an image of tissue. The method includes non-invasively inserting a fiber-based device into a patient's ear canal and acquiring OCT data from ear tissue while the fiber-based device is in the ear canal. The method also includes converting the OCT data into at least one image.

30 Claims, 36 Drawing Sheets

U.S. PATENT DOCUMENTS

| | | |
|---|---|---|
| 5,639,473 A | 6/1997 | Grinstaff et al. |
| 5,648,506 A | 7/1997 | Desai et al. |
| 5,650,156 A | 7/1997 | Grinstaff et al. |
| 5,665,382 A | 9/1997 | Grinstaff et al. |
| 5,665,383 A | 9/1997 | Grinstaff et al. |
| 5,752,518 A | 5/1998 | McGee et al. |
| 5,836,877 A | 11/1998 | Zavislan |
| 5,891,619 A | 4/1999 | Zakim et al. |
| 5,914,806 A | 6/1999 | Gordon, II et al. |
| 5,921,926 A | 7/1999 | Rolland et al. |
| 5,930,026 A | 7/1999 | Jacobson et al. |
| 5,972,493 A | 10/1999 | Iwasaki et al. |
| 5,994,690 A | 11/1999 | Kulkami et al. |
| 5,995,645 A | 11/1999 | Soenksen et al. |
| 6,002,476 A | 12/1999 | Treado |
| 6,002,480 A | 12/1999 | Izatt et al. |
| 6,037,579 A | 3/2000 | Chan et al. |
| 6,068,600 A | 5/2000 | Johnson et al. |
| 6,069,932 A | 5/2000 | Peshkin et al. |
| 6,091,496 A | 7/2000 | Hill |
| 6,108,081 A | 8/2000 | Holtom et al. |
| 6,111,645 A | 8/2000 | Tearney et al. |
| 6,134,003 A | 10/2000 | Teamey et al. |
| 6,151,522 A | 11/2000 | Alfano et al. |
| 6,156,292 A | 12/2000 | Quay |
| 6,159,445 A | 12/2000 | Klaveness et al. |
| 6,167,297 A | 12/2000 | Benaron |
| 6,174,291 B1 | 1/2001 | McMahon et al. |
| 6,208,886 B1 | 3/2001 | Alfano et al. |
| 6,219,137 B1 | 4/2001 | Vo-Dinh |
| 6,231,834 B1 | 5/2001 | Unger et al. |
| 6,246,892 B1 | 6/2001 | Chance |
| 6,246,901 B1 | 6/2001 | Benaron |
| 6,249,271 B1 | 6/2001 | Albert et al. |
| 6,262,706 B1 | 7/2001 | Albert et al. |
| 6,262,833 B1 | 7/2001 | Loxley et al. |
| 6,264,917 B1 | 7/2001 | Klaveness et al. |
| 6,264,918 B1 | 7/2001 | Johnson et al. |
| 6,280,704 B1 | 8/2001 | Schutt et al. |
| 6,300,932 B1 | 10/2001 | Albert |
| 6,307,633 B1 | 10/2001 | Mandella et al. |
| 6,307,634 B2 | 10/2001 | Hitzenberger et al. |
| 6,312,304 B1 | 11/2001 | Duthaler et al. |
| 6,315,981 B1 | 11/2001 | Unger |
| 6,344,272 B1 | 2/2002 | Oldenburg et al. |
| 6,363,163 B1 | 3/2002 | Xu et al. |
| 6,428,811 B1 | 8/2002 | West et al. |
| 6,485,413 B1 | 11/2002 | Boppart et al. |
| 6,514,767 B1 | 2/2003 | Natan |
| 6,529,277 B1 | 3/2003 | Weitekamp |
| 6,530,944 B2 | 3/2003 | West et al. |
| 6,538,805 B1 | 3/2003 | Norwood et al. |
| 6,539,156 B1 | 3/2003 | Dickson et al. |
| 6,560,478 B1 | 5/2003 | Alfano et al. |
| 6,564,087 B1 | 5/2003 | Pitris et al. |
| 6,574,401 B2 | 6/2003 | Neuberger et al. |
| 6,584,335 B1 | 6/2003 | Haar et al. |
| 6,615,063 B1 | 9/2003 | Ntziachristos et al. |
| 6,618,423 B1 | 9/2003 | Dekorsy et al. |
| 6,636,755 B2 | 10/2003 | Toida |
| 6,689,067 B2 | 2/2004 | Sauer et al. |
| 6,690,966 B1 | 2/2004 | Rava et al. |
| 6,795,777 B1 | 9/2004 | Scully et al. |
| 6,825,928 B2 | 11/2004 | Liu et al. |
| 6,839,586 B2 | 1/2005 | Webb |
| 6,922,583 B1 | 7/2005 | Perelman et al. |
| 7,181,266 B2 | 2/2007 | Frangioni et al. |
| 7,198,777 B2 | 4/2007 | Boppart et al. |
| 7,217,410 B2 | 5/2007 | Suslick et al. |
| 7,610,074 B2 | 10/2009 | Boppart et al. |
| 7,725,169 B2 | 5/2010 | Boppart et al. |
| 7,751,057 B2 | 7/2010 | Oldenburg et al. |
| 7,787,129 B2 | 8/2010 | Boppart et al. |
| 2002/0028993 A1 | 3/2002 | Hainfeld |
| 2002/0054912 A1 | 5/2002 | Kim et al. |
| 2002/0087071 A1 | 7/2002 | Schmitz et al. |
| 2002/0168161 A1 | 11/2002 | Price et al. |
| 2003/0045798 A1 | 3/2003 | Hular et al. |
| 2003/0068496 A1 | 4/2003 | Wei et al. |
| 2003/0082104 A1 | 5/2003 | Mertelmeier |
| 2003/0171678 A1 | 9/2003 | Batten et al. |
| 2004/0015062 A1 | 1/2004 | Ntziachristos et al. |
| 2004/0023415 A1 | 2/2004 | Sokolov et al. |
| 2004/0024307 A1 | 2/2004 | Golman et al. |
| 2004/0058458 A1 | 3/2004 | Anker et al. |
| 2004/0181128 A1* | 9/2004 | Masters .................. 600/200 |
| 2004/0186359 A1 | 9/2004 | Beaudoin et al. |
| 2004/0249268 A1 | 12/2004 | Da Silva |
| 2005/0004453 A1 | 1/2005 | Tearney et al. |
| 2005/0036150 A1 | 2/2005 | Izatt et al. |
| 2005/0078363 A1 | 4/2005 | Gugel |
| 2005/0149002 A1 | 7/2005 | Wang et al. |
| 2005/0168735 A1 | 8/2005 | Boppart et al. |
| 2005/0171433 A1 | 8/2005 | Boppart et al. |
| 2006/0039004 A1 | 2/2006 | De Boer et al. |
| 2006/0066848 A1 | 3/2006 | Frankel |
| 2006/0109478 A1 | 5/2006 | Tearney et al. |
| 2006/0192969 A1 | 8/2006 | Marks et al. |
| 2006/0276709 A1* | 12/2006 | Khamene et al. ............ 600/416 |
| 2006/0281068 A1 | 12/2006 | Maier et al. |
| 2006/0285635 A1 | 12/2006 | Boppart et al. |
| 2006/0292839 A1 | 12/2006 | Yi et al. |
| 2007/0127756 A1* | 6/2007 | Slabaugh et al. ............ 381/328 |
| 2007/0203404 A1 | 8/2007 | Zysk et al. |
| 2008/0140341 A1 | 6/2008 | Ralston et al. |
| 2008/0281205 A1 | 11/2008 | Naghavi et al. |
| 2009/0185166 A1 | 7/2009 | Oldenburg et al. |
| 2009/0185191 A1* | 7/2009 | Boppart et al. ............... 356/479 |
| 2009/0221920 A1 | 9/2009 | Boppart et al. |

FOREIGN PATENT DOCUMENTS

| | | |
|---|---|---|
| EP | 1 312 912 | 5/2003 |
| EP | 1 447 043 | 8/2004 |
| EP | 0 963 540 | 3/2006 |
| WO | WO 90/01697 | 2/1990 |
| WO | WO 97/32182 | 9/1997 |
| WO | WO98/30873 | 7/1998 |
| WO | WO 98/38907 | 9/1998 |
| WO | WO99/06794 | 2/1999 |
| WO | WO99/58972 | 11/1999 |
| WO | WO 00/42906 | 7/2000 |
| WO | WO 00/42912 | 7/2000 |
| WO | WO02/41760 | 5/2002 |
| WO | WO 02/088705 | 11/2002 |
| WO | WO03/061454 | 7/2003 |
| WO | WO2005/028663 | 3/2005 |
| WO | WO2006/020302 | 2/2006 |
| WO | WO2006/032009 | 3/2006 |
| WO | WO2006/099191 | 9/2006 |
| WO | WO2006/135628 | 12/2006 |
| WO | WO 2007/027194 | 3/2007 |
| WO | WO 2007/090147 | 9/2007 |
| WO | WO 2008/008774 | 1/2008 |

OTHER PUBLICATIONS

Pitris et al, "High-Resolution Imaging of the Middle Ear With Optical Coherence Tomography" Arch Otolaryngol Head Neck Surgery, vol. 127, Jun. 2001, pp. 637-642.*

Ai et al., "Electrostatic layer-by-layer nanoassembly on biological microtemplates: platelets", Biomacromolecules, 3:560-564, 2002.

Amsden et al., "An examination of factors affecting the size, distribution, and release characteristics of polymer microbeads made using electrostatics", J. Control. Release, 43:183-196, 1997.

Amsden, "The production of uniformly sized polymer microspheres", Pharm. Res., 16:1140-1143, 1999.

Balasubramanian et al., "Extraction and dispersion of large gold nanoparticles in nonpolar solvents", J. Dispers. Sci. Tech. 22:485-89, 2001.

Balasubramanian et al., "Dispersion and stability studies of resorcinarene-encapsulated gold nanoparticles", Langmuir, 18:3676-81, 2002.

Barton et al., "Use of microbubbles as an optical coherence tomography contrast agent", Acad. Radiol, 9, (Suppl 1):552-555, 2002.

Blackwell et al., "New approaches to olefin cross-metathesis", J. Am. Chem. Soc., 122:58-71, 2000.

Boppart et al., "Imaging Developing Neural Morphology Using Optical Coherence Tomography", J. Neuroscience Methods, vol. 70, pp. 65-72, 1996.

Boppart et al., "Investigation of Developing Embryonic Morphology Using Optical Coherence Tomography", Developmental Biology, vol. 177, pp. 54-63, 1996.

Boppart et al., "Noninvasive assessment of the developing Xenopus cardiovascular system using optical coherence tomography", Proc. Natl. Acad. Sci. USA, 94: 4256-4261, 1997.

Boppart et al., "Forward-Imaging Instruments for Optical Coherence Tomography", Optics Letters, vol. 22, No. 21, pp. 1618-1620, 1997.

Boppart et al., "In vivo Cellular Optical Coherence Tomography Imaging", Nature Medicine, vol. 4, No. 7, pp. 861-865, 1998.

Boppart et al., "Intraoperative Assessment of Microsurgery with Three-Dimensional Optical Coherence Tomography", Radiology, vol. 208, pp. 81-86, 1998.

Boppart et al., "Optical Coherence Tomography for Neurosurgical Imaging of Human Intracortical Melanoma", Neurosurgery, vol. 43, No. 4, pp. 834-841, 1998.

Boppart, "Surgical Diagnostics, Guidance, and Intervention Using Optical Coherence Tomography", Ph.D. Thesis, Massachusetts Institute of Technology, Cambridge, MA, 226 pages, 1998.

Boppart et al., "High-Resolution Optical Coherence Tomography-Guided Laser Ablation of Surgical Tissue", J. Surgical Research, 82:275-84, 1999.

Boppart, "Endoscopic Optical Coherence Tomography Imaging of Barrett's Esophagus", M.D. Thesis, Harvard University, 2000.

Bouma et al., "High resolution optical coherence tomographic imaging using a mode-locked $Ti:Al_2O_3$ laser source", Optics Letter, 20:1486-1488, 1995.

Bouma et al., "High-resolution imaging of the human esophagus and stomach in vivo using optical coherence tomography", Gastrointestinal Endoscopy, 51: 467-474, 2000.

Boyer et al., "Photothermal Imaging of Nanometer-Sized Metal Particles Among Scatterers", Science, 297:1160-63, 2002.

Brezinski et al., "Optical Coherence Tomography for Optical Biopsy: Properties and Demonstration of Vascular Pathology", Circulation, vol. 93, pp. 1206-1213, 1996.

Bugaj et al., "Novel fluorescent contrast agents for optical imaging of in vivo tumors based on a receptor-targeted dye-peptide conjugate platform", J. Biomedical Optics, 6:122-33, 2001.

Burns et al., "Tumor-localizing and photosensitizing properties of hematoporphyrin derivative in hamster buccal pouch carcinoma", Oral Surg. Oral Med. Oral Pathol., 61:368-372, 1986.

Cain et al., "Thresholds for Visible Lesions in the Primate Eye Produced by Ultrashort Near-Infrared Laser Pulses", Investigative Ophthalmology & Visual Science, 40:2343-49, 1999.

Cain et al., "Visible Retinal Lesions from Ultrashort Laser Pulses in the Primate Eye", Investigative Ophthalmology & Visual Science, 36:879-888, 1995.

Caruso et al., "Nanoengineering of inorganic and hybrid hollow spheres by colloidal templating", Science, 282:1111-1114, 1998.

Cepak et al., "Preparation and Stability of Template-Synthesized Metal Nanorod Sols in Organic Solvents", J. Phys. Chem. B, 102:9985-90, 1998.

Chen et al., "Noninvasive Imaging of In Vivo Blood Flow Velocity Using Optical Doppler Tomography", Optics Letters, vol. 22, pp. 1119-1121, 1997.

Christiansen et al., "Physical and biochemical characterization of Albunex™, a new ultrasound contrast agent consisting of air-filled albumin microparticles suspended in a solution of human albumin", Biotechnol. Appl. Biochem., 19:307-20, 1994.

Clark et al., "Second harmonic generation properties of fluorescent polymer-encapsulated gold nanoparticles", J. Am. Chem. Soc., 122:10234-35, 2000.

de Boer et al., "Two-Dimensional Birefringence Imaging in Biological Tissue by Polarization-Sensitive Optical Coherence Tomography", Optics Letters, vol. 22, pp. 934-936, 1997.

Decher "Fuzzy Nanoassemblies: Toward Layered Polymeric Multicomposites", Science, 277:1232-1237, 1997.

Desai et al., "Controlled and targeted drug delivery with biocompatible protein shell microspheres", 20th Annual Meeting of Society of Biomaterials, Apr. 4-9, 1994, Boston, MA: Proc. Soc. Biomaterial, 20:112, 1994.

Dick et al., "Computed tomography of experimental liver abscesses using a new liposomal contrast agent", Investigative Radiology, 31:194-203, 1996.

Dowlatshahi et al., "Histologic Evaluation of Rat Mammary Tumor Necrosis By Interstitial Nd:YAG Laser Hyperthermia", Lasers in Surgery and Medicine, 12:159-164, 1992.

Drexler et al., "In vivo Ultrahigh-Resolution Optical Coherence Tomography", Optics Letters, vol. 24, No. 17, pp. 1221-1223, 1999.

El-Sayed "Some interesting properties of metals confined in time and nanometer space of different shapes", Accounts of Chemical Research, 34:257-64, 2001.

Freeman et al., "Self-Assembled Metal Colloid Monolayers: An Approach to SERS Substrates", Science, 267:1629-1632, 1995.

Fu et al., "Visual evidence of acidic environment within degrading poly(lactic-co-glycolic acid) (PLGA) microspheres", Pharmaceutical Research, 17:100-106, 2000.

Fujimoto et al., "Optical biopsy and imaging using optical coherence tomography", Nature Medicine, 1:970-972, 1995.

Gazelle et al., "Nanoparticulate computed tomography contrast agents for blood pool and liver-spleen imaging", Acad. Radiol., 1:373-376, 1994.

Geny et al., "Safety of a new transpulmonary echocontrast agent (Albunex®) in repeated echocardiographic studies in patients", Clin. Cardiol., 20:111-115, 1997.

Gimenez-Conti et al., "The hamster cheek pouch carcinogenesis model", J. Cellular Biochemistry Supplement, 17F:83-90, 1993.

Gram, "Drug absorption and distribution", in Modern Pharmacology with Clinical Applications $5^{th}$ Ed., Craig et al., eds., Little, Brown, & Co., Inc.; Boston, MA, pp. 13-24, 1997.

Grinstaff et al., "Air-filled proteinaceous microbubbles: synthesis of an echo-contrast agent", Proc. Natl. Acad. Sci. USA, 88:7708-7710, 1991.

Grubbs et al., "Ring-Closing Metathesis and Related Processes in Organic Synthesis", Acc. Chem. Res., 28:446-52, 1995.

Haes et al., "A nanoscale optical biosensor: sensitivity and selectivity of an approach based on the localized surface plasmon resonance spectroscopy of triangular silver nanoparticles", J. Am. Chem. Soc., 124:10596-604, 2002.

Handley et al., "Colloidal gold labeling studies related to vascular and endothelial function, hemostasis and receptor-mediated processing of plasma macromolecules", European J. Cell Biology, 43:163-74. 1987.

Handley et al., "Colloidal gold-low density lipoprotein conjugates as membrane receptor probes", Proc. Natl. Acad. Sci. USA, 78:368-71, 1981.

Handley "Methods for Synthesis of Colloidal Gold", Colloidal Gold: Principles, Methods, and Applications, (Academic Press), vol. 1, pp. 13-32, 1989.

Hardikar et al., "Coating of nanosize silver particles with silica", J. Colloid and Interface Science, 221:133-36, 2000.

Harrington et al., "Gene therapy for prostate cancer: current status and future prospects", J. Urology, 166:1220-33, 2001.

Hartl et al., "Ultrahigh-Resolution Optical Coherence Tomography Using Continuum Generation In An Air-Silica Microstructure Optical Fiber", Optics Letters, 26:608-610, 2001.

Hee et al., "Optical coherence tomography of the human retina", Arch. Ophthalmol. 113: 325-332, 1995.

Hiergeist et al., "Application of magnetite ferrofluids for hyperthermia", J. Magnetism and Magnetic Materials, 201:420-22, 1999.

Hirsch et al., "A Whole Blood Immunoassay Using Gold Nanoshells", Analytical Chemistry, 75:2377-2381, 2003.

Huang et al., "Optical Coherence Tomography", Science, 254: 1178-1181, 1991.

Jackson et al., "Silver Nanoshells:Variations in Morphologies and Optical Properties", J. Phys. Chem. B, 105:2743-46, 2001.

Jana et al., "Wet chemical synthesis of high aspect ratio cylindrical gold nanorods", J. Phys. Chem. B, 105:4065-67, 2001.

Jang et al., "Visualization of Coronary Atherosclerotic Plaques in Patients Using Optical Coherence Tomography: Comparison With Intravascular Ultrasound", J. American College of Cardiology, 39:604-609, 2002.

Jensen et al., "Electrodynamics of noble metal nanoparticles and nanoparticle clusters", J. Cluster Science, 10:295-317, 1999.

Jin et al., "Photoinduced conversion of silver nanospheres to nanoprisms", Science, 294:1901-03, 2001.

Jordan et al., "Magnetic fluid hyperthermia (MFH): Cancer treatment with AC magnetic field induced excitation of biocompatible superparamagnetic nanoparticles", Magnetism and Magnetic Materials., 201:413-19, 1999.

Jue et al., "Addition of sulfhydryl groups to *Escherichia coli* ribosomes by protein modification with 2-iminothiolane (methyl 4-mercaptobutyrimidate)", Biochemistry, 17:5399-5406, 1978.

Kempka et al., "Binding, uptake, and transcytosis of ligands for mannose-specific receptors in rat liver: an electron microscopic study", Experimental Cell Research,176, 38-48, 1988.

Keye et al., "Argon Laser Therapy of Endometriosis: A Review of 92 Consecutive Patients" Fertility and Sterility, 47:208-212, 1987.

Kim et al., "Hollow silica spheres of controlled size and porosity by sol-gel processing", J. Am. Ceram. Soc., 74:1987-1992, 1991.

Kim et al., "Photochemical synthesis of gold nanorods" J. Am. Chem. Soc., 124:14316-17, 2002.

Kim et al., "Self-Organization of Large Gold Nanoparticle Arrays", J. Am. Chem. Soc., 123:7955-56, 2001.

Kim et al., "Fabrication of hollow silica aerogel spheres by a droplet generation method and sol-gel processing" J. Vac. Sci., Technol. A., 7:1181-1184, 1989.

Kneipp et al., "Ultrasensitive Chemical Analysis by Raman Spectroscopy", Chem. Rev., 99:2957-75, 1999.

Kolb-Bachofen et al., "Electron microscopic evidence for an asialoglycoprotein receptor on Kupffer cells: localization of lectin-mediated endocytosis", Cell, 29:859-66, 1982.

Kolbeck, "The biomedical applications of protein microspheres", Ph.D. Doctoral Thesis, University of Illinois, Urbana-Champaign, title page and pp. 153, 159-160, 1999.

Korbelik et al., "Photofrin accumulation in malignant and host cell populations of various tumours", British Journal of Cancer, 73:506-513, 1996.

Langer "Drug delivery and targeting", Nature, 392:5-10, 1998.

Larson et al., "Water-Soluble Quantum Dots for Multiphoton Fluorescence Imaging in Vivo", Science, 300:1434-1436, 2003.

Lasic et al., "Liposomes revisited", Science, 267:1275-1276, 1995.

Lee et al., "Delivery of liposomes into cultured KB cells via folate receptor-mediated endocytosis", J. Biological Chemistry, 269:3198-3204, 1994.

Lee et al., "Engineered microsphere contrast agents for optical coherence tomography", Optics Letters, vol. 28, No. 17, pp. 1546-1548, 2003.

Lee et al., "Optical Characterization of Contrast Agents for Optical Coherence Tomography", Proceedings of SPIE, vol. 4967, pp. 129-134, 2003.

Leelarasamee et al., "A method for the preparation of polylactic acid microcapsules of controlled particle size and drug loading", J. Microencapsulation, 5:147-157, 1988.

Leitgeb et al., "Spectral measurement of absorption by spectroscopic frequency-domain optical coherence tomography", Optics Letters, 25:820-22, 2000.

Li et al., "Optical Coherence Tomography: Advanced Technology for the Endoscopic Imaging of Barrett's Esophagus", Endoscopy, vol. 32, pp. 921-930, 2000.

Li et al., "Imaging Needle for Optical Coherence Tomography", Optics Letters, 25:1520-1522, 2000.

Li et al., "On the growth of highly ordered pores in anodized aluminum oxide", Chem. Mater., 10:2470-80, 1998.

Li et al., "Polycrystalline nanopore arrays with hexagonal ordering on aluminum", J. Vac. Sci. Technol. A, 17:1428-31, 1999.

Licha, "Contrast agents for optical imaging", Topics in Current Chemistry, 222:1-29, 2002.

Lin et al., "Measurement of tissue optical properties by the use of oblique-incidence optical fiber reflectometry", Applied Optics, 36:136-43, 1997.

Lin et al., "Intraocular Microsurgery with a Picosecond Nd:YAG Laser", Lasers in Surgery and Medicine, 15:44-53, 1994.

Liu et al., "In vivo measurement of oxygen concentration using sonochemically synthesized microspheres", Biophysical J., 67:896-901, 1994.

Liu et al., "A novel two-step silica-coating process for engineering magnetic nanocomposites", Chem. Mater., 10:3936-40, 1998.

Liz-Marzan et al., "Homogeneous silica coating of vitreophobic colloids", Chem. Commun., 731-32, 1996.

Lvov et al., "Nanoparticle/polyion assembly on microtemplates (lipid tubules and latex spheres)", Colloids and Surfaces B: Biointerfaces, 23:251-256, 2002.

Lvov et al., "Thin film nanofabrication via layer-by-layer adsorption of tubule halloysite, spherical silica, proteins and polycations", Colloids and Surfaces A: Physicohem. Eng. Aspects, 198-200:375-382, 2002.

Marks et al., Nonlinear interferometric vibrational imaging, E-print@arxiv.org/physics/0311071, URL http://www.arxiv.org/abs/physics/0311071, pp. 1-5, 2003.

Marks et al., "Study of an Ultrahigh-Numerical-Aperture Fiber Continuum Generation Source For Optical Coherence Tomography", Optics Letters, 27:2010-2012, 2002.

Marks et al., "Pulse shaping strategies for nonlinear interferometric vibrational imaging optimized for biomolecular imaging", Conference Proceeding: EMBC 2004: 26th Annual International Conference of the Engineering in Medicine and Biology Society (Sep. 1-5, 2004, San Francisco, CA), vol. 2, 7 pages, (accession No. 8255487).

Masuda et al., "Ordered metal nanohole arrays made by a two-step replication of honeycomb structures of anodic alumina", Science, 268:1466-68, 1995.

Mathias et al., "Tumor-selective radiopharmaceutical targeting via receptor-mediated endocytosis of Gallium-67-deferoxamine-folate", J. of Nuclear Medicine, 37:1003-1008, 1996.

McNamara III et al., "Sonoluminescence temperatures during multi-bubble cavitation", Nature, 401:772-775, 1999.

Micali et al., "Separation of Scattering and Absorption Contributions in UV/Visible Spectra of Resonant Systems", Anal. Chem., 73:4958-63, 2001.

Minton et al., "The Laser in Surgery. A 23 Year Perspective.", American Journal of Surgery, 151:725-729, 1986.

Mock et al., "Composite plasmon resonant nanowires", Nano Letters, 2:465-69, 2002.

Mock et al., "Shape effects in plasmon resonance of individual colloidal silver nanoparticles", J. Chem. Phys., 116:6755-59, 2002.

Mohwald, "From Langmuir monolayers to nanocapsules", Colloids and Surfaces A: Physicochem. Eng. Aspects, 171:25-31, 2000.

Morgner et al., "Spectrosopic optical coherence tomography", Optics Letters, 25:111-13, 2000.

Nicewarner-Peña et al., "Submicrometer metallic barcodes", Science, 294:137-41, 2001.

Nielsch et al., "Self-ordering regimes of porous alumina: the 10% porosity rule", Nano Letters 2:677-80, 2002.

Novak et al., "Purification of molecularly bridged metallic nanoparticle arrays by centrifugation and size exclusion chromatography", Anal. Chem., 73:5758-61, 2001.

Oldenburg et al., "Light Scattering From Dipole and Quadrupole Nanoshell Antennas", Appl. Phys. Lett., 75:1063-65, 1999.

Pasternack et al., "Resonance Light Scattering: A New Technique for Studying Chromophore Aggregation", Science, 269:935-39, 1995.

Pathak et al., "Detection of squamous neoplasia by fluorescence imaging comparing porfimer sodium fluorescence to tissue autofluorescence in the hamster cheek-pouch model", American Journal of Surgery, 170:423-426, 1995.

Peters, All about Albumin, in Biochemistry, Genetics, and Medical Applications, (Academic Press, New York), 3 pages, 1996.

Pinkerton et al., "Aerosolized fluorescent microspheres detected in the lung using confocal scanning laser microscopy", Microscopy Research and Technique, 26:437-443, 1993.

Pitris et al., "High-resolution imaging of gynecologic neoplasms using optical coherence tomography", Obstetrics & Gynecology, 93: 135-139, 1999.

Pitris et al., "Feasibility of optical coherence tomography for high-resolution imaging of human gastrointestinal tract malignancies", J. Gastroenterol., 35: 87-92, 2000.
Pollack et al., "Circumferential Argon Laser Photocoagulation for Prevention of Retinal Detachment", Eye, vol. 8, pp. 419-422, 1994.
Profio et al., "Transport of light in tissue in photodynamic therapy", Photochemistry and Photobiology, 46: 591-599, 1987.
Prudhomme et al., "Interstitial Diode Laser Hyperthermia in the Treatment of Subcutaneous Tumor", Lasers in Surgery and Medicine, 19:445-450, 1996.
Puliafito et al., "Imaging of macular disease with optical coherence tomography", Ophthalmology, 102: 217-229, 1995.
Puliafito et al., "Optical Coherence Tomography of Ocular Diseases", Slack Inc, Thorofare, N.J., pp. 3-34, 369-374, 1995.
Pusztay et al., "Encagement of Gold Nanoclusters in Crosslinked Resorcinarene Shells", Supramolecular Chemistry, 14:291-94, 2002.
Quaroni et al., "Preparation of Polymer-Coated Functionalized Silver Nanoparticles", J. Am. Chem. Soc., 121:10642-43, 1999.
Russell-Jones, "Use of vitamin $B_{12}$ conjugates to deliver protein drugs by the oral route", Critical Reviews in Therapuetic Drug Carrier Systems, vol. 15, No. 6, pp. 557-586, 1998.
Sadtler et al., "Spherical ensembles of gold nanoparticles on silica: electrostatic and size effects", Chem. Commun., 1604-05, 2002.
Sansdrap et al., "Influence of manufacturing parameters on the size characteristics and the release profiles of nifedipine from poly(DL-lactide-co-glycolide) microspheres", International Journal of Pharmaceutics, 98:157-164, 1993.
Schaefer et al., "Real-Time Digital Signal Processing-Based Optical Coherence Tomography and Doppler Optical Coherence Tomography", IEEE Transactions on Biomedical Engineering, vol. 51, No. 1, pp. 186-190, 2004.
Schaefer "Real-Time, Digital Signal Processing-Based Optical Coherence Tomography and Optical Doppler Tomography", Master Thesis, University of Illinois at Urbana-Champaign, 2001.
Schmitt et al., "Measurement of Optical Properties of Biological Tissues by Low-Coherence Reflectometry", Applied Optics., vol. 32, pp. 6032-6042, 1993.
Schmitt et al., "Subsurface Imaging of Living Skin with Optical Coherence Microscopy", Dermatology, vol. 191, pp. 93-98, 1995.
Schmitt et al., "Optical-coherence tomography of a dense tissue: statistics of attenuation and backscattering", Phys. Med. Biol., 39: 1705-1720, 1994.
Sergeev et al., "In vivo endoscopic OCT imaging of precancer and cancer states of human mucosa", Optics Express, 1: 432-440, 1997.
Sevick-Muraca et al., "Fluorescence-enhanced, near infrared diagnostic imaging with contrast agents", Current Opinion in Chemical Biology, Op. Chem. Biol., 6:642-50, 2002.
Shiga et al., "Preparation of Poly(D,L-lactide) and Copoly(lactide-glycolide) Microspheres of Uniform Size", J. Pharm. Pharmacol., 48:891-895, 1996.
Shipway et al., "Nanoparticle arrays on surfaces for electronic, optical, and sensor applications", ChemPhysChem., 1:18-52, 2000.
Sivak Jr. et al., "High-resolution endoscopic imaging of the GI tract using optical coherence tomography", Gastrointestinal Endoscopy, 51:474-479, 2000.
Slaga et al., "An animal model for oral cancer", J. National Cancer Institute Monographs, 13:55-60, 1992.
Sokolov et al., "Real-Time Vital Optical Imaging of Precancer Using Anti-Epidermal Growth Factor Receptor Antibodies Conjugated to Gold Nanoparticles", Cancer Research, 63:1999-2004, 2003.
Sönnichsen et al., "Drastic reduction of plasmon damping in gold nanorods", Physical Review Letters, vol. 88, No. 7:077402-1 to 077402-4, 2002.
Sönnichsen et al., "Spectroscopy of Single Metallic Nanoparticles Using Total Internal Reflection Microscopy", Appl. Phys. Lett., 77:2949-51, 2000.
Stavens et al., "Encapsulation of Neutral Gold Nanoclusters by Resorcinarenes", Langmuir, 15:8337-39, 1999.
Su et al., "Tumor characterization with dynamic contrast-enhanced MRI using MR contrast agents of various molecular weights", Magnetic Resonance in Medicine, 39:259-269, 1998.
Suslick et al., "Protein Microencapsulation of Nonaqueous Liquids", J. Am. Chem. Soc., 112:7807-7809, 1990.

Suslick et al., "Versatile sonochemical reaction vessels" in Experimental Organometallic Chemistry: A Practicum in Synthesis and Characterization, (A. Wayda, Darensburg MY, eds. ACS Symposium Series, Washington, D.C.), pp. 195-197, 1987.
Suslick, "Sonochemistry", Science, 247: 1439-1445, 1990.
Tanaka et al., "Direct visualization of colloidal gold-bound molecules and a cell-surface receptor by ultrahigh-resolution scanning electron microscopy", J. Microscopy, 161:455-61, 1991.
Tearney et al., "Optical Biopsy in Human Gastrointestinal Tissue Using Optical Coherence Tomography", American Journal of Gastroenterlogy, vol. 92, pp. 1800-1804, 1997.
Tearney et al., "Optical Biopsy in Human Urologic Tissue Using Optical Coherence Tomography", J. Urology, vol. 157, pp. 1915-1919 (reprinted as 11 pages), 1997.
Tearney et al., "Catheter-based optical imaging of a human coronary artery", Circulation, 94: 3013, 1996.
Tearney et al., "High-Speed Phase- and Group-Delay Scanning with a Grating-Based Phase Control Delay Line", Optics Letters, vol. 22, No. 23 :1811-1813, 1997.
Tearney et al., "In vivo endoscopic optical biopsy with optical coherence tomography", Science, 276: 2037-2039, 1997.
Tearney et al., "Rapid acquisition of in vivo biological images by use of optical coherence tomography", Optics Letters, 21: 1408-1410, 1996.
Tearney et al., "Scanning single-mode fiber optic catheter-endoscope for optical coherence tomography", Optics Letters, 21: pp. 543-545, 1996.
Templeton et al., "Monolayer-protected cluster molecules", Acc. Chem. Res., 33:27-36, 2000.
Timmerman et al., "Resorcinarenes" Tetrahedron, 52:2663-704, 1996.
Tkachenko et al., "Multifunctional Gold Nanoparticle-Peptide Complexes for Nuclear Targeting", J. Am. Chem. Soc., 125:4700-4701, 2003.
Toth et al., "Retinal effects of ultrashort laser pulses in the rabbit eye", Investigative Ophthalmology & Visual Science, 36:1910-17, 1995.
Toublan et al., "Magnetically-inducible optical contrast agents for optical coherence tomography", presented at the Optical Society of America Biomedical Topical Meeting, Miami, FL, Apr. 7-10, 2002.
Tripp et al., "Self-assembly of cobalt nanoparticle rings", J. Am. Chem. Soc., 124:7914-15, 2002.
Turkevich et al., "A Study of the Nucleation and Growth Processes in the Synthesis of Colloidal Gold", Faraday Soc., 11:55-75, 1951.
Tuting, "The immunology of cutaneous DNA immunization", Current Opinion in Molecular Therapeutics, vol. 1, No. 2, pp. 216-225, 1999.
Ung et al., "Controlled method for silica coating of silver colloids. Influence of coating on the rate of chemical reactions", Langmuir, 14:3740-48, 1998.
van der Laan et al., "In vitro activity of novel antifolates against human squamous carcinoma cell lines of the head and neck with inherent resistance to methotrexate", Int. J. Cancer, 51:909-914, 1992.
Van Der Smissen et al., "Ligand-induced clustering of asialoglycoprotein receptors on rat hepatocytes at 4° C.", European J. of Cell Biology, 60:122-30, 1993.
Van Der Smissen et al., "Quantitative analysis of clustering on biological membranes: methodology and application to ligand-induced asialoglycoprotein receptor redistribution on rat hepatocytes", European J. of Cell Biology, 69:45-54, 1996.
van der Zande et al., "Colloidal dispersions of gold rods: synthesis and optical properties", Langmuir, 16:451-58, 2000.
Violante et al., "Improved detectability of VX2 carcinoma in the rabbit liver with contrast enhancement in computed tomography", Radiology, 134:237-239, 1980.
Vitkin et al., "Optical and thermal characterization of natural (*Sepia officinalis*) melanin", Photochemistry and Photobiology, 59:455-62, 1994.
Vo-Dinh, "Surface-Enhanced Raman Spectroscopy Using Metallic Nanostructures", Trends in Analytical Chemistry, 17:557-82, 1998.
Wang et al., "Semiconductor quantum dot-labeled microsphere bioconjugates prepared by stepwise self-assembly", Nano Lett., 2:857-861, 2002.

Wang et al., "Use of a Laser Beam with an Oblique Angle of Incidence to Measure the Reduced Scattering Coefficient of a Turbid Medium", Applied Optics, 34:2362-2366, 1995.
Webb et al., "Sonochemically produced fluorocarbon microspheres: a new class of magnetic resonance imaging agent", J. Magnetic Resonance Imaging, 6:675-683, 1996.
Wei et al., "Resorcinarene-encapsulated nanoparticles: building blocks for self-assembled nanostructures", J. Inclusion Phenomenal Macrocyclic Chemistry, 41, 83-86, 2001.
Wei et al., "Synthesis and Characterization of Resorcinarene-Encapsulated Nanoparticles", Mater. Res. Soc., Symp. Proc. Ser., 581:59-63, 1999.
Wei et al., "Tunable Surface-Enhanced Raman Scattering from Large Gold Nanoparticle Arrays", ChemPhysChem., 2:743-45, 2001.
Wong et al., "Sonochemically produced hemoglobin microbubbles", Mat. Res. Soc. Symp. Proc., 372:89-94, 1995.
Xu et al., "Electromagnetic Contributions to Single-Molecule Sensitivity in Surface-Enhanced Raman Scattering", Physical Review E, 62:4318-24, 2000.
Yazdanfar et al., "High Resolution Imaging of in vivo Cardiac Dynamics Using Color Doppler Optical Coherence Tomography", Optics Express, vol. 1, pp. 424-431, 1997.
Yguerabide et al., "Light-scattering submicroscopic particles as highly fluorescent analogs and their use as tracer labels in clinical and biological applications", Analytical Biochemistry, 262:137-56, 1998.
Yu et al., "Gold nanorods: electrochemical synthesis and optical properties", J. Phys. Chem. B, 101:6661-64, 1997.
Zaheer et al., "In vivo near-infrared fluorescence imaging of osteoblastic activity", Nature Biotechnology, 19:1148-54, 2001.
Marks et al., "Interferometric differentiation between resonant Coherent Anti-Stokes Raman Scattering and nonresonant four-wave-mixing processes", arXiv:physics/0403007, pp. 1-8, 2004.
Vinegoni et al., "Nonlinear optical contrast enhancement for optical coherence tomography", Optics Express, vol. 12, No. 2, p. 331-341, 2004.
Kee et al., "Simple approach to one-laser, broadband coherent anti-Stokes Raman scattering microscopy", Optics Letters, vol. 29, No. 23, p. 2701-2703, 2004.
Kano et al., "Vibrationally resonant imaging of a single living cell by supercontinuum-based multiplex coherent anti-Stokes Raman scattering microspectroscopy", Optics Express, vol. 13, Issue 4, pp. 1322-1327, 2005.
Gao et al., "Formulation, Characterization, and Sensing Applications of Transparent Poly(vinyl alcohol)-Polyelectrolyte Blends", Chem. Mater., 10, pp. 2481-2489, 1998.
Marks et al., Molecular Species Sensitive Optical Coherence Tomography Using Coherent Anti-Stokes Raman Scattering Spectroscopy, Coherence Domain Optical Methods and Optical Coherence Tomography in Biomedicine VII, Proceedings of SPIE, vol. 4956, pp. 9-13, 2003.
Bredfeldt et al., "Non-linear interferometric vibrational imaging", Conference on Lasers and Electro-optics, CLEO '03, pp. 309-311, 2003.
Vinegoni et al., "Nonlinear optical contrast enhancement for optical coherence tomography", http://www.arxiv.org/abs/physics/0312114, 13 pages (2003).
Zumbusch et al., "Three-dimensional vibrational imaging by coherent anti-Stokes Raman scattering", Phys. Rev. Lett., 82(20), pp. 4142-4145, 1999.
Cheng et al., "An epi-detected coherent anti-Stokes Raman scattering (E-CARS) microscope with high spectral resolution and high sensitivity", J. Phys. Chem, 105(7), pp. 1277-1280, 2001.
Hashimoto et al., "Molecular vibration imaging in the fingerprint region by use of coherent anti-Stokes Raman scattering microscopy with a collinear configuration", Opt. Lett., 25(24), pp. 1768-1770, 2000.
Volkmer et al., "Vibrational imaging with high sensitivity via epidected coherent anti-Stokes Raman scattering microscopy", Phys. Rev. Lett., 87(2):023901-1-4, 2001.
Schmitt et al., "Optical-coherence tomography of a dense tissue: statistics of attenuation and backscattering", Phys. Med. Biol., vol. 39, pp. 1705-1720, (1994).
Tearney et al., "In vivo endoscopic optical biopsy with optical coherence tomography", Science, vol. 276, pp. 2037-2039, (1997).
Fantini et al., "Assessment of the size, position, and optical properties of breast tumors in vivo by noninvasive optical methods", Applied Optics, vol. 37, pp. 1982-1989, 1998.
Faber et al., "Quantitative measurement of attenuation coefficients of weakly scattering media using optical coherence tomography", Optics Express, 12(19), pp. 4353-4365, 2004.
Fujimoto et al., "Optical Coherence Tomography: An Emerging Technology for Biomedical Imaging and Optical Biopsy", Neoplasia, 2(1-2), pp. 9-25, 2000.
Zysk et al., "Computational methods for analysis of human breast tumor tissue in optical coherence tomography images", Journal of Biomedical Optics, 11(5), 054015-1-054015-7, 2006.
Levitz et al., "Determination of optical scattering properties of highly-scattering media in optical coherence tomography images", Optics Express, 12(2), pp. 249-259, 2004.
Morgner et al., "Spectroscopic optical coherence tomography", Optics Letters, 25(2), pp. 111-113, 2000.
Gossage et al., "Texture analysis of optical coherence tomography images: feasibility for tissue classification", Journal of Biomedical Optics, 8(3), pp. 570-575, 2003.
Zvyagin et al., "Refractive index tomography of turbid media by bifocal optical coherence refractometry", Optics Express, 11(25), pp. 3503-3517, 2003.
Gottschalk, "Ein Meβverfahren zur Bestimmung der optischen Parameter biologisher Gewebe in vitro", Dissertation 93 HA 8984, Universitat Fridericiana Karlsruhe, 1993.
Bolin, F.P. et al., "Refractive index of some mammalian tissues using a fiber optic cladding method", Applied Optics, 28, pp. 2297-2303, 1989.
Tearney et al., "Determination of the refractive index of highly scattering human tissue by optical coherence tomography", Optics Letters, 20(21), pp. 2258-2260, 1995.
Zysk et al., "Needle-based refractive index measurement using low-coherence interferometry", Optics Letters, 32, pp. 385-387, 2007.
Zysk et al., "Refractive index of carcinogen-induced rat mammary tumours", Phys. Med. Biol., 51, pp. 2165-2177, 2006.
Li et al., "Measurement method of the refractive index of biotissue by total internal reflection", Applied Optics, 35, pp. 1793-1795, 1996.
Knuttel et al., "Spatially confined and temporally resolved refractive index and scattering evaluation in human skin performed with optical coherence tomography", Journal of Biomedical Optics, 5, pp. 83-92, 2000.
Boppart et al., "Optical coherence tomography: feasibility for basic research and image-guided surgery of breast cancer", Breast Cancer Research and Treatment, vol. 84, pp. 85-97, 2004.
Liberman et al., "Palpable breast masses: Is there a role for percutaneous image-guided core biopsy?", American Journal of Roentgenology, vol. 175, pp. 779-787, 2000.
Bolivar et al., "Stereotaxic core needle aspiration biopsy with multiple passes in nonpalpable breast lesions", Acta Radiologica, vol. 39, pp. 389-394, 1998.
Acheson et al., "Histologic correlation of image-guided core biopsy with excisional biopsy of nonpalpable breast lesions", Archives of Surgery, vol. 132, pp. 815-821, 1997.
Pijnappel et al., "The diagnostic accuracy of core biopsy in palpable and non-palpable breast lesions", European Journal of Radiology, vol. 24, pp. 120-123, 1997.
Durduran et al., "Bulk optical properties of healthy female breast tissue", Physics in Medicine and Biology, vol. 47, pp. 2847-2861, 2002.
International Search Report dated Feb. 15, 2007 for International Application No. PCT/US2006/006618, 5 pages.
Marks et al., "Interferometric differentiation between resonant coherent anti-Stokes Raman scattering and nonresonant four-wave-mixing processes", Applied Physics Letters, vol. 85, No. 23, pp. 5787-5789, 2004.
Marks et al., "Nonlinear Interferometric Vibrational Imaging", Physical Review Letters, vol. 92, No. 12, pp. 123905-1-123905-4, 2004.
Boppart et al., "Contrast Enhancement Methods for Optical Coherence Tomography", Biophotonics/Optical Interconnects and VLSI Photonics/WBM Microactivities, 2004 Digest of the Leos Summer Topical Meetings, San Diego, CA, pp. 14-15, 2004.
Marks et al., "Pulse Shaping Strategies for Nonlinear Interferometric Vibrational Imaging Optimized for Biomolecular Imaging", Proceedings of the 26$^{th}$ Annual International Conference of the IEEE EMBS, San Francisco, CA, pp. 5300-5303, 2004.
Bredfeldt et al., "Nonlinear interferometric vibrational imaging of molecular species", Proc. of SPIE, vol. 5321, pp. 149-156, 2004.
Easy Core Biopsy System, Product Brochure, Boston Scientific, 5 pages, 2004.
Yodh et al., "Spectroscopy and Imaging with Diffusing Light," Physics Today, pp. 34-40, 1995.
Roggan et al., in "Laser Induced Interstitial Thermotherapy", Muller, Ed., pp. 39-40,43, 1995.
Ohmi et al., "In Vitro Simultaneous Measurement of Refractive Index and Thickness of Biological Tissue by the Low Coherence Interferometry", IEEE Transactions on Biomedical Engineering, vol. 47, No. 9, pp. 1266-1270, 2000.
Luo et al., "Optical Biopsy of Lymph Node Morphology using Optical Coherence Tomography", Technology in Cancer Research & Treatment, vol. 4, No. 5, pp. 539-547, 2005.
Dehghani et al., "The effects of internal refractive index variation in near-infrared optical tomography: a finite element modelling approach", Physics in Medicine and Biology, 48, pp. 2713-2727, 2003.
Schmitt et al., "Turbulent nature of refractive-index variations in biological tissue", Optics Letters, vol. 21, No. 16, pp. 1310-1312, 1996.
Zysk et al., "Projected index computed tomography", Optics Letters, vol. 28, No. 9, pp. 701-703, 2003.
Easy Core Biopsy System, Product Brochure, Boston Scientific, 4 pages, 2004.
Evans et al., "Coherent anti-Stokes Raman scattering spectral interferometry: determination of the real and imaginary components of nonlinear susceptibility chi(3) for vibrational microscopy", Optics Letters, vol. 29, No. 24, pp. 2923-2925, 2004.
Yoon et al., "Dependence of line shapes in femtosecond broadband stimulated Raman spectroscopy on pump-probe timed delay", J Chem Phys., 122(2), p. 024505, 2005, 20 pages.
Kolomoitsev et al., "New problems of femtosecond time-domain CARS of large molecules", SPIE vol. 1402, pp. 31-43, 1990.
Mehendale et al, "Towards an anthrax detector using the femtosecond adaptive spectroscopic technique for coherent anti-Stokes Raman Spectroscopy: coherent anti-Stokes Raman spectroscopy signal from dipicolinic acid in bacterial spores", Journal of Modern Optics, vol. 51, pp. 2645-2653, 2004.
Invitation to pay additional fees and partial search report dated Apr. 4, 2008 for PCT application No. PCT/US2007/061364.
Huang, D. et al., "Optical Coherence Tomography", Science, 254, 5035, pp. 1178-1181, (1991).
Fercher, A.F. et al., "Optical Coherence Tomography—principles and applications", Institute of Physics Publishing, Reports on Progress in Physics, 66, pp. 239-303, (2003).
Boppart, S.A. et al., "Optical probes and techniques for molecular contrast enhancement in coherence imaging", J. Biomedical Optics, 10(4), pp. 041208-1 thru 041208-14, (2005).
Oldenburg, A.L. et al., "Imaging magnetically labeled cells with magnetomotive optical coherence tomography", Optics Letters, 30, 7, pp. 747-749, (2005).
Oldenburg, A.L. et al., "Selective OCT imaging of cells using magnetically-modulated optical contrast agents", in Proceedings of the Conference on Lasers and Electro-Optics, pp. 405-4-6, (2003).
Kopelman, R. et al., "Multifunctional nanoparticle platforms for in vivo MRI enhancement and photodynamic therapy of a rat brain cancer", J. Magnetism and Magnetic Materials, 293, pp. 404-410, (2005).
Romanus, E. et al., "Magnetic nanoparticle relaxation measurement as a novel tool for in vivo diagnostics", J. Magnetism and Magnetic Materials, 252, pp. 387-389, (2002).
Oldenburg, A.L. et al., "Magnetomotive contrast for in vivo optical coherence tomography", Optics Express, 13, 17, pp. 6597-6614, (2005).

Oh, J. et al., "Detection of magnetic nanoparticles in tissue using magneto-motive ultrasound", Nanotechnology, 17, pp. 4183-4190, (2006).
Joo, C. et al., "Spectral-domain optical coherence phase microscopy for quantitative phase-contrast imaging", Optics Letters, 30, 16, pp. 2131-2133, (2005).
Choma, M.A. et al., "Spectral-domain phase microscopy", Optics Letters, 30, 10, pp. 1162-1164, (2005).
Choma, M.A. et al., "Doppler flow imaging of cytoplasmic streaming using spectral domain phase microscopy", J. Biomedical Optics 11(2), pp. 024014-1 thru 024014-8, (2006).
Sticker, M. et al., "En face imaging of single cell layers by differential phase-contrast optical coherence microscopy", Optics Letters, 27, 13, pp. 1126-1128, (2002).
Sarunic, M.V. et al., "Full-field swept-source phase microscopy", Optics Letters, 31, 10, pp. 1462-1464, (2006).
De la Torre-Ibarra, M.H. et al., "Double-shot depth-resolved displacement field measurement using phase-contrast spectral optical coherence tomography", Optics Express, 14, 21, pp. 9643-9656, (2006).
Vakoc, B.J. et al., "Phase-resolved optical frequency domain imaging", Optics Express, 13, 14, pp. 5483-5493, (2005).
Pedersen, C.J. et al., "Phase-referenced Doppler optical coherence tomography in scattering media", Optics Letters, 30, 16, pp. 2125-2127, (2005).
Ren, H. et al., "Imaging and quantifying transverse flow velocity with the Doppler bandwidth in a phase-resolved functional optical coherence tomography", Optics Letters, 27, 6, pp. 409-411, (2002).
Zhao, Y. et al., "Doppler standard deviation imaging for clinical monitoring of in vivo human skin blood flow", Optics Letters, 25, 18, pp. 1358-1360, (2000).
Ren, H. et al., "Phase-resolved functional optical coherence tomography: simultaneous imaging of in situ tissue structure, blood flow velocity, standard deviation, birefringence, and Stokes vectors in human skin", Optics Letters, 27, 19, pp. 1702-1704, (2002).
Ding, Z. et al., "Real-time phase-resolved optical coherence tomography and optical Doppler tomography", Optics Express, 10, 5, pp. 236-244, (2002).
White, B.R. et al., "In vivo dynamic human retinal blood flow imaging using ultra-high-speed spectral domain optical Doppler tomography", Optics Express, 11, 25, pp. 3490-3496, (2003).
Ren, H. et al., "Real-time in vivo blood-flow imaging by moving-scatterer-sensitive spectral-domain optical Doppler tomography", Optics Letters, 31, 7, pp. 927-929, (2006).
Fang-Yen, C. et al., "Noncontact measurement of nerve displacement during action potential with a dual-beam low-coherence interferometer", Optics Letters, 29, 17, pp. 2028-2030, (2004).
Choma, M.A. et al., "Sensitivity advantage of swept source and Fourier domain optical coherence tomography", Optics Express, vol. 11, No. 18, pp. 2183-2189, (2003).
Leitgeb, R. et al., "Performance of fourier domain vs. time domain optical coherence tomography", Optics Express, 11, 8, pp. 889-894, (2003).
Leitgeb, R.A. et al., "Ultrahigh resolution Fourier domain optical coherence tomography", Optics Express, 12, 10, pp. 2156-2165, (2004).
De Boer, J.F. et al., "Improved signal-to-noise ratio in spectral-domain compared with time-domain optical coherence tomography", Optics Letters, 28, 21, pp. 2067-2069, (2003).
Ralston, T.S. et al., "Phase Stability Technique for Inverse Scattering in Optical Coherence Tomography", International Symposium on Biomedical Imaging, pp. 578-581, (2006).
Yang, C. "Molecular contrast optical coherence tomography: A review", Photochemistry and Photobiology 81, pp. 215-237, (2005).
Kim, J. et al., "Hemoglobin contrast in magnetomotive optical Doppler tomography", Optics Letters, 31, 6, pp. 778-780, (2006).
Oh, J. et al., "Magneto-motive detection of tissue-based macrophages by differential phase optical coherence tomography", Lasers in Surgery and Medicine, 39, pp. 266-272, (2007).
Crecea, V. et al., "Phase-resolved spectral-domain magnetomotive optical coherence tomography", Proc. of SPIE, 6429, pp. 64291X-1 thru 64291X-10, (2007).

Oldenburg, A.L. et al., "Magnetic contrast agents for optical coherence tomography", Proc. of SPIE, 5316, pp. 91-92, (2004).
Oldenburg, A.L. et al., "High-resolution in vivo nanoparticle imaigng using magnetomotive optical coherence tomography", Proc. of SPIE, 6097, pp. 609702-1 thru 609702-11, (2006).
Schmitt, J.M. "OCT elastography: imaging microscopic deformation and strain of tissue", Optics Express, 3, 6, pp. 199-211, (1998).
Gleich, B. et al., "Tomographic imaging using the nonlinear response of magnetic particles", Nature, 435, pp. 1214-1217, (2005).
Anker, J.N. et al., "Magnetically modulated optical nanoprobes", Applied Physics Letters, 82, 7, pp. 1102-1104, (2003).
Harisinghani, M.G. et al., "Noninvasive Detection of Clinically Occult Lymph-Node Metastases in Prostate Cancer", New England J. of Medicine, 348, 25, pp. 2491-2499, (2003).
Arbab, A.S. et al., "In vivo trafficking and targeted delivery of magnetically labeled stem cells", Human Gene Therapy, 15, pp. 351-360, (2004).
Alexiou, C. et al., "Locoregional cancer treatment with magnetic drug targeting", Cancer Research, 60, pp. 6641-6648, (2000).
Winter, P.M. et al., "Molecular imaging of angiogenesis in early-stage atherosclerosis with integrin-targeted nanoparticles", Circulation, 108, pp. 2270-2274, (2003).
Mornet S. et al.,"Magnetic nanoparticle design for medical diagnosis and therapy", J. of Materials Chemistry, 14, pp. 2161-2175, (2004).
Kim, J. et al., "Imaging nanoparticle flow using magneto-motive optical Doppler tomography", Nanotechnology, 18, 035504, pp. 1-6, (2007).
Oldenburg, A.L. et al., "Spectral-Domain Magnetomotive OCT Imaging of Magnetic Nanoparticle Biodistribution", Proc. of SPIE, vol. 6847, pp. 684719-1 thru 684719-8, (2008).
Oldenburg, A.L. et al., "Phase-resolved magnetomotive OCT for imaging nanomolar concentrations of magnetic nanoparticles in tissues", Optics Express, 16(15), pp. 11525-11539, (2008).
Oldenburg, A.L. et al., "Optical micro-scale mapping of dynamic biomechanical tissue properties", Optics Express, 16(15), pp. 11052-11065, (2008).
Oldenburg, A.L. et al., "Spectroscopic optical coherence tomography and microscopy", IEEE Journal of Selected Topics in Quantum Electronics, special issue on Biophotonics, 13(6), pp. 1629-1640, (2007).
Zysk, A.M. et al., "Optical coherence tomography: A review of clinical development from bench to bedside", Special section on optical diagnostic imaging from bench to bedside, Journal of Biomedical Optics, 12(5), pp. 051403-1 thru 051403-20, (2007).
Tan, W. et al., "Optical coherence tomography of cell dynamics in three-dimensional tissue models", Optics Express, 14(16), pp. 7159-7171, (2006).
Oldenburg, A.L., "Plasmon-resonant gold nanorods as law backscattering albedo contrast agents for optical coherence tomography", Optics Express, vol. 14, No. 15, pp. 6724-6736, (2006).
Senin, A.A. et al., "Molecular dissociation observed with an atomic wavepacket and parametric four-wave mixing", Chemical Physics Letters, 381, pp. 53-59, (2003).
Oldenburg, A.L. et al., "Fast Fourier-domain delay line for in vivo optical coherence tomography with a polygonal scanner", Applied Optics, 42(22), pp. 4606-4611, (2003).
Marks, D.L. et al., "Autofocus algorithm for dispersion correction in optical coherence tomography", Applied Optics, 42(16), pp. 3038-3046, (2003).
Marks, D.L. et al., "Digital algorithm for dispersion correction in optical coherence tomography for homogeneous and stratified media", Applied Optics, vol. 42, No. 2, pp. 204-217, (2003).
Oldenburg, A.L. et al., "Vibrational wave packets in the $B^1\Pi_u$ and $D1\Sigma u+$ states of $Cs_2$: Determination of improved $Cs_2+(X)$ and $Cs_2(B)$ spectroscopic constants", Journal of Chemical Physics, 113(24), pp. 11009-11018, (2000).
Oldenburg, A.L. et al., "Optically pinpointing magnetic nanoparticles within biological tissue", Optics & Photonics News, 17(12), p. 24, (2006).
Nguyen, F.T. et al., "Magnetic protein microspheres as dynamic contrast agents for magnetomotive optical coherence tomography", Proc. of SPIE, 6867, pp. 68670F-1 thru 68670F-11, (2008).
Oldenburg, A.L. et al., "Plasmon-resonant gold nanorods provide spectroscopic OCT contrast in excised human breast tumors", Proc. of SPIE, 6867, pp. 68670E-1 thru 68670E-10, (2008).
Oldenburg, A.L. et al., "Spectral-domain magnetomotive OCT imaging of magnetic nanoparticle biodistribution", Proc. of SPIE, 6847, pp. 684719-1 thru 684719-11, (2008).
Liang, X. et al., "Modeling and measurement of tissue elastic moduli using optical coherence elastography", Proc. of SPIE, 6858, pp. 685803-1 thru 685803-8, (2008).
Oldenburg, A.L. et al., "Backscattering albedo contrast in OCT using plasmon-resonant gold nanorods", Proc.of SPIE, 6429, pp. 64291Z-1 thru 6429Z-8, (2007).
Oldenburg, A.L. et al., "Characterization of plasmon-resonant gold nanorods as near-infrared optical contrast agents investigated using a double-integrating sphere system", Proc. of SPIE, 5703, pp. 50-60, (2005).
Oldenburg, A.L. et al., "Magnetic contrast agents for optical coherence tomography." Proc. SPIE, 5316, pp. 91-98, (2004).
Oldenburg, A.L. et al., "Optical manipulation of silicon microparticles in biological environments", Proc. SPIE, 4962, pp. 249-255, (2003).
Oldenburg, A.L., "Wavepacket dynamics and time-domain spectroscopy in atomic rubidium", Quantum Electronics and Laser Science Conference 1999, Technical Digest, Thursday Morning, pp. 176-177, (1999).
Swanson, E.A. et al., "In vivo retinal imaging by optical coherence tomography", Optics Letters, 18, 21, pp. 1864-1866, (1993).
American Academy of Pediatrics, Clinical Practice Guideline, "Otitis Media with Effusion", Pediatrics, 113, 5, pp. 1412-1429, (2004).
Pitris, C. et al., "High-resolution imaging of the middle ear with optical coherence tomography: A feasibility study," Arch Otolaryngol Head Neck Surg., 127, pp. 637-642, (2001).
Hall-Stoodley, L. et al., "Direct detection of bacterial biofilms on the middle-ear mucosa of children with chronic otitis media," JAMA, 296, 2, pp. 202-211, (2006).
Xi, C. et al., "High-resolution three-dimensional imaging of biofilm development using optical coherence tomography," J. Biomed. Opt., 11(3), pp. 034001-1 thru 034001-6, (2006).
Leitgeb, R. et al., "Performance of Fourier domain vs. time domain optical coherence tomography," Optics Express, 11, 8, 889-894, (2003).
Ralston, T.S. et al., "Interferometric synthetic aperture microscopy", Nature Physics, 3, pp. 129-134, (2007).
Ralston, T.S. et al., "Inverse Scattering for Optical Coherence Tomography", J. Opt. Soc. Am. A, 23, 5, pp. 1027-1037, (2006).
Sitter, D.N. et al., "Three-dimensional Imaging: a Space invariant Model for Space Variant Systems", Applied Optics, 29, 26, pp. 3789-3794, (1990).
Choma, M.A. et al., "Sensitivity advantage of swept source and Fourier domain optical coherence tomography", Optics Express, 11, 18, pp. 2183-2189, (2003).
Ralston, T.S. et al., "Phase Stability Technique for Inverse Scattering in Optical Coherence Tomography", Biomedical Imaging: Nano to Macro, $3^{rd}$ IEEE International Symposium on Biomedical Imaging, pp. 578-581, (2006).
Costerton, J.W. et al., "Bacterial biofilms: a common cause of persistent infections", Science, 284, pp. 1318-1322, (1999).
Donlan, R.M., "Biofilms and device-associated infections", Emerging Infectious Diseases, 7, 2, pp. 277-281, (2001).
Donlan, R.M. "Biofilms: microbial life on surfaces", Emerging Infectious Diseases, 8, 9, pp. 881-890, (2002).
Fux, C.A. et al., "Survival strategies of infectious biofilms", Trends in Microbiology, 13, 1, pp. 34-40, (2005).
Takata, G.S. et al., "Evidence Assessment of the Accuracy of Methods of Diagnosing Middle Ear Effusion in Children With Otitis Media With Effusion", Pediatrics, 112, 6, pp. 1379-1387, (2003).
Reed, W.A. et al., "Gradient-index fiber-optic microprobes for minimally invasive in vivo low-coherence interferometry," Optics Letters, 27, 20, pp. 1794-1796, (2002).

Vinegoni, C. et al., "Integrated structural and functional optical imaging combining spectral-domain optical coherence and multiphoton microscopy", Applied Physics Letters, 88, pp. 053901-1 thru 053901-3, (2006).

Crecea, V., "Phase-resolved spectral-domain magnetomotive optical coherence tomography for microscopic analysis of biomechanical properties", Preliminary Examination, pp. 1-15, (2007).

Xu, C. et al., "Near-infrared dyes as contrast-enhancing agents for spectroscopic optical coherence tomography", Optics Letters, vol. 29, No. 14, pp. 1657-1649, (2004).

Nguyen, F.T. et al., "Portable Real-Time Optical Coherence Tomography System for Intraoperative Imaging and Staging of Breast Cancer", Proc. Of SPIE, vol. 6430, pp. 64300H-1 thru 64300H1-10, (2007).

Zysk, A.M. et al., "Needle-probe system for the measurement of tissue refractive index", Proc. Of SPIE, vol. 6430, pp. 64300O-1-64300O-8, (2007).

Pasquesi, J.J. et al., "Detection of ultrastructural changes in genetically-altered and exercised skeletal muscle using PS-OCT", Proc. Of SPIE, vol. 6079, pp. 607926-1-607926-7, (2006).

Xu, C. et al., "Spectroscopic spectral-domain optical coherence microscopy", Optics Letters, vol. 31, No. 8, pp. 1079-1081, (2006).

Jones, G.W. et al., "High-spectral-resolution coherent anti-stokes raman scattering with interferometrically detected broadband chirped pulses", Optics Letters, vol. 31, No. 10, pp. 1543-1545, (2006).

Boppart, S.A., "Advances in contrast enhancement for optical coherence tomography", Proceedings of the 28$^{th}$ IEEE EMBS Annual International Conference New York City, USA, pp. 121-124, Aug. 30-Sep. 3, 2006.

Marks, D.L. et al., "High numerical aperture full-field optical coherence tomography with space-invariant resolution without scanning the focus", Proc. Of SPIE, vol. 6429, pp. 64291R1-64291R-9, (2007).

Luo, W. et al., "Three-dimensional optical coherence tomography of the embryonic murine cardiovascular system", Journal of Biomedical Optics, vol. 11(2), pp. 021014-1-021014-8, (2006).

Marks, D.L. et al., "Inverse scattering for frequency-scanned full-field optical coherence tomography", Journal of the Optical Society of America A, vol. 24, No. 4, pp. 1034-1041, (2007).

Ralston, T.S. et al., "Inverse scattering for high-resolution interferometric microscopy", Optics Letters, vol. 31, No. 24, pp. 3585-3587, (2006).

Ralston, T.S. et al., "Demonstration of inverse scattering in optical coherence tomography", Proc. Of SPIE, vol. 6079, pp. 60791T-1-60791T-9, (2006).

Marks, D.L. et al., "Inverse scattering for rotationally scanned optical coherence tomography", J. Opt. Soc. Am. A, vol. 23, No. 10, pp. 2433-2439, (2006).

Zysk, A.M. et al., "Needle-based reflection refractometry of scattering samples using coherence-gated detection", Optics Express, vol. 15, No. 8, pp. 4787-4794, (2007).

Pasquesi, J.J. et al., "In vivo detection of exercise-induced ultrastructural changes in genetically-altered murine skeletal muscle using polarization-sensitive optical coherence tomography", Optics Express, vol. 14, No. 4, pp. 1547-1556, (2006).

Ko, H.J. et al., "Optical coherence elastography of engineered and developing tissue", Tissue Engineering, vol. 12, No. 1, pp. 63-73, (2006).

Zhu, C. et al., "Use of a multiseparation fiber optic probe for the optical diagnosis of breast cancer", Journal of Biomedical Optics, vol. 10(2), p. 024032-1-024032-13, (2005).

Bigio, I.J. et al., "Diagnosis of breast cancer using elastic-scattering spectroscopy: preliminary clinical results", Journal of Biomedical Optics, vol. 5, No. 2, pp. 221-228, (2000).

Bitar, R.A. et al., "Biochemical analysis of human breast tissues using Fourier-transform Raman spectroscopy", Journal of Biomedical Optics, vol. 11(5), p. 054001-1-054001-8, (2006).

Demos, S.G. et al., "Investigation of near-infrared autofluorescence imaging for the detection of breast cancer", IEEE Journal of Selected Topics in Quantum Electronics, vol. 11, No. 4, pp. 791-798, (2005).

Demos, S.G. et al., "Advances in optical spectroscopy and imaging of breast lesions", Journal of Mammary Gland Biology and Neoplasia, vol. 11, pp. 165-181, (2006).

Fournier, L.S. et al., "In-vivo NIR autofluorescence imaging of rat mammary tumors", Optics Express, vol. 14, No. 15, pp. 6713-6723, (2006).

Frank, C.J. et al., "Characterization of human breast biopsy specimens with near-IR Raman-spectroscopy", Analytical Chemistry, vol. 66, No. 3, pp. 319-326, (1994).

Gupta, P.K. et al., "Breast cancer diagnosis using $N_2$ laser excited autofluorescence spectroscopy", Lasers in Surgery and Medicine, vol. 21, pp. 417-422, (1997).

Haka, A.S. et al., "Identifying microcalcifications in benign and malignant breast lesions by probing differences in their chemical composition using Raman spectroscopy", Cancer Research, vol. 62, pp. 5375-5380, (2002).

Haka, A.S. et al., "Diagnosing breast cancer by using Raman spectroscopy", Proceedings of the National Academy of Sciences of the United States of America, vol. 102, No. 35, pp. 12371-12376, (2005).

Haka, A.S. et al., "In vivo margin assessment during partial mastectomy breast surgery using Raman spectroscopy", Cancer Research, vol. 66, pp. 3317-3322, (2006).

Iftimia, N.V. et al., "A portable, low coherence interferometry based instrument for fine needle aspiration biopsy guidance", Review of Scientific Instruments, vol. 76, p. 064301-1-064301-6, (2005).

Lenkinski, R.E. et al., "Near-infrared fluorescence imaging of microcalcification in an animal model of breast cancer", Academic Radiology, vol. 10, pp. 1159-1164, (2003).

Manoharan, R. et al., "Raman spectroscopy and fluorescence photon migration for breast cancer diagnosis and imaging", Photochemistry and Photobiology, vol. 67(1), pp. 15-22, (1998).

Motz, J.T. et al., "Optical fiber probe for biomedical Raman spectroscopy", Applied Optics, vol. 43, No. 3, pp. 542-554, (2004).

Palmer, G.M. et al., "Diagnosis of breast cancer using optical spectroscopy", Medical Laser Application, vol. 18, pp. 233-248, (2003).

Palmer, G.M. et al., "Comparison of multiexcitation fluorescence and diffuse reflectance spectroscopy for the diagnosis of breast cancer", IEEE Transactions on Biomedical Engineering, vol. 50, No. 11, pp. 1233-1242, (2003).

Peters, V.G. et al., "Optical properties of normal and diseased human breast tissues in the visible and near infrared", Physics in Medicine and Biology, vol. 35, No. 9, pp. 1317-1334, (1990).

Redd, D.C.B. et al., "Raman spectroscopic characterization of human breast tissues: Implications for breast cancer diagnosis", Applied Spectroscopy, vol. 47, No. 6, pp. 787-791, (1993).

Shafer-Peltier, A.S. et al., "Raman microspectroscopic model of human breast tissue: implications for breast cancer diagnosis in vivo", Journal of Raman Spectroscopy, vol. 33, pp. 552-563, (2002).

Shah, N. et al., "Noninvasive functional optical spectroscopy of human breast tissue", Proceedings of the National Academy of Sciences of the United States of America, vol. 98, No. 8, pp. 4420-4425, (2001).

Shetty, G. et al., "Raman spectroscopy: elucidation of biochemical changes in carcinogenesis of oesophagus", British Journal of Cancer, vol. 94, pp. 1460-1464, (2006).

Yang, Y. et al., "Fundamental differences of excitation spectrum between malignant and benign breast tissues", Photochemistry and Photobiology, vol. 66(4), pp. 518-522, (1997).

Zysk, A.M. et al., "Optical coherence tomography: a review of clinical development from bench to bedside", J. Biomedical Optics, 12(5), pp. 051403-1 thru 051403-21, (2007).

Choi, J.H. et al., "Multimodal biomedical imaging with asymmetric single-walled carbon nanotube/iron oxide nanoparticle complexes", Nano Letters, vol. 7, No. 4, pp. 861-867, (2007).

Zysk, A.M. et al., Comment on "In vivo cancer diagnosis with optical spectroscopy and acoustically induced blood stasis using a murine Mca35 model", Medical Physics, vol. 34, Issue 3, p. 1130, (2007).

Boppart, M.D. et al., "$\alpha_7 \beta_1$-Integrin regulates mechanotransduction and prevents skeletal muscle injury", American Journal of Physiology: Cell Physiology, vol. 290, Issue 6, pp. C1660-C1665, (2006).

Toublan, F.J-J. et al., "Tumor targeting by surface-modified protein microspheres", Journal of the American Chemical Society, vol. 128, Issue 11, pp. 3472-3473, (2006).

Vinegoni, C. et al., "Integrated structural and functional optical imaging combining spectral-domain optical coherence and multiphoton microscopy", Applied Physics Letters, vol. 88, Issue 5, pp. 053901-1 thru 053901-3, (2006).

Vinegoni, C. et al., "Multi-modality imaging of structure and function combining spectral-domain optical coherence and multiphoton microscopy", Proc. of SPIE, vol. 6079, pp. 60791D-1 thru 60791D-8, (2006).

Boppart, S.A. et al., "Real-time optical biopsy and analysis of breast cancer using clinical optical coherence tomography", Journal of Clinical Oncology, Abstract presentation from the 2007 ASCO Annual Meeting Proceedings Part 1, vol. 25, No. 18S, (2007).

American Cancer Society, "2007 Cancer facts & figures", 56 pages, (2007).

Boppart, S.A. et al., "Optical coherence tomography: feasibility for basic research and image-guided surgery of breast cancer", Breast Cancer Research and Treatment, vol. 84, pp. 85-97, (2004).

Berg, W.A. et al., "Diagnostic accuracy of mammography, clinical examination, US, and MR imaging in preoperative assessment of breast cancer", Radiology, vol. 233, pp. 830-849, (2004).

Kawasaki, M., et al., "Diagnostic accuracy of optical coherence tomography and integrated backscatter intravascular ultrasound images for tissue characterization of human coronary plaques", Journal of the American College of Cardiology, vol. 48, No. 1, pp. 81-88, (2006).

Oldenburg, A.L. et al., "Molecular OCT contrast enhancement and imaging", Optical Coherence Tomography: Technology and Applications, Ch. 24, (2008).

Oldenburg, A.L. et al., "Optical coherence tomography", McGraw-Hill Encyclopedia of Science & Technology, (2005).

Oldenburg, A.L et al., "Imaging gold nanorods in excised human breast carcinoma by spectroscopic optical coherence tomography", Journal of Materials Chemistry, (2009).

* cited by examiner

SINGLEMODE　　　　　MULTIMODE, GRADED INDEX

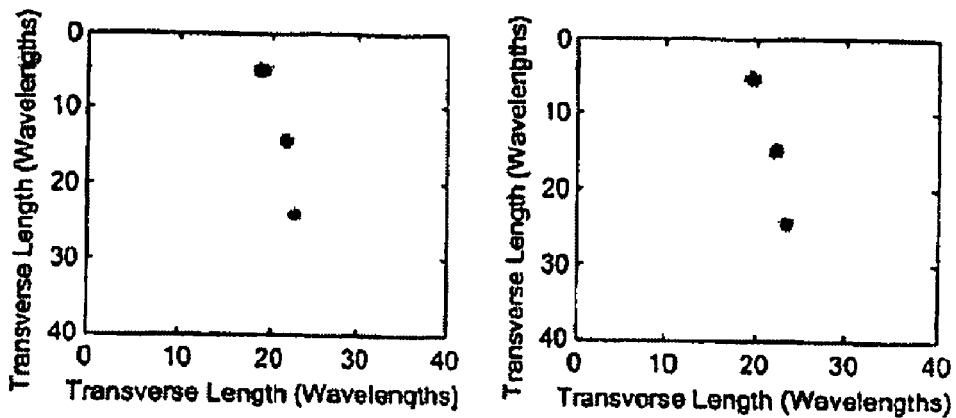
FIG. 21(a)   PLANE A
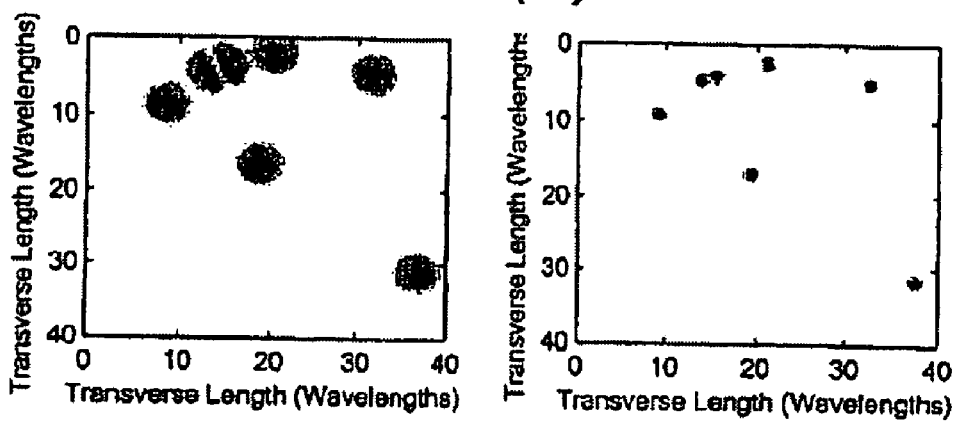
FIG. 21(b)   PLANE B
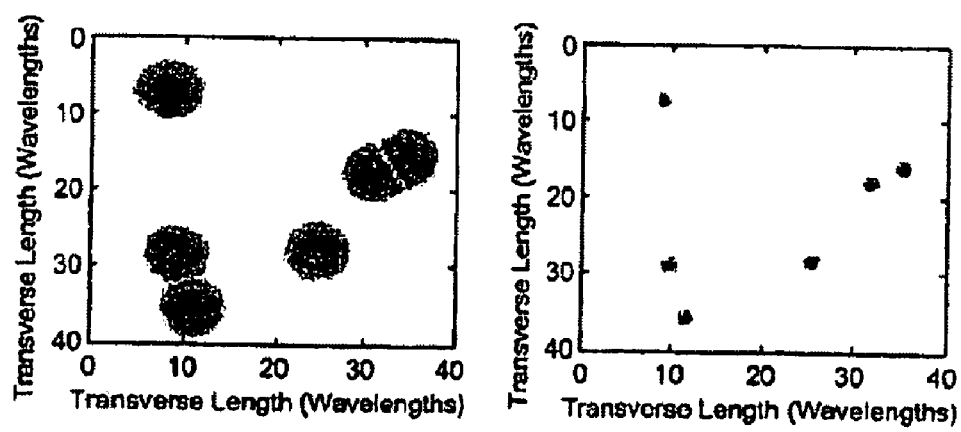
FIG. 21(c)   PLANE C $Q^2 + \beta^2 = (2k)^2$

DEVICE AND METHOD FOR IMAGING THE EAR USING OPTICAL COHERENCE TOMOGRAPHY

CROSS REFERENCE TO RELATED APPLICATION

This application claims benefit of U.S. Provisional Application No. 61/022,297, filed Jan. 18, 2008, entitled "DEVICE AND METHOD FOR IMAGING THE EAR USING OPTICAL COHERENCE TOMOGRAPHY," which is incorporated by reference in its entirety.

FEDERALLY SPONSORED RESEARCH OR DEVELOPMENT

The subject matter of this application may have been funded in part under a research grants from the National Institutes of Health, under Contract Number 1 R01 EB005221. The U.S. Government may have rights in this invention.

BACKGROUND

Optical coherence tomography (OCT) is a high-resolution medical and biological imaging technology. OCT utilizes low-coherence interferometry (LCI) to perform optical ranging within biological tissues. OCT has already previously been demonstrated for being a high resolution real time imaging modality that can provide near-histological information in other clinical applications such as ophthalmology, cardiology, and digestive disease. In use, OCT detects the reflections of low-coherence light, and cross-sectional imaging may be performed by measuring the backscattered intensity of light from structures in tissue. This imaging technique is attractive for medical imaging because it permits the imaging of tissue microstructure in situ. In situ imaging with OCT provides micron-scale imaging resolution without the need for excision and histological processing. OCT has been used in ophthalmology for high-resolution tomographic imaging of the retina and anterior eye. Recently, the technique has been applied for imaging a wide range of nontransparent tissues to investigate applications in tissues studies and medical applications in gastroenterology, urology, and neurosurgery.

OCT measures cross-sectional tomographic images in tissue and is similar to ultrasound B-mode imaging except that it uses light waves rather than sound. OCT also differs from ultrasound in that the detection in OCT is based on interferometry. In ultrasound, the time the ultrasound pulse takes to travel to a surface and be reflected back can be measured by an electronic clock. However, this is not possible with optical techniques because of the high speeds associated with the propagation of light. This limitation is overcome with the use of a reference light path and interferometry. A detailed presentation of the principles of operation of OCT and factors that govern its performance have been previously published. (See Huang D, Swanson, Lin C P, Schuman J S, Stinson W G, Chang W, Hee M R, Flotte T, Gregory K, Puliafito C A, Fujimot J G. Optical coherence tomography. Science. 1991: 254:1178-1181; and Swanson E A, Izatt J, Hee M R, Huang D, Lin C P, Schuman J S, Puliafito C A, Fujimoto J G. In vivo retinal imaging by optical coherence tomography. Optics Lett. 1993; 18:1864-1866; both of which are herein incorporated by reference.)

OCT systems may use fiber optics and a compact diode light source similar to those used in compact disc players. Precision distance measurements may be performed by Michelson-type interferometry. In this case, light from the source is split by an optical fiber splitter, which functions as an interferometer. One of the fibers directs light to the tissue and the other to a moving reference mirror, in the case of time-domain OCT. The distal end of the optical fiber can be interfaced to a catheter. In time-domain OCT, the position of the reference mirror is precisely controlled by the system electronics. The light signal reflected from the tissue is recombined with the signal reflected from the mirror. Interference between the light reflected from the tissue and the light reflected from the reference mirror occurs only when the two path lengths are matched to within the coherence length of the light source. This allows precise (micron scale) determination of the distance within the sample from which the light was reflected.

OCT therefore measures the intensity of backscattered (reflected) light from within the tissue, plotted as a function of depth. A cross-sectional image is produced in a manner similar to radar by recording axial reflectance profiles while the transverse position of the optical beam on the tissue specimen is scanned. The image is displayed either in gray scale or false color in order to differentiate tissue microstructure.

Spectroscopic optical coherence tomography (SOCT) is an extension of OCT that can differentiate between different types of tissue. In addition to the normal OCT measurement of the intensity of light backscattered from the sample, SOCT measures the spectral absorption and scattering data from the tissue. Tissue structure can be resolved based on local optical densities, ignoring the frequency dependent changes. SOCT resolves both the amplitude, which contains the scattering and refractive of index information, and the frequency, which contains spectroscopic molecular composition information based on the absorption and scattering properties.

Contrast agents may be used to improve the specificity and targeted tissue visualization of images obtained from an imaging technique, including OCT. Conventional contrast agents serve to increase the intensity of backscattered light. For example, air-filled micro-bubbles and engineering microspheres may be introduced into tissue to increase the backscattering from tissue. In another example, a molecular contrast agent can be used in a pump-probe technique to change the absorption properties of the light.

Otoscopy based on pneumatic otoscopes is currently the primary diagnostic tool for ear pathologies, and virtually every physician in internal medicine, pediatrics, or family practice medicine. However, the diagnostic process is currently more subjective than objective, more of an art than a science. Trained eyes are required to decipher a wide variety of tympanic membrane and middle-ear images and findings, some of which are empirically linked to various disease states. The treatments that follow rely on the individual judgments of physicians.

Currently, few objective tests are available to assess the significance of the pathology of the ear, and limitations are more evident in the primary care or general pediatricians' office, remote from access to specialists in otolaryngology. Furthermore, evaluation and monitoring of treatments (such as antibiotic treatments in otitis media (OM) or otitis media with effusion (OME)) in patients is often difficult, because quantitative measures are lacking. All of these limitations can be ultimately attributed to the qualitative nature of the information acquired, because a pneumatic otoscope is basically a low-magnification microscopy-type instrument.

Other than pneumatic otoscopy, there are mainly two additional in vivo diagnostic methods for identifying middle-ear pathologies: tympanometry and acoustic reflectometry. Tympanometry measures sound energy transmission/reflection (i.e., compliance/mobility) of the tympanic membrane by recording a tympanogram in response to air pressure changes inside the ear canal. Tympanograms are classified as type A (normal), type B (indicating middle-ear effusion) or type C (indicating eustachian tube dysfunction). Acoustic reflectometry measures the acoustic reflectivity spectrum of the middle-ear in response to an incident sound. The curve of the spectrum is used to characterize the extent of OME.

Comprehensive evidence assessment on the accuracy (sensitivity and specificity) of the three methods reveals that pneumatic otoscopy has better performance than the two acoustic methods. Furthermore, pneumatic otoscopy is more cost-effective and easier to use. Thus, a 2004 clinical practice guideline on OME from the American Academy of Pediatrics has recommended that clinicians use pneumatic otoscopy as the primary diagnostic method (See American Academy of Family Physicians, American Academy of Otolaryngology-Head and Neck Surgery, and American Academy of Pediatrics Subcommittee on Otitis Media With Effusion, "Otitis Media With Effusion," Pediatrics, 113, 1412-1429, 2004). However, none of the three described established methods are able to assess or monitor the presence of biofilms within the middle ear.

Biofilms are microorganisms that grow collectively in adhesive polymers (mainly extracellular polysaccharides (EPS)) on biologic or non-biologic surfaces. Biofilms can virtually colonize any indwelling device (catheters, artificial joints, contact lenses) and different tissues (oral soft tissues, teeth, middle ear, gastrointestinal tract, urogenital tract, airway/lung tissue, etc.) (Costerton J W, Stewart P S, Greenberg E P (1999) Bacterial biofilms: a common cause of persistent infections. Science 284, 1318-1322; Donlan R M (2001) Biofilms and device-associated infections. Emerg Infect Dis 7, 277-281; Donlan R M (2002) Biofilms: microbial life on surfaces. Emerg Infect Dis 8, 881-890; Fux C A, Costerton J W, Stewart P S, Stoodley P (2005) Survival strategies of infectious biofilms. Trends Microbiol 13, 34-40). Bacteria embedded in biofilms is very difficult to be eradicated. Biofilms colonized on devices are the sources of most medical device-related infections. Bacterial biofilms are found colonizing the middle ear in most patients with chronic otitis media and may be the cause of recurrent otitis media (L. Hall-Stoodley, F. Z. Hu; A. Gieseke, L. Nistico, D, Nguyen, J. Hayes, M. Forbes, D. P. Greenberg, B. Dice, A. Burrows, P. A. Wackym, P. Stoodley, J. C. Post, G. D. Ehrlich, J. E. Kerschner, "Direct detection of bacterial biofilms on the middle-ear mucosa of children with chronic otitis media," JAMA. 296, 202-211, 2006).

In one publication, the use of OCT for imaging the middle ear structures has been studied, primarily for assessing feasibility for imaging the ossicles within the middle ear (See C. Pitris, K. T. Saunders, J. G. Fujimoto, M. E. Brezinski, "High-resolution imaging of the middle ear with optical coherence tomography: a feasibility study," Arch Otolaryngol Head Neck Surg. 127, 637-642, 2001.) This study was conducted on cadaver tissue. Other optical imaging efforts have focused on imaging the round window within the middle ear, but this requires surgical intervention for access. A recent study in JAMA (See L. Hall-Stoodley, F. Z. Hu; A. Gieseke, L. Nistico, D, Nguyen, J. Hayes, M. Forbes, D. P. Greenberg, B. Dice, A. Burrows, P. A. Wackym, P. Stoodley, J. C. Post, G. D. Ehrlich, J. E. Kerschner, "Direct detection of bacterial biofilms on the middle-ear mucosa of children with chronic otitis media," *JAMA*. 296, 202-211, 2006.), documented the evidence of biofilms being linked to chronic OM, and used invasive tissue sampling followed by confocal microscopy for identifying biofilms. However, all of these methods were invasive and required getting a tissue sample. There is a need for non-invasive detection of biofilms in the inner ear or analysis of effusion composition in OME.

SUMMARY

In one aspect, the invention provides a method of forming an image of ear tissue. The method includes non-invasively inserting a fiber-based device into a patient's ear canal. The method further includes acquiring OCT data from ear tissue while the fiber-based device is in the ear canal and converting the OCT data into at least one image. In one aspect, the method further includes performing further data analysis on the image while the fiber-based device is in the ear canal.

In another aspect, the invention provides a system for imaging ear tissue in real-time. The system includes a core imaging unit which generates a low-coherence interferometry signal and a fiber-based device connected with an otoscope. The fiber-based device is in communication with and receives the low-coherence interferometry signal from the core imaging unit and sends a second signal back to the core imaging unit. OCT data is generated by the core imaging unit.

In yet another aspect, the invention provides a method of analyzing ear tissue. The method includes beginning a non-invasive procedure on a patient exposing middle ear tissue. The method also includes acquiring OCT data from the middle ear tissue. In one aspect, the method further includes analyzing the OCT data and classifying the ear tissue upon analyzing the OCT data.

The scope of the present invention is defined solely by the appended claims and is not affected by the statements within this summary.

The following definitions are included to provide a clear and consistent understanding of the specification and claims.

The term "tissue" means an aggregate of cells and their intercellular substances. Tissue includes diseased tissue and normal tissue. Diseased tissue includes cancerous and benign tumors, as well as biofilms and abnormal fluids or cells within the ear, including those of pathogenic organisms, The term "ear tissue" includes all tissue and structures within an ear. The term "middle ear tissue" includes all tissue and structures within the middle ear, including the tympanic membrane.

The term "radiation" means electromagnetic radiation, including optical radiation in the visible, infrared, ultraviolet, or other spectral regions.

The term "sample signal" means at least a portion of the radiation that is scattered from, reflected from, and/or transmitted through a sample, including a tissue sample.

The term "optical property", with respect to tissue or other material, means a characteristic of the material that may be quantified by measuring a change in electromagnetic radiation when impinged upon the material, or an emission of electromagnetic radiation from the material.

The term "optical path" means the path along which electromagnetic radiation propagates.

The term "path length" means the distance between two objects based on optical measurements. The path length through a medium between two objects is dependent on the refractive index of the medium, such that the path length may be different from the physical distance between the two objects.

The term "optically coupled" with respect to two components means that radiation is transmitted from one component to the other component.

The term "distal", with respect to a device or needle, means a position or direction that would be toward or inside the body of the patient when the device or needle is inserted.

The term "OCT" or "Optical Coherence Tomography" means any type of process which uses low-coherence interferometry (LCI) and includes LCI, TD-OCT, SD-OCT, SOCT, and any other of the vast number of other OCT modalities.

The term "OCT data" or "Optical Coherence Tomography data" means any type of data acquired from a process which uses low-coherence interferometry (LCI) and includes data acquired as a result of using LCI, TD-OCT, SD-OCT, SOCT, and any other of the vast number of other OCT modalities.

The term "real-time" means the live or nearly instant sending and receiving of information, such as sound, text or image. Real-time can also refer to the sending or receiving of information before an event expires. For example, in surgery, a real-time assessment of a tumor consists of the sending of information to a surgeon during the surgery and before then ending of that surgery so that a surgeon can make an assessment before the surgery is over.

An "otoscope" is a medical device used to visualize the ear canal, tympanic membrane, and middle-ear and can be used to detect and diagnose ear diseases such as otitis media (OM) or otitis media with effusion (OME). A "pneumatic otoscope" is a medical device used to visualize the ear canal, tympanic membrane, and middle-ear. The use of pneumatic otoscope, which applies a pressure to the ear canal to displace the tympanic membrane, is simply another added technique to improve our ability to detect/diagnose an effusion.

The term "non-invasive" or "non-invasively" means a procedure that does not require inserting an instrument or device through the skin or biological membrane of a patient, but can include insertion into a body cavity or opening, such as an ear canal or oral cavity, so long as no skin or biological membrane is penetrated.

The term "ear" refers to a structure used by animals to aid in hearing. The "ear" can be divided into an "outer ear," a "middle ear," and an "inner ear." The "outer ear" includes an ear canal and ear lobe. The "middle ear" includes all structures behind and including the tympanic membrane.

The term "expose" or "exposing" means to bring tissue or cells to be imaged close enough to an OCT device so that OCT data may be collected from that tissue or cells. For example, the phrase "exposing tissue to an OCT device" means bringing the tissue and the OCT device close enough to each other so that OCT data may be collected from the tissue.

BRIEF DESCRIPTION OF THE DRAWINGS

The invention can be better understood with reference to the following drawings and description. The components in the figures are not necessarily to scale, emphasis instead being placed upon illustrating the principles of the invention.

FIG. 14A depicts a cross-sectional scan image of the biofilm showing the biofilm at the bottom and on the top of inner surfaces. Arrows indicate voids in the biofilm. FIGS. 14B and 14C depict a three-dimensional reconstruction of the biofilm showing detailed structural information at the bottom of the image having microcolonies (indicated by arrows). Bars are 20 μm.

FIG. 15A depicts a cross sectional scan image of the biofilm showing microbial cell aggregates and matrix. Arrows indicate cell aggregates or voids. FIG. 15B depicts a three-dimensional reconstruction of the biofilm showing uneven surfaces and detachment of cell aggregates (indicated by an arrow). Bars are 200 μm. (See Xi C, Marks D L, Schlachter S, Luo W, Boppart S A. "High-resolution three-dimensional imaging of biofilm development using optical coherence tomography," J. Biomed. Opt. 11(3):034001-1-134001-6, 2006.)

FIG. 16D depicts a schematic which shows the micro-optics of a fiber-optic OCT device. When used with a device for imaging the middle ear using optical coherence tomography, the rigid metal needle barrel can be replaced with a semi-flexible plastic fiber protector for attachment to an ear speculum.

FIG. 20(*b*) depicts an example of a band volume for an instrument, in accordance with the present invention, having a numerical aperture of 0.5 and bandwidth from $0.8 k_{max} < k < k_{max}$.

FIG. 20(*c*) shows the projection of the simulated data collapsed (summed) along one transverse direction, while FIG. 20(*d*) is a projection of the computed reconstruction of the scatterers.

FIGS. 21(*a*)-21(*c*) show three pairs of en face images of the time-domain data (left side) and the reconstructed volume (right).

FIG. 32(*b*) shows a sampling lattice for selected ($\beta$, |Q|) values on a uniform (k, |Q|) grid; and FIG. 32(*c*) shows a sampling lattice for selected (k, |Q|) values on a uniform ($\beta$, |Q|) grid.

DETAILED DESCRIPTION

The present invention makes use of the discovery that the integration of an OCT modality capable of quantitative (i.e., depth-resolved) structural characterization compliments pneumatic otoscopy for enhanced diagnostic ability. This integration not only can provide quantitative data on the status of ear health and disease, but also provide repeated monitoring for following disease progression or regression following medical treatments. In addition, the pneumatic otoscope instrument augments OCT by allowing the OCT probe to gain access to the ear anatomy, and to facilitate tracking of the position where an OCT measurement is being acquired. Hence, the present invention permits not only the standard qualitative visualization and video capture of the ear anatomy and pathology, but also simultaneous OCT quantification of tympanic membrane position and integrity, middle-ear anatomy, and the presence and classification of middle ear effusions.

The present invention also makes use of the discovery that because OCT or LCI can be performed through an otoscope, preferably a pneumatic otoscope, it is possible for the OCT or LCI light beam to detect and image the tissue directly at the site where the otoscope is inserted into, such as into the ear canal, to visualize outer-ear and middle-ear structures. Thus, in this application, OCT can be used to directly image ear anatomy, but also allows OCT to image tympanic membrane position and integrity, middle-ear anatomy, and the presence and classification of middle ear effusions, rather than relying on the subjective diagnosis and judgment of a trained physician, which suffers from the possibility of human error and inexperience. Imaging and quantifying the ear tissue to be diagnosed by a physician using OCT, instead of just relying on visual cues, will likely reduce or eliminate subjective assessment, and will likely provide new, complementary, quantitative data to more accurately make a diagnosis and monitor health and disease response or progression.

Thus, the present invention makes use of the discovery that OCT can be used as an intra-operative and intra-procedure guidance tool for physicians using an otoscope, providing them with real-time microscopic assessment of middle ear anatomy, the application of which is best illustrated in three important applications, described herein.

Figure 1:
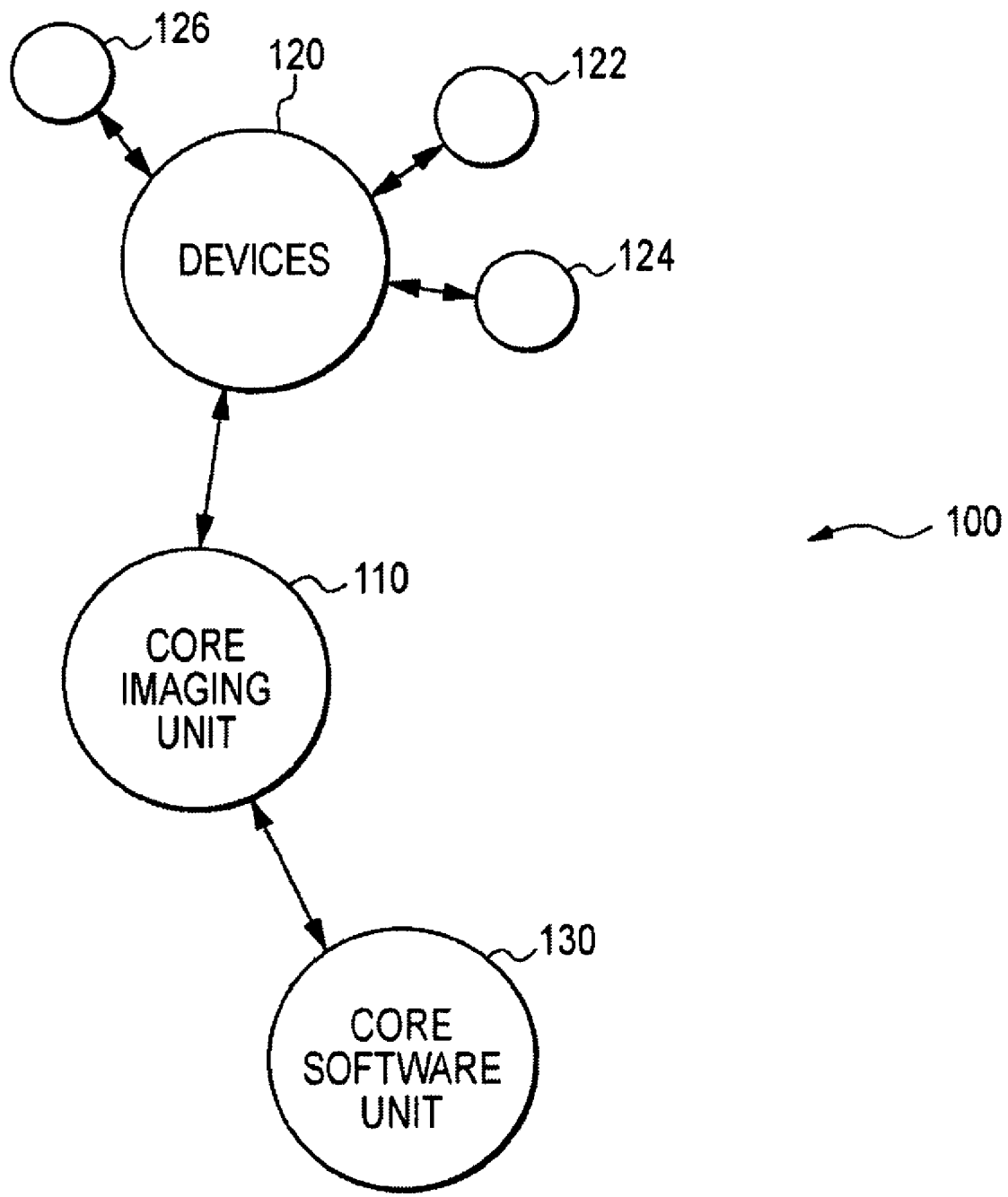
FIG. 1 depicts a schematic representation of an OCT system for acquiring real-time data in vivo.

FIG. 1 depicts a schematic representation of an optical coherence tomography (OCT) system 100 for acquiring real-time in vivo data. OCT system 100 is a highly modular system that can interface with various devices to widen its range of potential applications as well as interfacing with newer visualization algorithms and classification methods, as discussed herein. The modular nature of the OCT system 100 allows a user to seamlessly interchange these components adapting the system to a user's particular needs and criteria. OCT system 100 includes a core imaging unit 110 that serves as a central unit which interfaces with two other categories of hardware or software components: devices 120 and a core software unit 130.

Figure 2A:
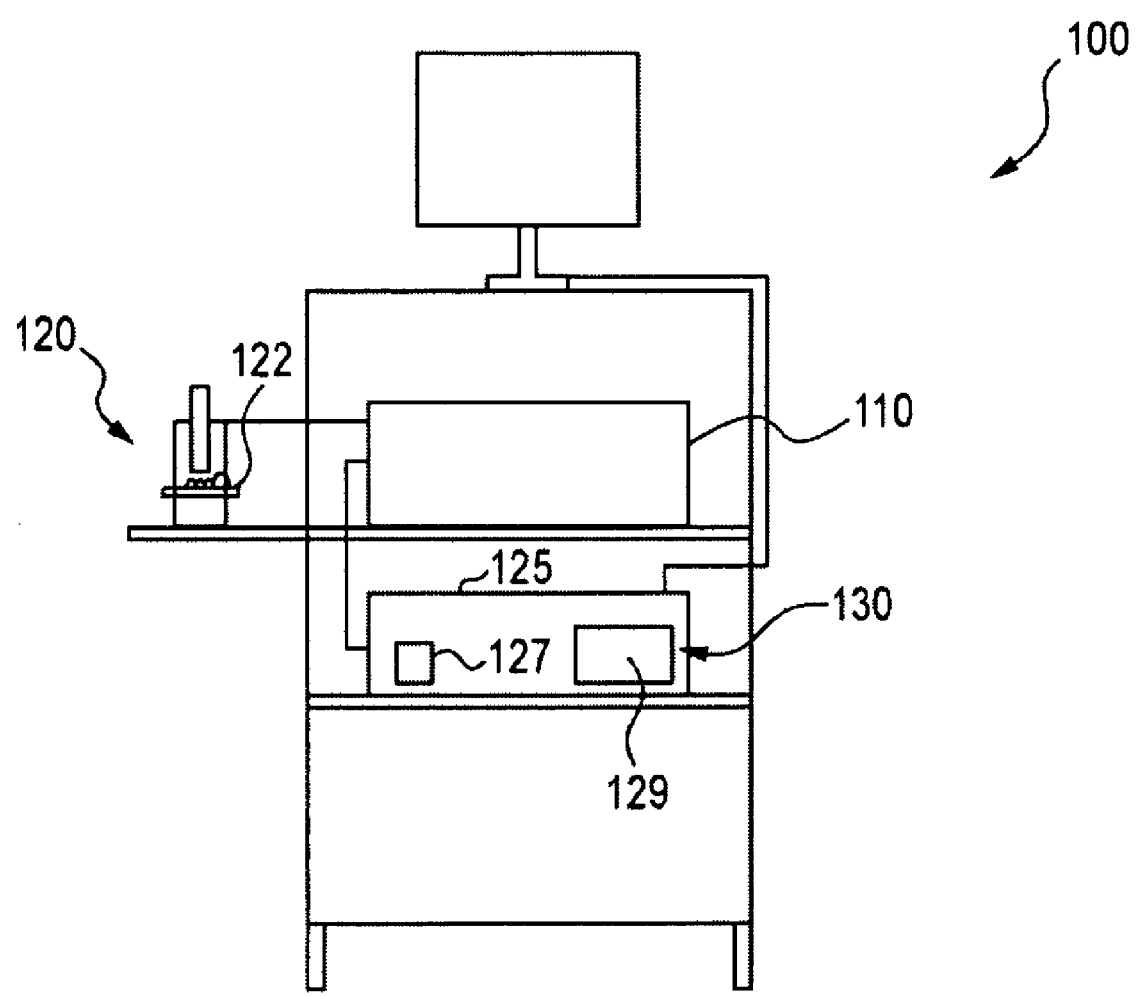
FIG. 2A depicts an OCT system for acquiring real-time data in vivo.
Figure 2B:
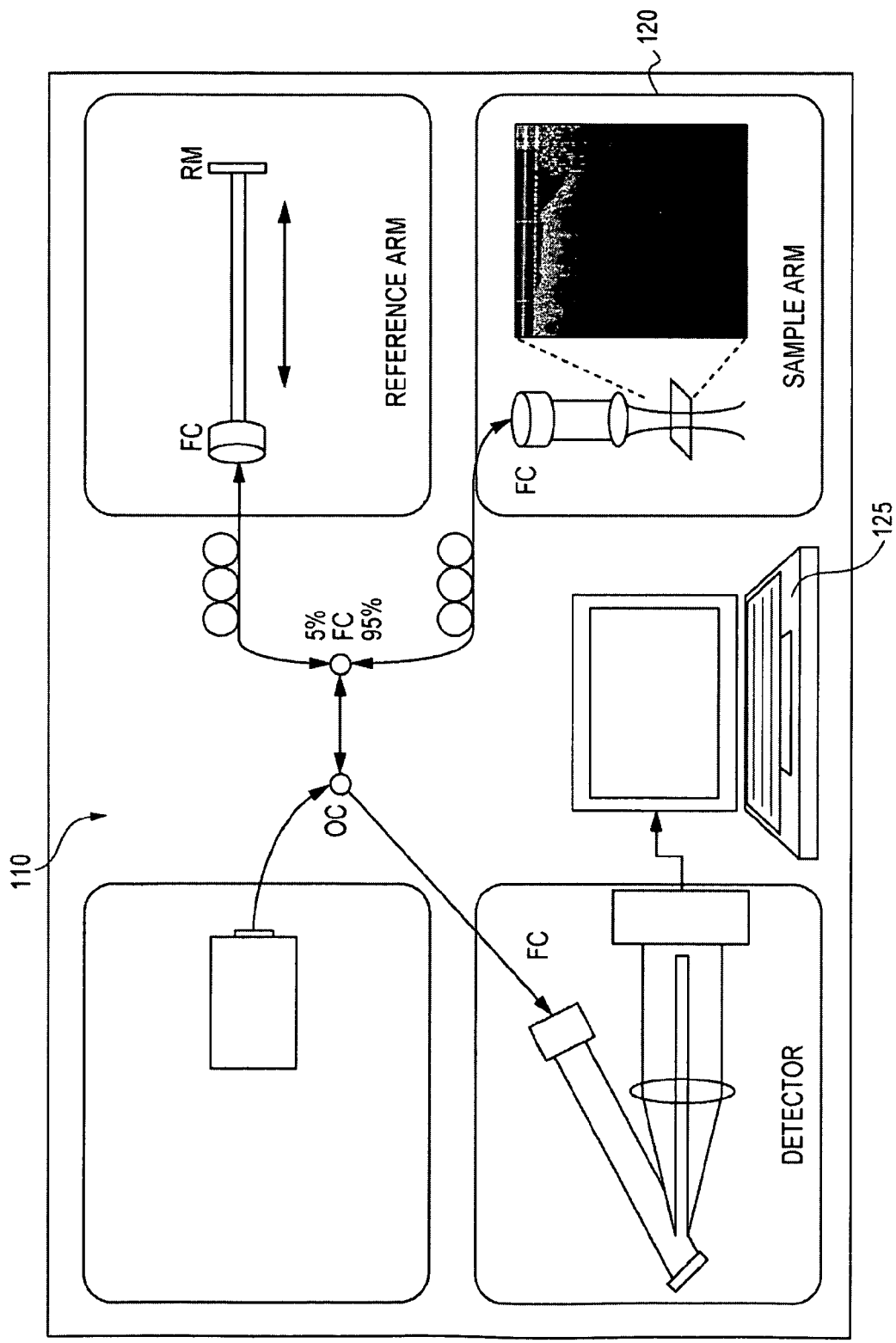
FIG. 2B depicts a schematic diagram outlining the optical components and hardware used in an SD-OCT system.

As shown in FIGS. 2A and 2B, the core imaging unit 110 interfaces and is in communication with device 120. The core imaging unit 110 generates a broadband optical signal which is then run through the device 120 to a tissue sample 121 which is to be analyzed. The signal is then reflected back from the tissue sample 121, back through the device 120 and then to the core imaging unit 110, upon which the reflected signal is combined with the reference signal to create or "generate" an LCI signal, which is detected using a detector and OCT data is acquired from the reflected signal. The core imaging unit 110 is in communication with the core software unit 130 which is run on a computer 125, as shown in FIG. 2A, and sends the OCT data to the core software unit 130 for image processing and analysis. The core software unit 130 is stored in a computer readable storage medium 129 which is connected with the computer 125. The computer 125 also is connected with a processor 127 which runs the core software unit 130. Upon receiving the OCT data, the core software unit 130 converts the raw OCT data into an OCT image and performs further data analysis on the OCT data in order to enhancing the image and/or to classify tissue seen in the image. Preferably, the core software unit 130 can perform the further data analysis on the OCT data in real-time during a procedure, such as surgery. In this manner, the OCT system 100 can not only image tissue and generate OCT data in real-time, but can also provide a real-time analysis of the OCT data.

Upon imaging the tissue and classifying the tissue, or enhancing the image of the tissue, a user, such as a surgeon or physician, is then able to make a decision regarding how to proceed. For example, if the tissue is being analyzed to determine if it contains a biofilm, then the tissue specimen may be classified as either having or not having a biofilm. Upon receiving this classification information, the user is then able to treat the tissue classified or recommend further treatment in order to mitigate any damage this tissue may cause. Additionally, the tissue classifications can be very useful in diagnosing and preventing certain types of inner ear conditions, such as otitis media (OM) or otitis media with effusion (OME).

Preferably, the OCT system 100 is used during a procedure, such as a non-invasive procedure in which a patient is having an otoscope inserted into a portion of the patient's ear canal. Preferably, the patient is a living human patient. Preferably, the OCT system 100 uses SD-OCT to improve the sensitivity of signal detection and reduce the amount of time required to obtain OCT data allowing for a real-time analysis of a patient's tissue. In addition to using SD-OCT, classification algorithms 180 can be used either alone or in conjunction with SD-OCT in order to reduce the amount of time required to classify the tissue being analyzed with the OCT system 100. In this manner, the OCT system can be used to provide a real-time analysis of the patient's tissue. A real-time analysis allows the user to make more informed decisions, such as whether or no to remove certain tissue, before completing the procedure. This prevents the patient from having to undergo the procedure again, or from having too much tissue removed.

Figure 3A:
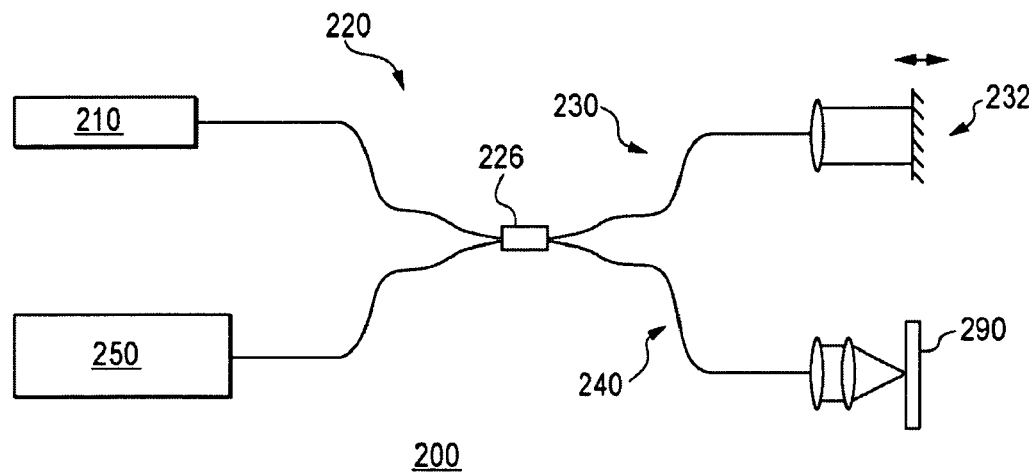
FIG. 3A depicts a schematic representation of a device for acquiring OCT data.

The core imaging unit 110 is an LCI or OCT engine, such as a Michelson- or Mach-Zender-type interferometer with accompanying detection, acquisition, processing, and display components, or such as a 3D SDOCT system manufactured by Bioptigen, Inc. of the Research Triangle Park in North Carolina. FIG. 3A is a schematic representation of a low-coherence interferometry device 200 for analyzing a portion of tissue 290. The device 200 includes a low-coherence laser source 210, a fiber optic assembly 220, a reference assembly 230, a sample assembly 240 and an analyzer 250. The fiber optic assembly 220 includes a beam splitter 226 that divides the radiation between the reference assembly 230 and the sample assembly 240. The reference assembly 230 includes a reference mirror 232, which may be moved toward or away from the fiber optic assembly 220. The sample assembly 240 exposes the tissue to the radiation and obtains a sample signal of the radiation that may be scattered, reflected and/or transmitted by the portion of the tissue that is exposed to the radiation.

At least a portion of the sample assembly 240 of a low-coherence interferometry device 200 may be incorporated into a device that can be inserted into tissue in a patient. The radiation that is reflected from the reference mirror 232 constitutes the reference signal, and the reference signal and sample signal are combined to form an interference signal. The interference signal may be directed to the analyzer 250, or the reference and sample signals may be directed to the analyzer and then combined to form the interference signal. The analyzer 250 may process the signals to measure or display the low-coherence interferogram. The analyzer 250 may also determine the refractive index of the tissue and may optionally determine at least one other optical property of the tissue. The analyzer 250 may provide feedback, such as a visual display of the determined values of any optical properties and/or a signal indicating whether a particular tissue has been identified.

In one example of a low-coherence interferometry device, the low-coherence laser source is a Nd:YVO$_4$ pumped titanium: sapphire laser that yields radiation having a wavelength range from approximately 650 nm to approximately 900 nm after passing through a non-linear fiber. Dispersion and polarization are matched in the reference and sample assemblies. A precision galvanometer is used to scan a reference mirror, and non-linearities in galvanometer speed are relatively small so that interferometric triggering methods are not used. Special fibers, a 3-dB splitter, lenses, signal filtering, and demodulation are used to support the broad optical and electronic bandwidths. The analyzer collects the interferogram data at multiple reference mirror positions and digitizes the signal with an oversampling ratio of at least 2. For applications involving real time analysis, spectral detection with a CCD detector array or accelerated digitization and processing using a field-programmable gate array (FPGA) may be used.

Some OCT engines currently being used are based on traditional spectral domain optical coherence tomography (SD-OCT) engines. A description of an SD-OCT engine can be found in Nguyen F T, Zysk A M, Chaney E J, Kotynek J G, Oliphant U J, Bellafiore F J, Rowland K M, Johnson P A, Boppart S A, "Intraoperative High-Resolution Identification of Breast Tumor Margins," Submitted to American Journal of Surgery (2007), and in R. Leitgeb, C. Hitzenberger, and A. Fercher, "Performance of Fourier domain vs. time domain optical coherence tomography," Opt. Express 11, 889-894 (2003), all of which is hereby incorporated by reference.

Some other OCT systems being used are based on spectroscopic optical coherence tomography (SOCT).

Acquiring OCT data includes dividing low-coherence radiation between two paths, the reference path and the sample path. Radiation traveling along the reference path is reflected against a reference mirror and then collected as a reference signal. Radiation traveling along the sample path is reflected against a sample mirror and then into the sample tissue. Any radiation that is scattered back from the tissue sample is reflected against the sample mirror and then collected as a sample signal. The signals are filtered to match the dispersion and polarization and then combined into an interference pattern. The resulting interference pattern corresponds to the signal from a single point within the sample. The depth of this point is determined by the distance between the sample and the light source relative to the distance between the reference mirror and the light source, as constructive interference is maximized for signals having the same path length. Variation of these relative distances provides for signals from points at different depths within the sample. Two-dimensional in-plane translation of the sample signal relative to the sample can provide signals across a particular area of the sample.

A variety of techniques can be used to divide the laser radiation into two signals. For example, the radiation can be intersected by a partially reflective mirror, reflecting a portion of the radiation at an angle and permitting the remainder of the radiation to pass through the mirror. The radiation may also be passed through a fiber optic assembly that is configured to split the incident radiation into two fiber optic paths. Variation of the scan depth can be accomplished by moving the reference mirror and/or the sample along the path of the radiation. Variation of the lateral position of the scan can be accomplished by changing the angle of the sample mirror and/or by moving the sample.

Figure 3B:
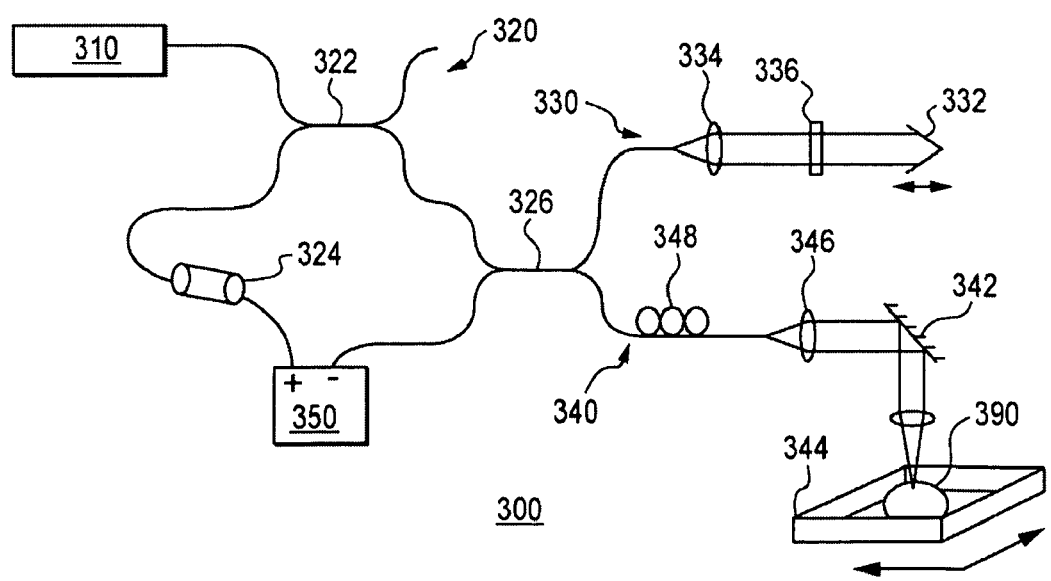
FIG. 3B depicts a schematic representation of a device for acquiring OCT data.

FIG. 3B is a schematic representation of an example of a device 300 for acquiring OCT data from a sample 390. OCT device 300 includes a low coherence laser source 310, a fiber optic assembly 320, a reference assembly 330, a sample assembly 340 and a detector 350. The fiber optic assembly 320 may include a preliminary beam splitter 322 that diverts 10% of the radiation to adjustable attenuator 324 connected to the detector 350. The fiber optic assembly 320 includes a beam splitter 326 that divides the radiation between the reference assembly 330 and the sample assembly 340. The radiation that is reflected from the reference assembly 330 and the sample assembly 340 is directed to the detector 350. Reference assembly 330 includes reference mirror 332, which may be moved toward or away from the fiber optic assembly 320. The reference assembly 330 may include fiber collimator 334, for collection of the radiation reflected from the reference mirror 332, and may include a dispersion matching glass 336 to match the dispersion of the reference signal with the sample signal. The sample assembly 340 includes sample mirror 342, which reflects the radiation to the sample 390 in the sample holder 344. The orientation of the sample mirror 342 may be varied to provide for scanning of the radiation across an area of the sample. In addition to or instead of changes in the orientation of the sample mirror 342, the sample holder 344 may be moved along the length and width of the sample. The sample assembly 340 may include fiber collimator 346, for collection of the radiation reflected from the sample mirror 342, and may include a polarization matching paddle 348 to match the polarization of the sample signal with the reference signal. The detector 350 can perform initial processing of the signal to provide the OCT data. Initial processing may include digitization, noise removal and digital aberration correction.

If the laser source has an ultra-broad spectrum, the signal should be transmitted through free space, since fiber-optic components typically cannot accommodate the extremely broad spectrum. A spectral domain OCT setup may also be used to improve the resolution. For applications involving real time analysis, a real time SD-OCT based on a field-programmable gate array (FPGA) implementation can be used. The SD-OCT sample radiation can be delivered to internal body locations with the use of fiber-optic devices and catheters.

As shown in FIG. 1, the core imaging unit 110 is able to interface with a variety of devices 120, such as handheld devices 122, free-space optical devices 124, and fiber based devices 126. Having this flexibility allows the OCT system 100 to be adapted for use in a variety of different scenarios. The modular hand held device 122 is any type of probe or optical instrument that can be grasped by a user's hand and be aimed at tissue on or within a patient. The hand held device 122 includes things such as otoscopes for imaging an ear. The modular hand held device 122 can be used during a procedure to obtain images of high resolution three-dimensional volumetric data cubes in various areas along and beneath a surface of tissue. Alternatively, depending on the accessibility of the cavity, the hand held device 122 can be used to scan around cavity walls in search of specific types of tissue or to obtain certain measurements.

In addition to the hand held device 122, the core imaging unit 110 can also interface with various types of free-space optical devices 124 that are currently being used by doctors, such as microscopes, heads-up displays, visual magnification eyewear, and wide-field digital cameras, and other such optical devices. Free-space optical devices 124 include any devices or probes which allow significant free-space light propagation in a sample path, especially near the sample surface. By adding the imaging capabilities of OCT, through the core imaging unit 110, to a free-space optical device 124, such as a light microscope, a user can not only get a bright-field image afforded by light microscopy but can also gain a microscopic view of the tissue not only on the surface, but more importantly a few millimeters underneath the surface of the tissue. By taking a traditional imaging technique used to guide surgeons during surgery, such as a free-space optical device 124, and complimenting it with the high-resolution subsurface imaging capabilities of OCT, the user is provided with a method to image tissue on a macro- and microscopic level on and beneath the surface of the tissue and with information on the type of tissue imaged. The high-resolution cross-sectional imaging capabilities that the OCT system 100 provides in real-time allows the user to see subsurface tissue features on the same size scale as a pathologist would in light microscopy evaluation of resected specimens.

In addition to free space optical devices 124, the core imaging unit 110 can also be interfaced with a number of fiber based devices 126. Free space optical devices 124 and fiber based devices 126 can be used to image tissue, such as middle ear tissue. The free space optical devices 124 are best used for doing a wide-field survey and analysis. Meanwhile, to image deeper into the specimen or to gain a physical measure of a tissue or cavity, such as middle ear tissue, a fiber based device 126 may be inserted into the middle ear to obtain measurements or determine if a biofilm is present, for example.

Fiber based device 126 is any device which can be used to guide light from a first location to a second location, and includes things such as a fiber optic cable or optical fiber. The fiber based devices 126 are typically at least 125 microns in diameter, which is a typical size for an optical fiber, and are used to gain access to sites that cannot be imaged using bulkier devices such as those based on free space optics. The fiber based devices 126 can be attached to optical instruments, such as otoscopes, and be inserted into an ear canal in order to examine ear tissue. Typically, optical fibers are made of quartz, glass, or a transparent plastic, such as poly(methyl methacrylate) or polystyrene with a fluoropolymer cladding. Examples of optical fibers include single-mode fibers, multimode fibers, photonic-crystal fibers, hollow-core fibers, polarization-maintaining fibers and dual-clad fibers. Typical diameters for optical fibers are from 5 to 1,000 micrometers. The optical fiber may be a single-mode fiber or a multi-mode fiber. Single-mode glass fibers have diameters on the order of 10 micrometers. Multi-mode glass fibers have diameters on the order of 50-100 micrometers. Plastic optical fibers have diameters on the order of 1,000 micrometers.

Figure 4:
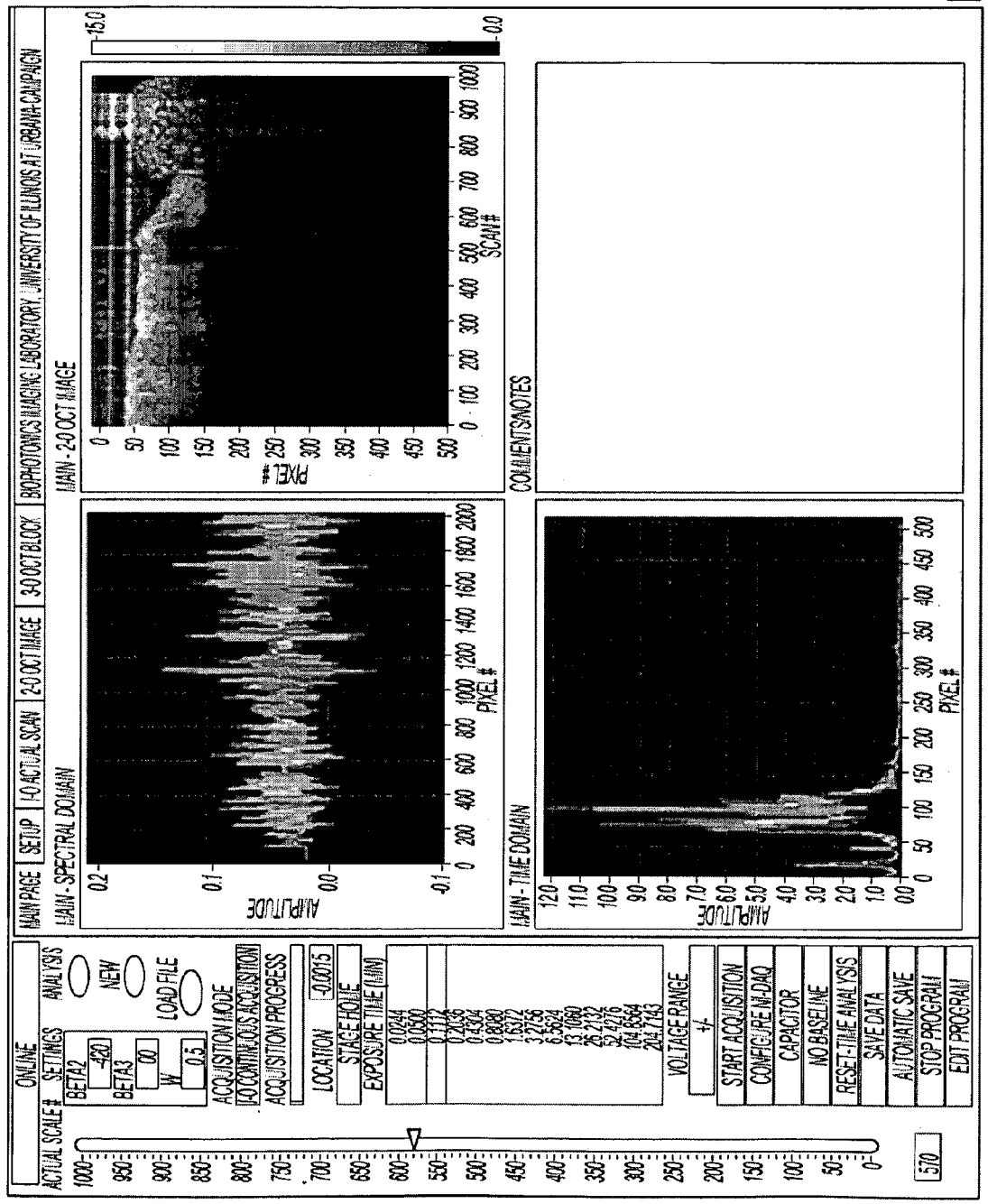
FIG. 4 depicts a software graphical user interface used to drive an OCT system.

In addition to the devices 120, the core imaging unit 110 also interfaces with the core software unit 130 which is used to drive the system, collect, and store the LCI depth scans and OCT images, as shown in FIGS. 2-4, for example. Upon generating a low-coherence interferometry first signal which is then run through the device 120 to a tissue sample 121, a second signal is then reflected back from the tissue sample 121, back through the device 120 and then to the core imaging unit 110. The core imaging unit 110 then detects the second signal using a detector and generates data which is acquired from the second signal. The generated data is then sent to the computer 125 for data analysis. The core software unit 130 is stored in a computer readable storage medium 129 which is connected with the computer 125. The computer 125 also is connected with a processor 127 through which the core software unit 130 is run.

In one embodiment, the core imaging unit 110 interfaces with a device 120 which scans over a wide field. With such a high-resolution imaging modality and large scanning area provided by the core imaging unit 110, there is a greater need to quickly process and interpret the data so that OCT images can be viewed and evaluated in real-time before the procedure has ended. If the OCT system is to provide images to a user in real-time while the patient is undergoing surgery, it is necessary to process and interpret the data quickly so a decision can be made. Therefore, the OCT system 100 includes the core software unit 130 which includes algorithms which help to process and interpret the data quickly in order to image large areas and identify the type of tissue being imaged (See Zysk and Boppart, Computational methods for analysis of human breast tumor tissue in optical coherence tomography images, J Biomedical Optics, 11:054015, 2006; and see Ralston T S, Marks D L, Carney P S, Boppart S A. Interferometric synthetic aperture microscopy, Nature Physics, 3:129-134, 2007, all of which are incorporated by reference herein).

Similar to the hardware portion of the OCT system 100, the core software unit 130 is used to drive the core imaging unit 110, collect data from the core imaging unit 110 and convert that data to OCT images, and store the OCT images in the storage medium 129. The core software unit 130 includes various add-on components and other rendering and analytical methods, such as Interferometric Synthetic Aperture Microscopy (ISAM) method to correct for the aberrations due to the shape of the Gaussian beam, which is discussed in further detail in Ralston T S, Marks D L, Carney P S, Boppart S A. Interferometric synthetic aperture microscopy. Nature Physics, 3(2):129-134, 2007, all of which is incorporated by reference herein. ISAM is also further discussed herein. The core software unit 130 also includes classification algorithms 180 based on the scattering profiles of individual axial scan data.

In one embodiment, the classification algorithms 180 are used to classify structures within the ear using a device 400, as discussed herein. As our understanding of OCT data from the ear increases, new classification algorithms 180 can be developed to not only better visualize and render the data, but to also automate the classification process. Intelligently designed software can differentiate between normal and diseased ears. In one embodiment, the classification algorithms 180 are used to detect the presence of biofilms in the middle ear. It has been discovered that the presence of a biofilm on the inner surface of the tympanic membrane will increase the effective optical pathlength, and the optical scattering will reveal a thicker, more irregular membrane, compared to the thin, smooth membrane of a normal ear. Using this fact, the classification algorithms 180 can be tailored to detect the presence of biofilms in the middle ear.

Classification algorithms 180 specific to the ear pathology can be used to automatically determine, in the case of biofilm detection, the thickness and surface features of the tympanic membrane with and without a biofilm present. Sufficient data can be used to generate statistical averages and probabilities. For simplified clinical use, few parameters may be available to the clinical user, and may only include the tympanic membrane thickness and likelihood of a biofilm being present, based on age-matched control measurements.

Figure 11A:
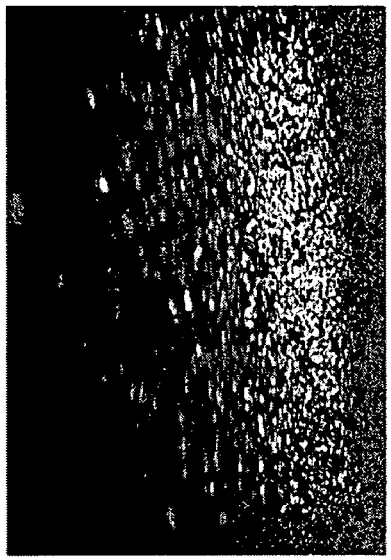
FIG. 11A depicts 3-D OCT image taken with a lab-bench setup of a tissue phantom with a uniform distribution of scatterers. The image shown is a corrected image after an ISAM algorithm is applied to the image, the scatterers that are at the top and bottom of the image (on the edges of the focal volume of the Gaussian beam) have been corrected to more accurately depict the true size and shape of the scatterers.
Figure 11C:
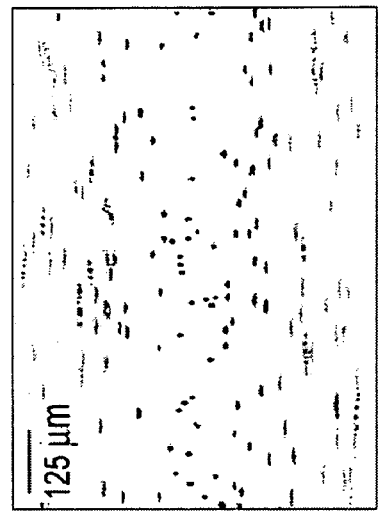
FIG. 11C depicts 3-D OCT image taken with a lab-bench setup of a tissue phantom with a uniform distribution of scatterers. The image shown is a non-corrected image where the point scatterers have become blurred rendering them indistinguishable.
Figure 11B:
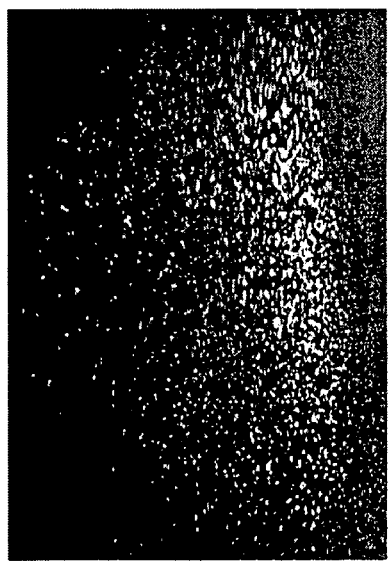
FIG. 11B depicts a 2-D OCT cross section of the image in FIG. 11A.
Figure 11D:
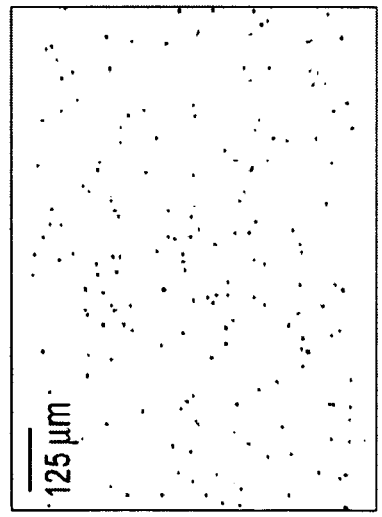
FIG. 11D depicts a 2-D OCT cross section of the image in FIG. 11C.

In addition to the automated classification algorithms 180, other post-processing methods, such as ISAM, can be employed to further enhance the OCT images, better visualize biofilms, or improving the quality of the raw data prior to the application of automated classification methods. By modeling the Gaussian properties of the light beam, using ISAM one can correct for the aberrations in the reconstructed image due to the Gaussian shape of the OCT beam. FIGS. 11C and 11D show an OCT image taken by the OCT system 100 before ISAM correction is applied and FIGS. 11A and 11B show an OCT image taken by the OCT system 100 after ISAM correction is applied. As one can see, the images in FIGS. 11A and 11B show more clarity and less blur than the images in FIGS. 11C and 11D.

In one embodiment, the core software unit 130 performs ISAM on the OCT data in real-time during a procedure, such as surgery. In this manner, the OCT system 100 can not only image tissue and generate OCT data in real-time, but can also provide a clearer image from the OCT data using ISAM. ISAM can therefore be used to enhance the OCT image in real-time and help guide a user, such as a doctor, during a procedure. In another embodiment, referred to herein as an ISAM guided procedure, ISAM can also be used without OCT in real-time during a procedure to enhance images from data received generated by other imaging techniques. Using ISAM in real-time during a procedure to enhance an image would allow a doctor to see items with the image, such as biofilms, with added clarity.

The core software unit 130 is used to quickly process and interpret the data from the core imaging unit 110 in real-time. The core software unit 130 of the OCT system 100 is can be written using commercially available software such as (National Instruments' LabView, and Mathworks' Matlab), or custom non-commercial software. LabView is primarily used to design the graphical user interface (GUI) and to interface with the various drivers to control the hardware components of the OCT system 100 and likewise to interface with the various processing algorithms written in Matlab or C++ or other packages.

Figure 5A:
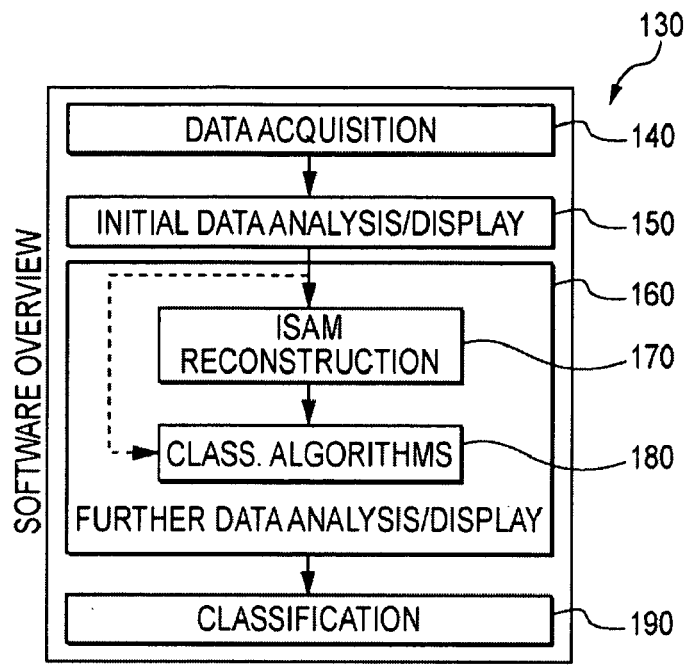
FIG. 5A depicts a flow diagram of a core software package which interfaces with an OCT engine of an OCT system.

The core software unit 130 is broken down into three main components, a data acquisition unit 140, an initial data analysis and display unit 150, and a further data analysis and display unit 160, as shown in FIG. 5A. Implementations of the core software unit 130, the data acquisition unit 140, the initial data analysis and display unit 150, and the further data analysis and display unit 160 each may include computer readable program code. These algorithms, devices and systems may be implemented together or independently. Such code may be stored on a processor, a memory device or on any other computer readable storage medium. The program code may be encoded in a computer readable electronic or optical signal. The code may be object code or any other code describing or controlling the functionality described in this application. The computer readable storage medium may be a magnetic storage disk such as a floppy disk; an optical disk such as a CD-ROM; semiconductor memory or any other physical object storing program code or associated data. A computer readable medium may include a computer program product including the computer readable program code.

FIGS. 5A, 5B, 5C, and 6 represent a flow chart of an example of a computer program product called the core software unit 130, which includes computer readable program code, for quickly processing and interpreting the data from the core imaging unit 110 in real-time. The core software unit 130 begins at 140 by acquiring data obtained by the core imaging unit 110. The data is then sent for initial data analysis and display at 150 upon which the data is taken and converted into an image. Upon forming an image, the image data is then sent for further data analysis and display at 160 upon which the data is run through an ISAM method at 170 to correct for the aberrations due to the shape of the Gaussian beam. Then the data is run through a set of classification algorithms 180 which look for certain optical properties in the image data and based upon those optical properties, the tissue shown by the image data is classified at 190.

Figure 5B:
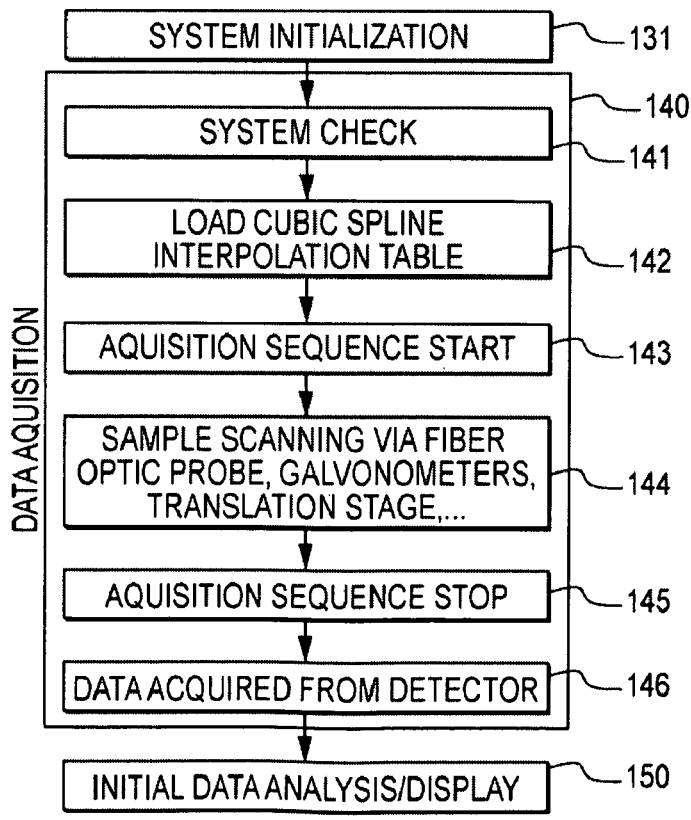
FIG. 5B depicts a flow diagram outlining the basic processes involved in OCT Data Acquisition.

FIG. 5B is a flow chart representation of a first portion of the core software unit 130. During operation, upon activating the core software unit 130, the core software unit 130 runs through a system initialization process at 131, wherein the core software unit 130 begins running on the computer hardware. Upon performing the system initialization process at 131, the core software unit 130 begins a data acquisition process at 140 by acquiring data obtained by the core imaging unit 110. First a system check 141 is performed to determine if the hardware is functioning properly. Upon performing the system check 141, a load cubic spline interpolation table is loaded at 142 and a data acquisition sequence is begun at 143. The load cubic spline interpolation table at 142 is a resampling method that is used to correct for the nonlinear optical aberrations along with any dispersion compensation that is not achieved in the hardware between the two arms. Upon initiating a data acquisition sequence at 143, sample scanning is then conducted using a device 120, such as a fiber based device 126. Once scanning is done, data acquisition ceases at 145 and data is then acquired from the detector or device 120 at 146 and the data acquisition process 140 is ended and an initial data analysis and display process is started at 150.

Figure 5C:
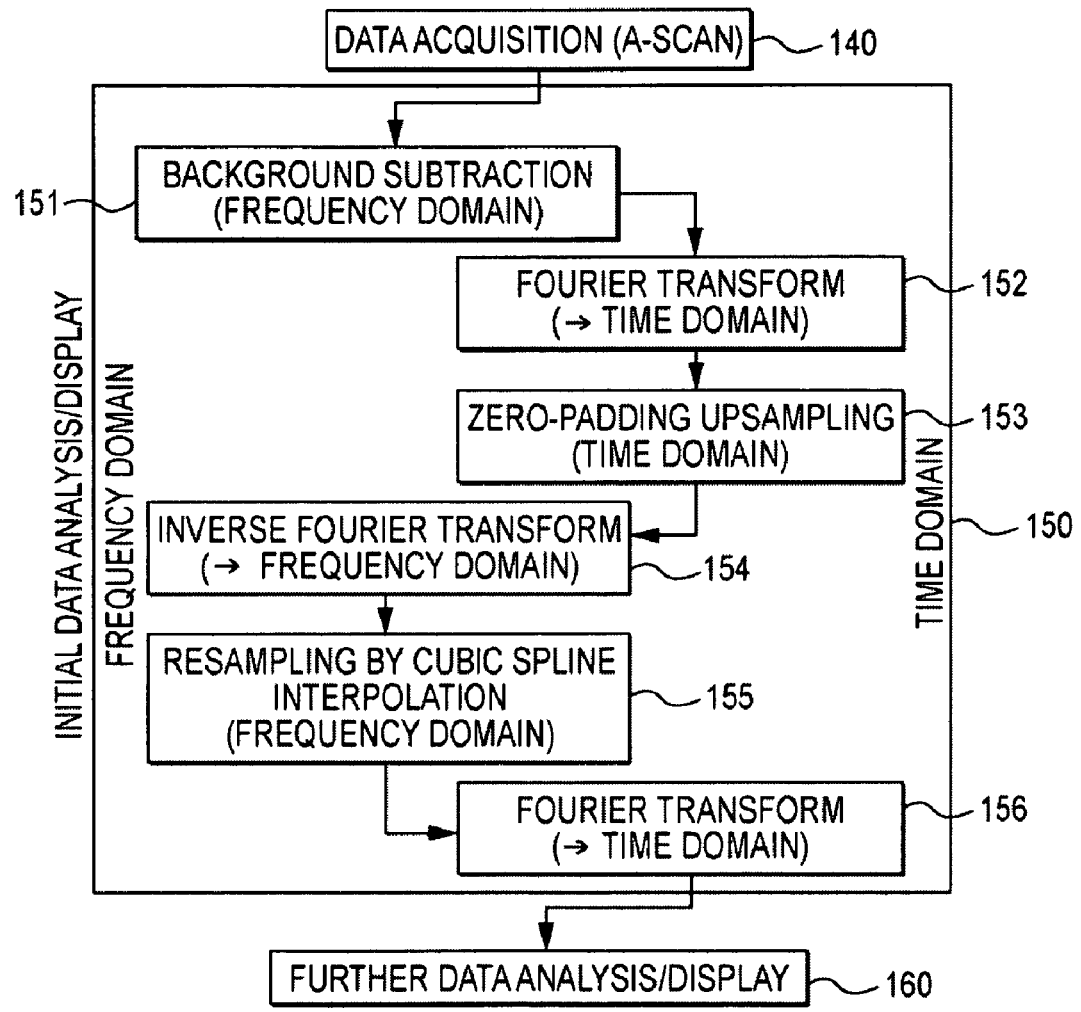
FIG. 5C depicts a flow diagram outlining the basic processes involved in Initial Data Analysis and Display of acquired OCT data.

As shown in FIG. 5C, data which is acquired from the data acquisition process 140 is sent to the initial data analysis and display process 150. The initial data analysis and display unit 150 processes the raw data acquired from the core imaging unit 110 into a traditional OCT image including some resampling methods to correct for dispersion and other non-linear optical aberrations. First, a background subtraction is performed on the data in the frequency domain at 151. The background subtraction 151 requires that a background image be taken by blocking the sample arm. In this way, the background image is the image of the reference arm signal (this is essentially a power spectrum without the interference overlaid on top of it), and is what is subtracted from the interference signal collected at the detector. Upon performing a background subtraction at 151, a Fourier Transform is performed on the data in the time domain at 152 and a zero-padding upsampling operation is performed on the data at 153. The zero-padding upsampling operation 153 adds a bunch of zeros in the time-domain data. This process increases the "number" of pixels and shifts the "original" useful data into a regime where the cubic spline interpolation works best. Then an inverse Fourier Transform operation is performed on the data in the frequency domain at 154 and a resampling using cubic spline interpolation is performed on the data in the frequency domain at 155. Finally a Fourier transform is performed on the data in the time domain at 156. The Fourier transform is performed at 156 to correct for nonlinear optical aberrations in the hardware. These aberrations can either be corrected for in the hardware optical components or in the software. Upon performing the initial data analysis and display process 150 on the data, the data is sent to a further data analysis and display process which is started at 160.

Figure 6:
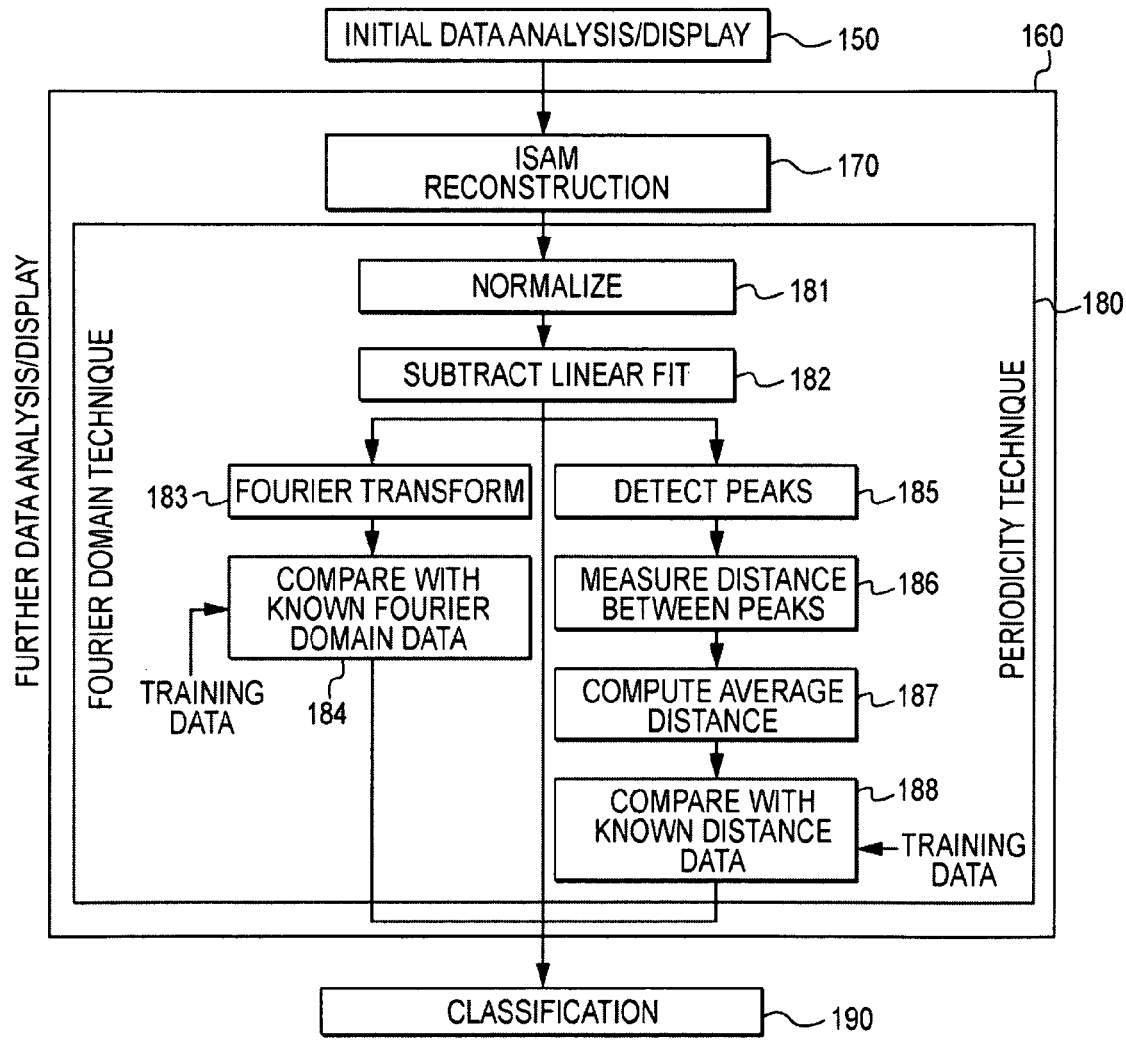
FIG. 6 depicts a flow diagram outlining the basic processes involved in Further Data Analysis and Display of acquired OCT data.
Figure 8:
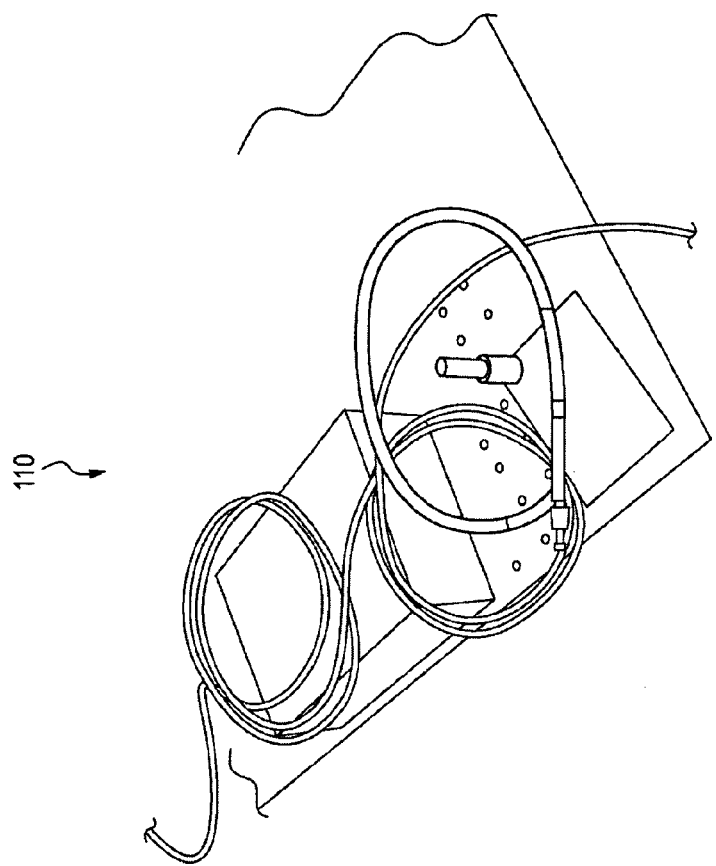
FIG. 8 depicts a device for imaging the middle ear using optical coherence tomography.
Figure 7:
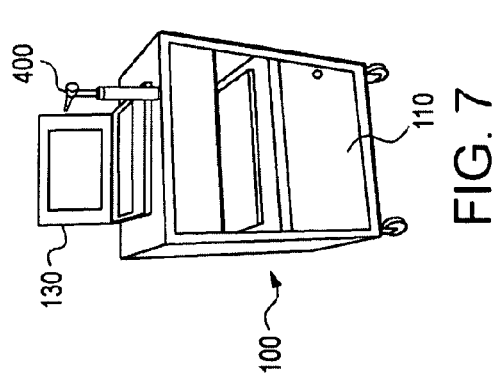
FIG. 7 depicts a device for imaging the middle ear using optical coherence tomography.
Figure 9:
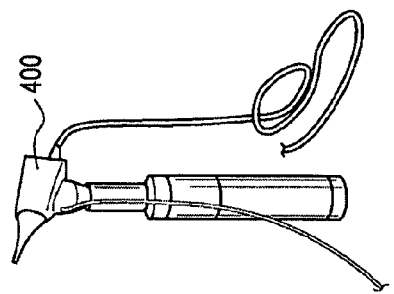
FIG. 9 depicts a modified otoscope used as a device for imaging the middle ear using optical coherence tomography.
Figure 10:
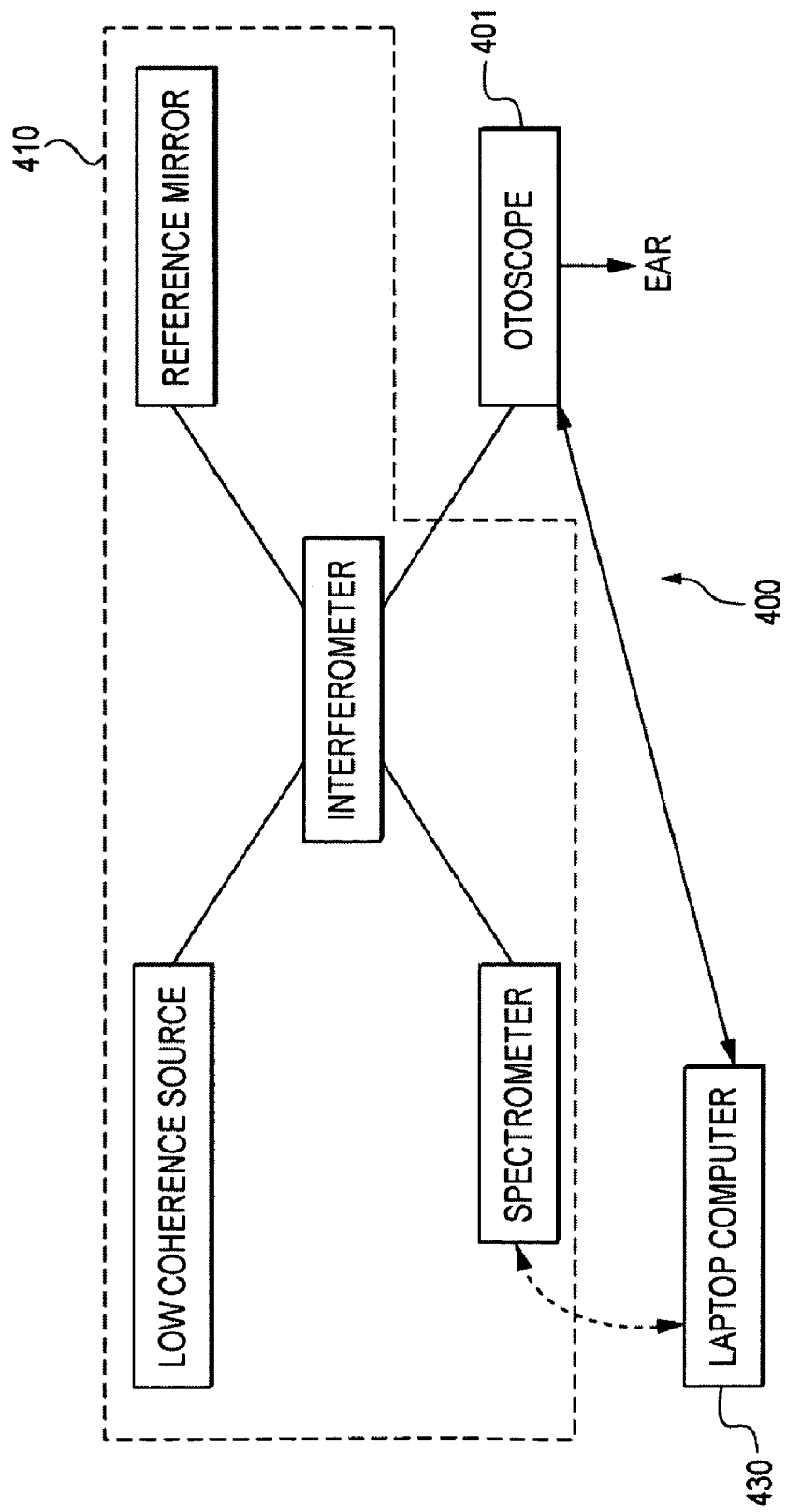
FIG. 10 depicts a schematic of a device for imaging the middle ear using optical coherence tomography.

As shown in FIG. 6, upon forming an image, the image data is then sent for further data analysis and display at 160 upon which the data is run through an ISAM method at 170 to correct for the aberrations due to the shape of the Gaussian beam. More information on the ISAM method is provided in U.S. patent application Ser. No. 60/819,593 filed on Jul. 10, 2006 entitled Interferometric Synthetic Aperture Microscopy (ISAM) Imaging Algorithm, U.S. patent application Ser. No. 11/775,572 filed on Jul. 10, 2007 entitled Interferometric Synthetic Aperture Microscopy (ISAM) Imaging Algorithm, and PCT application No. PCT/US2007/73146 filed Jul. 10, 2007.

Upon running the data through the ISAM method at 170, the data is run through a set of classification algorithms 180 which analyze the data and look for certain optical properties in the image data and based upon those optical properties, the type of tissue being imaged is then classified. For example, tissue being imaged can be classified as cancerous or non-cancerous, based upon the analysis done by the classification algorithms 180. In one embodiment, classification algorithms 180 include the processes illustrated in FIG. 6, however, other processes may be used to classify the data.

The classification algorithms 180 can be programmed to use various optical properties which can be derived from the OCT data, such as the scattering profile periodicity or the scattering profile frequency response, in order to classify tissue. One optical property which can be used is a refractive index measurement which provides a measurement of the pathlength between two objects along an optical path traversed by the radiation. The refractive index of the tissue may be calculated by Equation 1:

$$n = L/d, \qquad \text{EQ. 1}$$

where n is the refractive index, L is the physical distance between two objects, and d is the measured pathlength between the two objects. The device may also include one or more other devices for measuring the refractive index or other optical properties besides the refractive index.

In addition to refractive index, the classification algorithms 180 can be programmed to use other optical properties in order to classify tissue. One example of another optical property is the attenuation coefficient, which is a mathematical parameter governing the change in radiation intensity resulting from propagation through a medium. For a device having a refractive index measurement assembly containing an object, such as a reflective surface or an optical fiber, at a fixed physical distance from the radiation source, the attenuation coefficient may be calculated by Equation 2:

$$\sigma = -\ln(I/I_o)/L, \qquad \text{EQ. 2}$$

where σ is the attenuation coefficient, I is the intensity of the radiation measured at the object in the tissue, $I_o$ is the intensity of the radiation at the object in a vacuum, and L is the is the physical distance between the object and the radiation source. The attenuation coefficient may also be calculated using an interferogram generated from radiation at another region within the tissue. See, for example, Faber, D. J. et al., "Quantitative measurement of attenuation coefficients of weakly scattering media using optical coherence tomography", *Optics Express,* 12(19), 4353-4365 (2004).

Another example of another optical property is the scattering profile, which is a measure of the intensity of radiation reflected or backscattered from the tissue as a function of depth within the tissue. This may be especially useful to identify boundaries between different types of tissues. The scattering profile is analogous to an optical coherence tomography (OCT) axial-scan, in which the tissue is scanned along the depth dimension (axially) as opposed to an OCT b-scan, which scans in two dimensions (both axially and laterally). See, for example, Fujimoto, J. G. et al., "Optical Coherence Tomography: An Emerging Technology for Biomedical Imaging and Optical Biopsy", Neoplasia, 2(1-2), 9-25 (2000). See also Zysk, A. M. et al., "Computational methods for analysis of human breast tumor tissue in optical coherence tomography images", Journal of Biomedical Optics, 11(5), 054015-1 to 054015-7, 2006.

Another example of another optical property is the scattering coefficient, which is a mathematical parameter governing the change in radiation intensity due to scattering as a result of propagation through a medium. See, for example, Levitz, D. et al., "Determination of optical scattering properties of highly-scattering media in optical coherence tomography images", Optics Express, 12(2), 249-259 (2004).

Another example of another optical property is the anisotropy factor, which is a measure of the angle over which incoming radiation is scattered from a medium. See, for example, Levitz, D. et al., "Determination of optical scattering properties of highly-scattering media in optical coherence tomography images", Optics Express, 12(2), 249-259 (2004).

Another example of another optical property is the birefringence, which is a physical parameter governing the change in polarization of radiation due to propagation through a medium. See, for example, de Boer, J. F. et al., "Two-dimensional birefringence imaging in biological tissue by polarization-sensitive optical coherence tomography", Optics Letters, 25(2), 934-936 (1997).

Another example of another optical property is the spectral shift, which is a measure of the change in wavelength of the radiation due to propagation through a medium. See, for example, Morgner, U. et al., "Spectroscopic optical coherence tomography", Optics Letters, 25(2), 111-113 (2000).

Another example of another optical property is the texture, which is a measure of the local variations in brightness within a region of an image. See, for example, Gossage, K. W., "Texture analysis of optical coherence tomography images: feasibility for tissue classification", Journal of Biomedical Optics, 8(3), 570-575 (2003).

Another example of another optical property is the amount of movement or displacement of tissue, such as the tympanic membrane, in response to pressure from a device, such as a pneumatic otoscope. The amount of movement can be used to classify tissue or the presence of fluid, such as fluid or tissue within the middle ear, depending on how much movement is observed in relation to the amount of pressure exerted from the device.

Further examples of optical properties that may be determined in addition to refractive index include Doppler shifts; phase resolution, including phase-resolved Doppler measurements and phase-resolved spectroscopic measurements; light scattering parameters; and spectroscopic absorption. The optical properties listed above may be used in a variety of combinations with refractive index measurements. The refractive index and one or more other optical properties may be determined continuously; or a single optical property determination may provide a baseline analysis, which is then augmented by the determination of the refractive index and/or one or more other optical properties. Classification algorithms can be developed which utilize any of the optical properties listed above to classify the tissue seen in the image data.

As shown in FIG. 6, in one embodiment, as the data is run through the classification algorithms 180, the data is first normalized at 181 and then a subtract linear fit operation is performed at 182. The linear fit subtraction consists of first fitting OCT scan line data (on a log scale) to a straight line via any number of methods (e.g., a least-squares fitting) and then subtracting that line from the scan line data. Then the data can be run through either one of two techniques used to classify the data: 1) a Fourier domain technique; and 2) a periodicity technique. In one embodiment, the classification algorithms 180 use a Fourier domain technique to analyze and classify the image data received from the initial data analysis and display unit 150, as shown in FIG. 6. Upon having a subtract linear fit operation 182 being performed upon the image data, a Fourier transform is performed on the image data at 183 in order to convert the image data to frequency space. The image data is then compared with known Fourier domain data which was previously generated based on known tissue types at 184, and then classified based upon what tissue type the data most closely matches at 190.

In one embodiment, the classification algorithms 180 use a periodicity technique to analyze and classify the image data received from the initial data analysis and display unit 150, as shown in FIG. 6. Upon having a subtract linear fit operation 182 being performed upon the image data, a detect peak algorithm is run at 185 which analyzes and determines where peaks in the data occur. Then the distance between peaks is measured at 186. The average distance between the peaks is computed at 187 and then the average distance between the peaks is then compared at 188 with known distance data which was previously generated based on known tissue types at 184, and then the data is classified based upon what tissue type the data most closely matches at 190. Other techniques can be used to classify the data. For example, the slope of the line calculated for the linear fit subtraction may be used. Learning algorithms or neural networks could also be used to classify the data. By using the classification algorithms 180 described above, a user operating the OCT system 100 is able to quickly and accurately identify the type of tissue being imaged, such as whether the tissue is a biofilm, in real-time.

Figure 12:
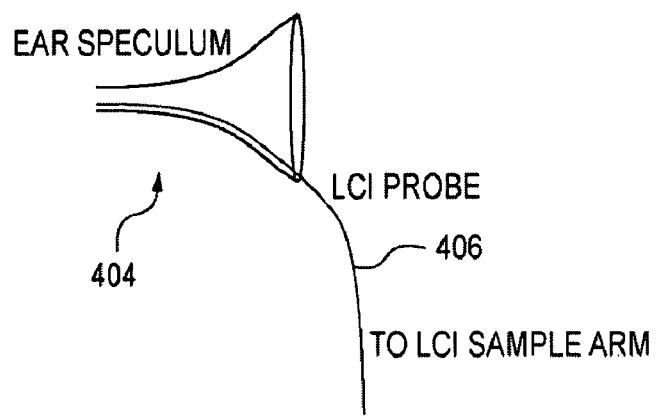
FIG. 12 depicts a schematic of a device for imaging the middle ear using optical coherence tomography.
Figure 13:
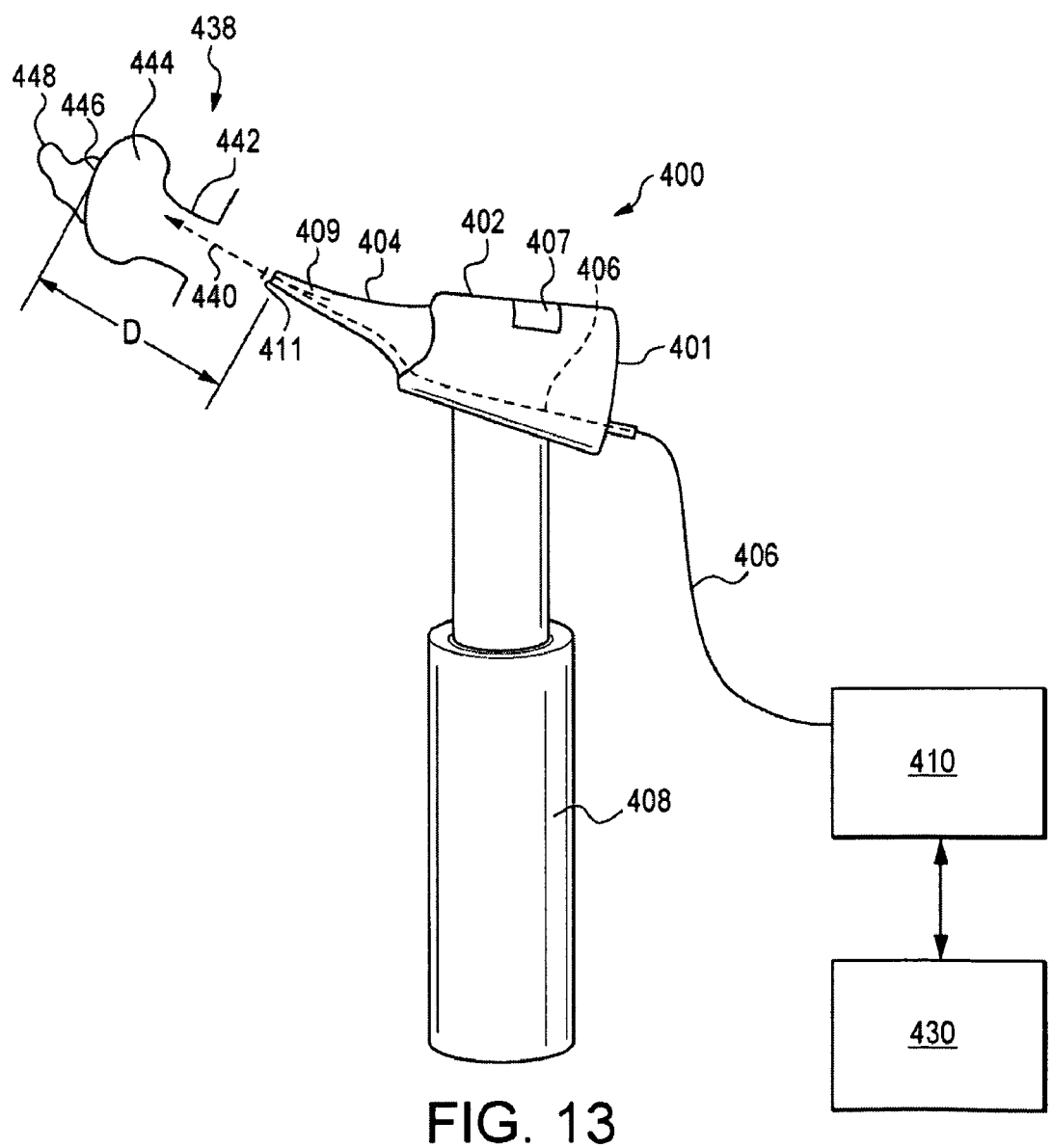
FIG. 13 depicts a device for imaging the middle ear using optical coherence tomography.

In one embodiment, a device 400 for imaging the ear using optical coherence tomography is provided which includes a core imaging unit 410 in communication with a core software unit 430, as shown in FIGS. 7, 8, 9, 10, 12, and 13. The core imaging unit 410 is analogous to the core imaging unit 110 described herein and the core software unit 430 is analogous to the core software unit 430 described herein. Preferably, the core imaging unit 410 is not only in communication with but also integrated within the device 400 so as to provide a compact portable instrument which allows straightforward clinical operation in an office-based setting. The core imaging unit 410 is in communication with the core software unit 430, as shown in FIG. 13. If the core imaging unit 410 is integrated within the device 400, then the core software unit can communicate directly with the device 400.

The device 400 can image visible structures (i.e. structures that can been seen with the naked eye) such, as the tympanic membrane, with enough accuracy to account for slight variations or movement in those structures. For example, device 400 can image variations or movement of the the tympanic membrane. Additionally, the device 400 can image structures which are not visible to the naked eye, such as middle ear structures behind the tympanic membrane in order to search for tissue, such as biofilms.

The device 400 includes any imaging device which can non-invasively image the middle ear, direct and receive light from the middle ear and send the received light to the core imaging unit 410. Preferably, the imaging device 400 also includes any device which can form a direct line of sight from the tympanic membrane to the outside of the ear, such as an ear speculum. The imaging device 400 includes things such as an otoscope 401, a pneumatic otoscope, ear plugs, ear speculums, and other such devices. In one embodiment, the otoscope 401 is a pneumatic otoscope, such as the MacroView™ otoscope manufactured by Welch Allyn Inc. of Skaneateles Falls, N.Y. or the BETA 200 otoscope manufactured by HEINE Optotechnik of Germany. The otoscope 401 includes a head unit 402 which is removably connected with an ear speculum 404 at one end and a handle 408 at another end. Preferably, the ear speculum 404 is manufactured from a polymer so as to be easily sterilized and disposable.

Preferably, the device 400 is adapted for selecting and analyzing tissue in the patient's middle ear. This means that the device is capable of non-invasively imaging inside the patient's ear canal and more specifically, non-invasively imaging the patient's middle ear. Preferably, at least a portion of the device is adapted for insertion into the patient's ear canal, allowing for non-invasive imaging of the patient's ear canal and or middle ear. In one embodiment, at least a portion of the device 400 has a diameter or width which does not exceed 1 cm and preferably does not exceed 0.5 cm, so that the device 400 can be inserted into an ear. However, since animal ears can be much larger than human ears, at least a portion of device 400 can be adapted for insertion into those ears and made much larger so as to fit within the ear canal of any animal, large or small.

In one embodiment, the device 400 includes a fiber based device 406 connected with or integrated with the otoscope 401, as shown in FIGS. 12 and 13. The fiber based device 406 includes any device which can act as a light guide and carry beams of light from one place to another. Preferably, the fiber based device 406 includes a fiber optic cable. When the otoscope 401 is placed near or within a patient's ear canal 442, light from the inner or middle-ear 444 carried through the fiber based device 406 to the core imaging unit 410. The fiber based device 406 is connected with the otoscope 401. In one embodiment, the fiber based device 406 delivers light into the optical system of the otoscope 401, and uses the existing or modified optics of the otoscope 401 to also direct a near-infrared beam to the middle-ear.

In one embodiment, the fiber based device is attached to an outside surface of the otoscope 401. In one embodiment, the fiber based device 406 is run through at least a portion of the otoscope 401, as shown in FIGS. 12 and 13. Preferably, the fiber based device 406 is run through at least portions of the head unit 402 and the ear speculum 404 of the otoscope 401. More preferably, the fiber based device 406 is run through the ear speculum 404 and positioned to receive light which enters the ear speculum 404. The ear speculum 404 provides mechanical support for the fiber based device 406 to perpendicularly approach an eardrum 446 to within about 5 mm, enabling non-invasive in-vivo ear diagnosis simultaneously with a regular otoscope exam.

The fiber based device 406 is preferably miniaturized to avoid blocking the field of the view of the otoscope 401, which is approximately 2.5 mm in diameter in some cases. Additionally, it is preferable that the fiber based device 406 be flexible enough to adapt to the curved shape of the ear speculum 404. Because of the dual role played by the fiber based device 406 as an optical source and receiver, the fiber based device 406 should produce a collimated beam or a weakly focused beam with a focus approximately the distance D between a tip 411 of the ear speculum 404 and the eardrum (~3-5 mm). A divergent beam will deteriorate the collection efficiency of the back-reflected optical signal. These requirements are achieved by fusion-splicing a gradient index (GRIN) fiber (which acts as a focusing element) on to the end of a single mode fiber (SMF) connected to the sample arm of the LCI interferometer. The GRIN fiber lens face is then polished to attain the appropriate angle and total GRIN fiber length.

In one embodiment, the device 400 is configured with a miniature video camera 409, and real-time video of the eardrum 446 from the device 400 is used to do a wide-field survey, as well as to select or track the location in the ear on the eardrum where an OCT measurement is acquired. The video camera 409 is preferably connected with the ear speculum 404.

In one embodiment, the fiber based device 406 includes a fiber-optic OCT probe which can be used to generate OCT signals, LCI signals, or both OCT and LCI signals. In one embodiment, the location in the inner or middle-ear 444 on an eardrum 446 where an OCT signal is acquired by the device 400 is illuminated, preferably by guiding light through the fiber based device 406 and onto the eardrum 446 in order to collect an OCT signal. The illumination is a low-power (1 mW) NIR beam which does not affect the regular operations of the otoscope 401. The back-reflected NIR beam from the middle-ear tissues is collected by the same fiber based device 406 and used to infer the depth-resolved structures of tissue within the ear 438, and specifically tissue within the inner or middle-ear 444.

In one embodiment, in order to obtain OCT data, more than one OCT signal is acquired. The OCT signals are acquired at high speeds (>250 Hz). This enables rapid collection of large depth-resolved datasets for analysis, as well as tracking of the movement of middle-ear structures (e.g., the eardrum) due to pneumatic operation of the otoscope 401, which can be monitored in real time. The simultaneous capture of a video image of the NIR beam on the eardrum, along with the depth-resolved OCT signals, enables correlation of suspect visual findings with depth-resolved measurements and the generation of OCT data.

In one embodiment, in order to obtain OCT data, an LCI signal is generated which retrieves a depth-resolved reflectance profile at the location of the probing beam and along an axial direction 440 of the fiber based device 406 (axis-scan). The resulting OCT data generated represents one-dimensional structural scattering information of the tissue being measured, such as inner or middle-ear tissue. Since the LCI signal in this case is fast, relative to small lateral movements between the ear speculum 404 and the ear 438, multiple axial-scans can be acquired rapidly, corresponding to a specific set of sampling data that can be analyzed by a computer using the core software unit 430 or reconstructed to produce a cross-section type of "image" associated with the continuous trace of these sampled regions. The resulting OCT data facilitates the detection of tissue structures including the eardrum 446, ossicles 448, and the presence of a biofilm. In one embodiment, a traditional spectral-domain LCI system can be used as the core imaging unit 410 in order to generate an LCI signal and obtain OCT data.

Upon obtaining the OCT data, the OCT data is then sent to the core software unit 430 where the OCT data is analyzed, processed and classified, as described herein. Specifically, the OCT data is analyzed to determine the patient's middle ear condition. This includes discriminating between chronic OM and non-chronic OM, determining if a biofilm is present, quantifying properties of the tympanic membrane, and to gain diagnostic information even if the ear drum 446 is visually opaque, as described in further detail herein. In one embodiment, the OCT data is analyzed to determine the patient's tympanic membrane or ear drum condition.

In one embodiment, the device 400 includes an indicator 407 which is used to indicate to a user the results of core software unit 430, such as what type of tissue had been imaged and other properties of that tissue, such as an image of that tissue. The indicator 407 includes any device which can communicate with a user and includes things such as a speaker, a screen, a light, and a vibrating or moving member. In this manner, the indicator 407 can signal to a user if a biofilm or other type of tissue is present or absent.

Figure 35:
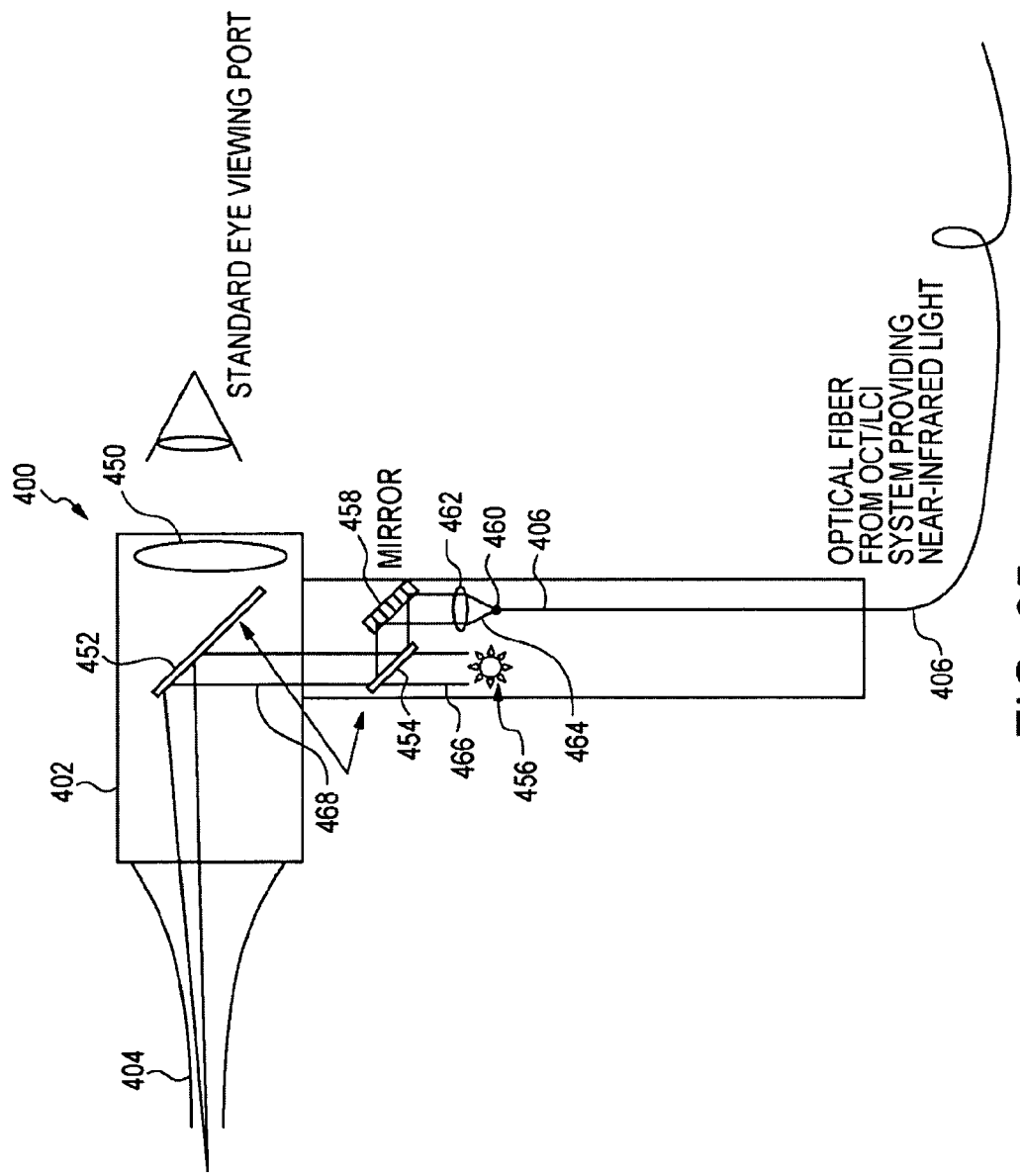
FIG. 35 depicts a modified otoscope used as a device for imaging the middle ear using optical coherence tomography.

In one embodiment, the device 400 includes a beam splitter 454, a light source 456, and a mirror 458, as shown in FIG. 35. The fiber based device 406 includes an end point 460 through which light 464 which travels from the core imaging unit 110 through the fiber based device 406 exits. Light 464 is preferably near-infrared light having a wavelength of between 650 nm to 1500 nm. The end point 460 is located in the device 400, and preferably in either the handle 408 or the head unit 402. The fiber based device 406 and the end point 460 are aimed at the mirror 458. Mirror 458 is any device which can reflect light. Preferably, a collimating or focusing lens 462 is located between the end point 460 and the mirror 458 so as to prevent light 464 which has exited the fiber based device 406 from spreading. Mirror 458 is positioned so as to receive and reflect light 464 to the beam splitter 454.

The beam splitter 454 can be any device which reflects some light and allows some light to pass through it, such as a reflective/transmitting beam splitter or a dichroic mirror. The beam splitter 454 is positioned so as to receive and reflect light 464 from the mirror 458 and to allow at least some light 466 emitted from the light source 456 to pass through the mirror 454. Light source 456 is preferably any conventional type of light source which may be found in an otoscope. Light source 456 therefore is preferably compact enough to fit in an otoscope and emits visible light, that is light with a wavelength of between 380 nm to 750 nm. Upon being reflected from the beam splitter, light 464 is combined with light 466 and directed out of the device 400 through an opening in the ear speculum 404 and eventually to ear tissue. In this manner, by including a beam splitter 454, a light source 456, and a mirror 458, device 400 is able to transmit as a combined beam of light, both light 466 generated from light source 456 and light 464 generated from core imaging unit 110, to ear tissue and obtain OCT data from that ear tissue. Additionally, by including a beam splitter 454, a light source 456, and a mirror 458, device 400 does not need to have the fiber based device 406 be connected with the head unit 402 or the ear speculum 404, allowing for a possibly more compact and more robust device 400.

In one embodiment, the device 400 includes a second beam splitter 452 in the head unit 402. The second beam splitter 452 is positioned so that ambient light from outside the device 400 which enters the device 400 at an eye viewing port 450, passes through the second beam splitter 452. The second beam splitter 452 is also positioned so that combined light 464 and 466 are combined with the ambient light and reflected from the second beam splitter 452 and directed out of the device 400 through an opening in the ear speculum 404 and eventually to ear tissue. In this manner, ambient light used by the user to view ear tissue, can be combined with light 464 and 466 so as to allow a more simple and direct optical path for the light traveling between the ear tissue and the device 400.

In order to determine if a biofilm is present, the core software unit 430 analyzes the OCT data received from the core imaging unit 410. A normal tympanic membrane should show as having a relatively constant and standard width on a depth-resolved LCI axial scan, for example. At multiple locations across the drum, this width should remain relatively constant. The normal ear has no fluid, and so scattering from the middle ear should be absent. An eardrum with a biofilm should be thicker than a normal eardrum, and have an irregular scattering signal from the back (inner) surface of the eardrum. If an effusion is present, there will be some scattering signal from this, and more scattering if the fluid is turbid or has an infection/bacteria present in the fluid. For a normal ear under pneumatic pressure, the drum should be smoothly displaced, and over several hundred microns. In an ear with biofilms or a thick effusion, this displacement will be retarded under pressure, and may even be absent. These are methods for identifying biofilms/infectious pathologies.

The device 400 can be upgraded from an LCI to an OCT capable otoscope by introducing a transverse scanning mechanism to the fiber based device 406. This can be done by a number of lateral translation mechanisms (piezoelectric, electrostatic), or by rotating GRIN lens optical elements to produce forward-directed scans directed at the tympanic membrane. In another embodiment, the microoptics would contain a right-angle prism to direct the beam at a right-angle from the fiber, and the optics would rotate within a clear plastic sheath. In this latter mode, the fiber based device 406 behaves effectively like a catheter-endoscope. Although the complexity of the device 400 is increased, these upgrades can be a useful adjunctive tool when real cross-sectional images of the middle-ear (transverse scanning) 448 or of the ear canal (rotational scanning) 442 are required for advanced diagnostic purposes.

One application of the device 400 is to discriminate between chronic OM and non-chronic OM in order to avoid unnecessary medical or surgical interventions. OM (with or without effusion) is one of the most common pediatric infectious illness which affects as much as 50% of the pediatric population. It is usually of no concern except, however, if it becomes chronic. Chronic OM occurs at a much lower percentage than non-chronic OM, but can delay speech development and result in hearing loss in later life. Unfortunately, chronic and non-chronic OM produce similar otoscopic findings, as observed by a physician.

Recent clinical studies have established a one-to-one correspondence between chronic OM and the presence of biofilms (i.e., aggregated bacterial colony within an extracellular matrix) behind the tympanic membrane (i.e., eardrum) and within the middle ear (See L. Hall-Stoodley, F. Z. Hu; A. Gieseke, L. Nistico, D, Nguyen, J. Hayes, M. Forbes, D. P.

Greenberg, B. Dice, A. Burrows, P. A. Wackym, P. Stoodley, J. C. Post, G. D. Ehrlich, J. E. Kerschner, "Direct detection of bacterial biofilms on the middle-ear mucosa of children with chronic otitis media," JAMA. 296, 202-211, 2006). Thus, the presence of a biofilm can be treated as a "structural signature" of chronic OM. Due to its thin film (typically 10-100 µm), biofilms have little optical contrast when viewed with the human eye through an otoscope, and can rarely be distinguished from the surrounding ear tissues. In contrast, the present invention makes use of the discovery that biofilms can readily be detected and quantified by OCT through a mechanism analogous to how pulse-echo ultrasound locates material density boundaries within thick tissues, i.e., the coherence ranging mechanism.

A second application of the device 400 is to quantify properties of the tympanic membrane within the ear 438. The mobility of the tympanic membrane or eardrum 446 in response to the pressure changes inside the ear 438 (pneumatic pressure) is of important diagnostic value in pneumatic otoscopy. The retarded mobility indicates the presence of a fluid (effusion) in the middle-ear 444, which is diagnosed as OM with effusion (OME). However, the degree of mobility is usually graded in qualitative terms. The depth-resolved detection and range-finding ability of OCT easily quantifies this mobility, i.e., the extent of OME, as well as the optical scattering or turbidity of the effusion itself, within the middle-ear 444. The quantification is most useful when the buildup or clearance of the effusion must be monitored to study the pathological origin of OME and to evaluate corresponding treatments. As an example, the shape of the tympanic membrane or eardrum 446 can be used to differentiate acute OM (resulting in a bulging eardrum) from OME (resulting in a retracted eardrum position). Antibiotic treatment is efficient in the former case but inefficient in the latter case. The degree of bulging or retraction can be easily quantified by the device 400.

A third application of the device 400 is to gain diagnostic information even if the ear drum 446 is visually opaque. In many situations, the visibility of the tympanic membrane and middle-ear 444 contents is impaired (due to tympanic membrane perforation, vascularity, cholesteatoma, tympanosclerosis, etc.), which compromises the diagnostic ability of pneumatic otoscopy. While the visible light employed in pneumatic otoscopy cannot penetrate the eardrum 446 and visualization is only based on surface features, the near-infrared (NIR) light afforded by OCT has adequate penetration depth to access the middle-ear structures behind the eardrum 446. For example, the detection of a large amount of middle-ear effusion behind an opaque eardrum 446 can be diagnosed as OME rather than a disease associated with the eardrum 446 itself. The visible (surface features) and NIR (depth-resolved) tests used in conjunction provide a significant advantage to obtain more diagnostic information. Thus, the enhanced pneumatic otoscope with coherence ranging capability can be used as a powerful, portable, office-based, diagnostic, monitoring, and research tool to detect, diagnosis, monitor, and improve the understanding of ear pathology. This better understanding may extend the applications of the device 400 beyond those discussed above, and may lead to a cost-effective and efficient screening tool to identify patients in whom appropriate interventions must be initiated.

Preferably, when using the device 400, OCT data is collected over a wide field, or for several seconds of acquisition time, as a typical middle-ear cavity is one cubic centimeter in size. With such a high-resolution imaging modality and a large data set, there is a need to quickly process and interpret the data in real-time. The core software unit 430 is used to quickly process and interpret the data from the core imaging unit 410 in real-time.

The following examples are provided to illustrate one or more preferred embodiments of the invention. Numerous variations can be made to the following examples that lie within the scope of the invention.

EXAMPLES

Preliminary results have been obtained using lab-based OCT to image biofilms in controlled environments, such as within a flow-cell, as shown in FIGS. 14A, 14B, 14C, 15A, and 15B (See Xi C, Marks D L, Schlachter S, Luo W, Boppart S A. "High-resolution three-dimensional imaging of biofilm development using optical coherence tomography," J. Biomed. Opt. 11 (3):034001-1-134001-6, 2006). These results clearly showed the potential of scattering based optical measurements for the detection of biofilms. Two-dimensional and three-dimensional OCT images are shown in FIGS. 14A, 14B, 14C, 15A, and 15B. However, each 2-D image is composed of a series of adjacent 1-D LCI depth scans. Sufficient information exists in the 1-D depth scans to determine the thickness and optical properties of layered structures, such as the layered biofilm on the tympanic membrane.

Figure 14A:
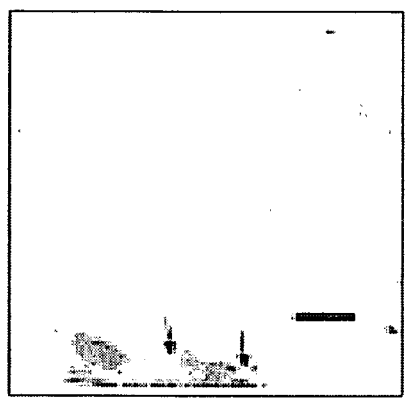
FIGS. 14A, 14B, and 14C depict OCT imaging of a 7-day *Pseudomonas aeruginosa* biofilm in a capillary tube of a flow cell. The dimension of the tube is 1 mm by 1 mm and the length of the biofilm is 2 mm.
Figure 14B:
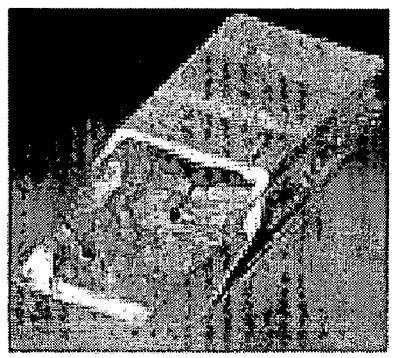
Figure 14C:
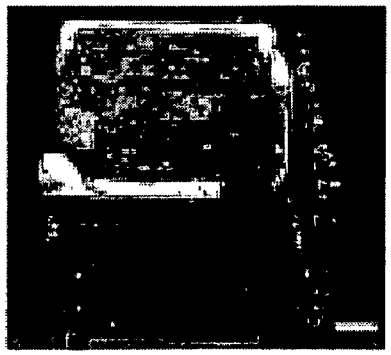
Figure 15A:
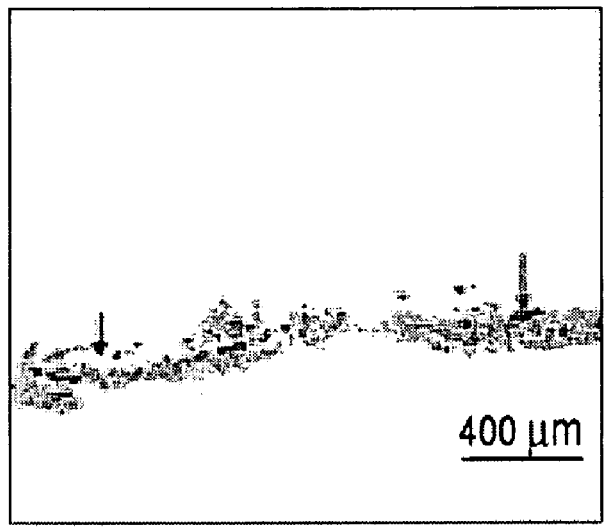
FIGS. 15A and 15B depict OCT imaging of a 3-day *Pseudomonas aeruginosa* biofilm developed at the interface of air and culturing media. The area scanned is 2 mm by 2 mm.
Figure 15B:
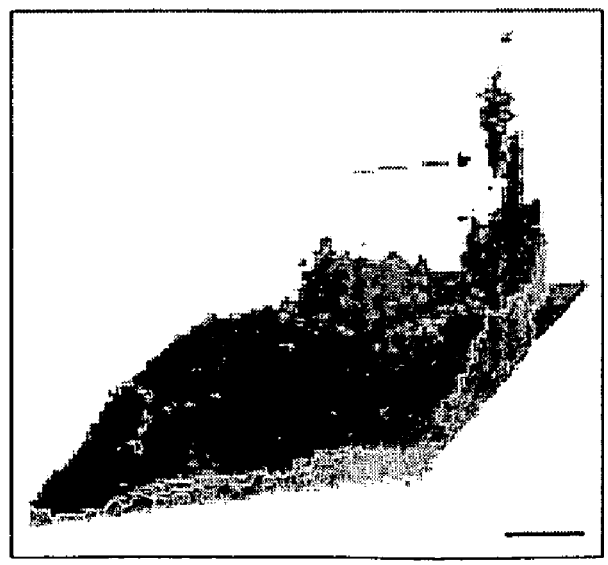
Figure 16A:
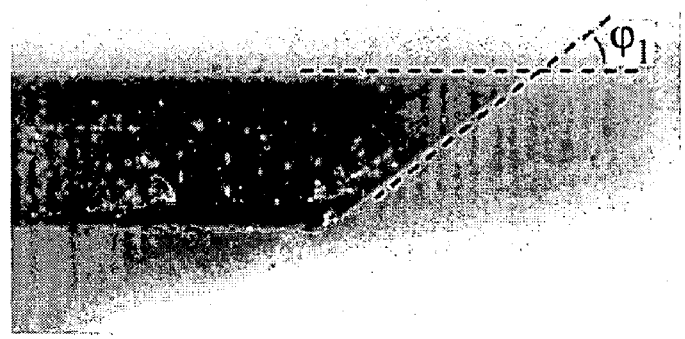
FIGS. 16A, 16B, 16C, and 16D depict light microscope images of a representative needle biopsy probe tip showing in FIG. 16A the angled cutting surface and in FIG. 16B the tip sealed with optical cement. The device drawing in FIG. 16C shows light propagation through a single mode (left) and gradient-index fibers (right), the optical cement used to secure them, and the cement-sample interface (arrow) where the beam exits.
Figure 16B:
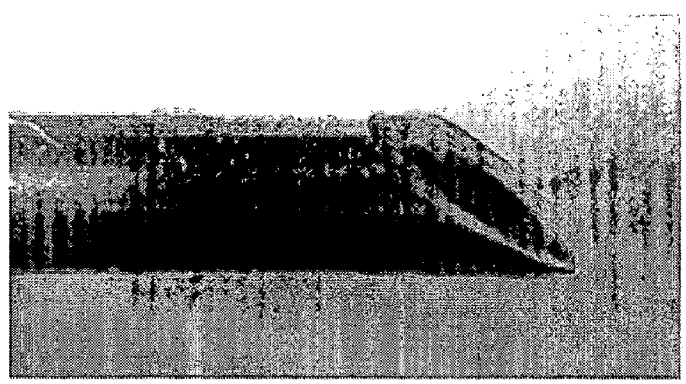
Figure 16C:
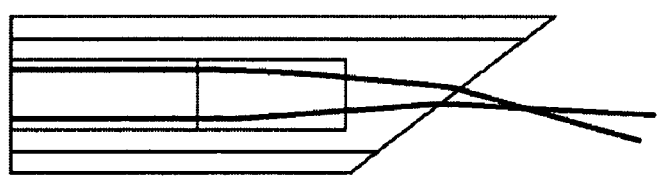
Figure 16D:
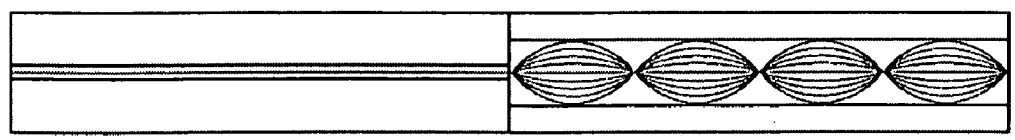

The biofilms associated with chronic OM consists of aggregated bacteria of *Streptococcus pneumoniae, Haemophilus influenzae, Moraxella catarrhalis,* or any combinations of the three. This biofilm is structurally similar to the biofilm of *Pseudomonas aeruginosa*, which can be easily produced in-vitro. The biofilm of *Pseudomonas aeruginosa* can be developed in a flow cell by continuously circulating a bacterium-contained broth medium. A traditional time-domain OCT was used to monitor the growth dynamics of the biofilm (See Xi C, Marks D L, Schlachter S, Luo W, Boppart S A. "High-resolution three-dimensional imaging of biofilm development using optical coherence tomography," J. Biomed. Opt. 11(3):034001-1-134001-6, 2006). OCT images and 3-D volumes are shown in FIGS. 14A, 14B, 14C, which reveal dark scattering features on the top and bottom of the flow cell. In comparison, the initial images of the flow cell reveal no visible dark features. These features are attributed to the biofilm which has sufficient optical contrast relative to the surrounding broth medium and the glass flow cell wall. Since the biofilms associated with chronic OM have similar optical contrast relative to the middle-ear effusion and the tympanic membrane, it is expected that the biofilms can be detected in vivo using LCI/OCT.

The improved performance of the spectral-domain operation over the time-domain operation should further assist this detection by providing improved signal-to-noise at faster acquisition rates. Additionally, it is expected that the presence of an effusion in OME will produce a weakly-scattering but readily identified signal from within the middle-ear chamber. In OME, the middle-ear chamber is filled with semitransparent to high-scattering fluid, and the LCI/OCT data collected will provide optical characterization of the fluid type present. Additional studies will be required to correct these scattering signals to specific fluid types found in vivo.

As shown in FIGS. 7, 8, 9, 10, and 12, a portable prototype device 400 has been constructed, and is designed for clinical implementation for feasibility studies. The device 400 uses a compact superluminescent diode light source operating at 940 nm center wavelength with a measured bandwidth of 74 nm. This provides an axial resolution of 5.7 microns in air, or 4 microns in biological tissue. This source is used in a spectral-domain LCI system that utilizes a compact spectrometer, manufactured by OceanOptics of Dunedin, Fla., to capture spectra at 250 Hz (depth-scan acquisition rate). The sample arm consists of the fiber probe and micro-optics integrated with a commercially-available video pneumatic otoscope, manufactured by Welch-Allyn of Skaneateles Falls, N.Y. The micro-optical element at the tip of the sample-arm single-mode fiber probe consists of a Gradient Index (GRIN) fiber fused on the end of the single-mode fiber to act as a collimating/focusing element. The GRIN fiber can alter the focusing properties of the light exiting the single-mode fiber, depending on its length. To obtain the proper optical collimating/focusing properties distal to this fiber based probe, a commercial fiber polisher is used to remove GRIN fiber material from the distal end, in a controlled manner. By doing so, the collimating or focusing parameters can be adjusted as needed.

Figure 17A:
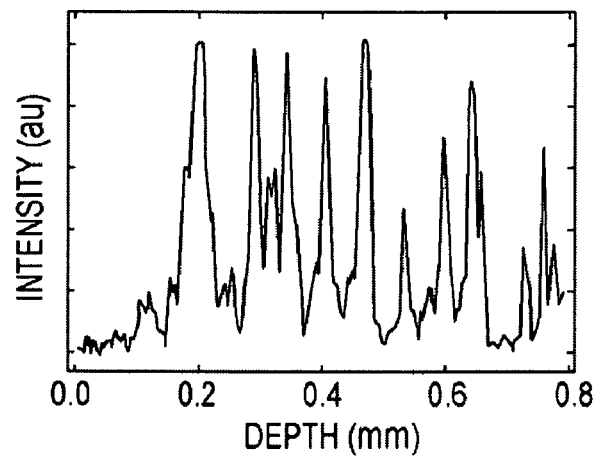
FIG. 17 depicts OCT axial scan data from adipose tissue (left), invasive ductal carcinoma tumor tissue (middle), and stroma tissue (right).
Figure 17B:
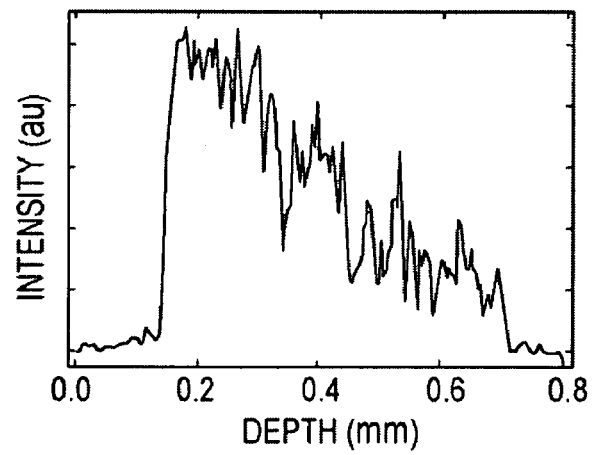
Figure 17C:
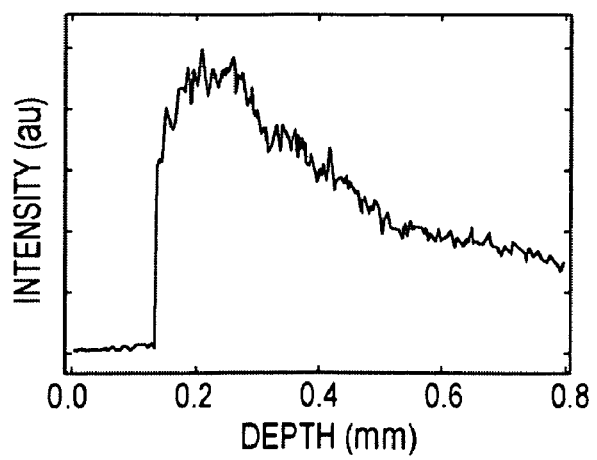

In some diagnostic situations, a device 400 which generates LCI signals is advantageous over a device 400 which generates OCT signals due to its simplicity of the instrumentation. A device 400 which generates LCI signals collects single columns (i.e., one-dimensional) of depth-resolved structural information. Applicants have discovered that these one-dimensional data alone can be useful to extract diagnostic information. Applicants have conducted in vitro studies on human breast tissues using needle-biopsy fiber based devices 406. The LCI axial scan data are plotted in FIG. 17 for adipose tissue, stroma tissue, and invasive ductal carcinoma tumor tissue.

Due to the difference of these profiles, a computational method has been developed to automatically classify these tissues with good sensitivity and specificity (See A. M. Zysk, and S. A. Boppart "Computational methods for analysis of human breast tumor tissue in optical coherence tomography images," J. Biomedical Optics. 11, 054015, 2006). Similar methods can be applied to a device 400 which generates LCI or OCT signals to classify the middle-ear structures, primarily the tympanic membrane, and the presence, thickness, irregularity, and optical properties of any biofilm, which are in turn correlated with disease states.

The OCT system 100 is being presented as a highly modular system that can interface with various devices to widen its range of potential applications as well as interfacing with newer visualization algorithms and classification methods presented here. The device 400, provides doctors with a system that not only can provide quantitative data on the status of ear health and disease, is non-invasive, and can also provide repeated monitoring for following disease progression or regression following medical treatments. The present invention permits not only the standard qualitative visualization and video capture of the ear anatomy and pathology, but also simultaneous OCT quantification of tympanic membrane position and integrity, middle-ear anatomy, and the presence and classification of middle ear effusions.

Description of ISAM

The following detailed description may be more fully understood by reference to Ralston et al., Inverse Scattering for Optical Coherence Tomography, J. Opt. Soc. Am. A, vol. 23, pp. 1027-37 (May, 2006), which is appended hereto, and incorporated herein by reference.

Figure 18:
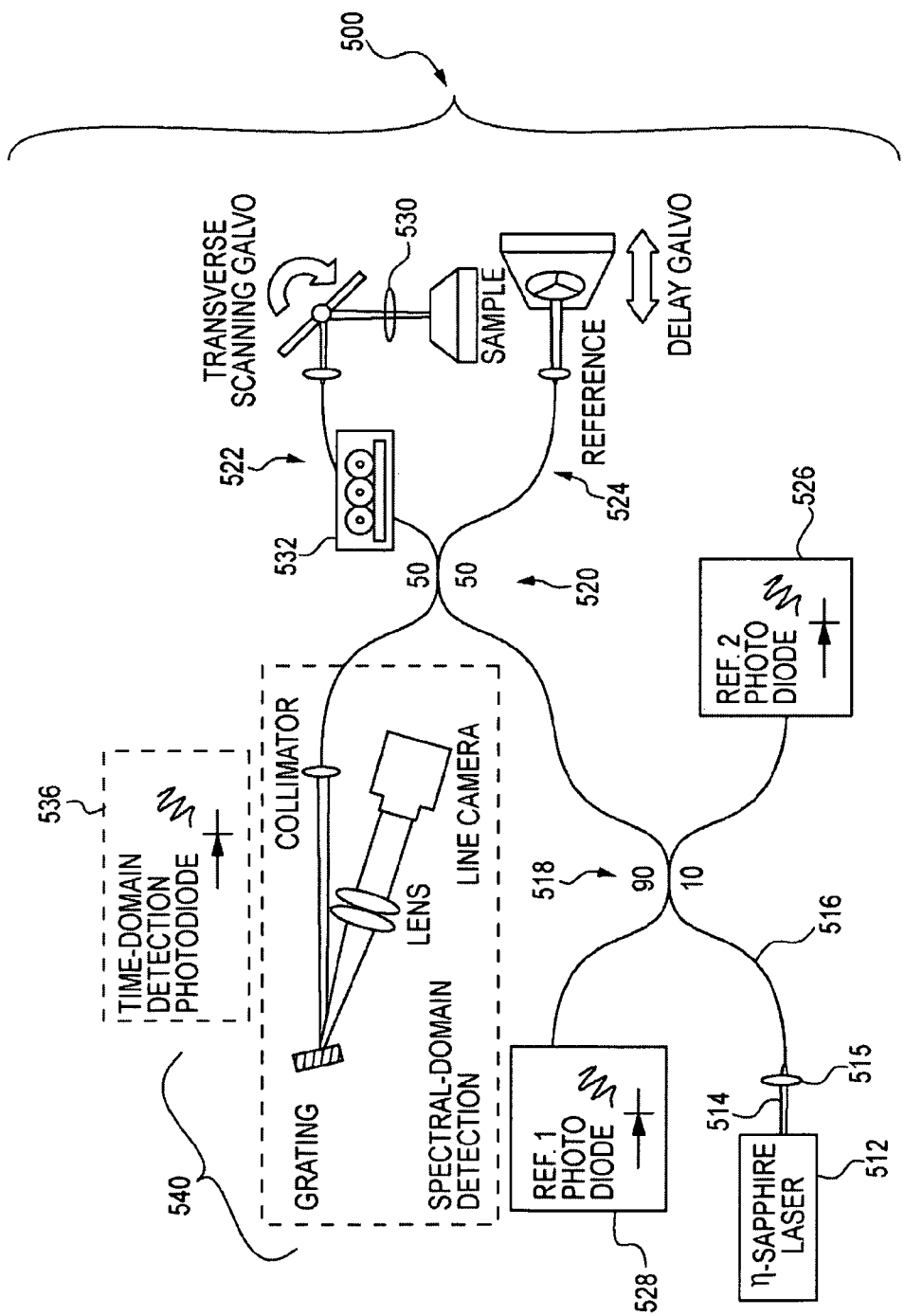
FIG. 18 is an exemplary schematic depiction of an optical coherence tomography system in its time-domain and spectral-domain variants.

FIG. 18 shows an example of an OCT system, designated generally by numeral 500, including options to detect the cross-correlation signal in either the spectral domain or the time domain. This particular OCT system uses a coherent light source 512, such as a neodymium:vanadate (Nd:YVO4) pumped titanium:sapphire laser. In the exemplary embodiment depicted, a center wavelength of 800 nm and an average bandwidth of 100 nm yields an axial resolution of ~2 µm in tissue. The beam 514 is launched, via coupling optics 515, into a fiber-optic cable 516 and connected to a pair of fiber-optic beam splitters 518, 520 (Gould Fiber Optics, Inc., Millersville, Md.). The interferometer employs a single-mode 50/50 fiber optic splitter 520 that delivers and couples the signals to and from the sample arm 522 and the galvanometer-based reference arm 524. The 90/10 beam splitter 518 serves the purpose of producing a reference spectrum for source noise reduction in the balanced photodetector. This setup can make use of both the single photodetector and the high-speed dual balanced photodetectors 526 and 528. In the sample arm, interchangeable achromatic lenses 30, from 9 mm to 40 mm, can be used to focus from 10 mW to 30 mW of light down to corresponding spot size (determined by transverse resolution). Polarization paddles 532 in the sample arm are able to change the polarization incident upon the sample to achieve maximum interference.

A time-domain system is characterized by capturing axial scans while a reference arm 524 varies the path length in relation to the sample arm 522. There are several designs of varying the path length in the reference arm. In certain embodiments, reference arms may include a standard spatial domain delay, or a rapid scanning optical delay (RSOD) which employs a spatial Fourier shift to create a delay. Typically, a single or dual-balanced photodetector 36 is used to capture interference data.

A spectral-domain system is characterized by capturing the spectrum of a light source and inferring the spatial axial susceptibility. Susceptibility describes, in theoretical terms, the dielectric properties of a material that give rise to scattering and thus to the representation ordinarily considered to constitute an image. There are several ways to detect the spectrum including employing a frequency swept laser and detection with a single photodetector, or a broadband laser and detection using an imaging grating spectrometer 40 so that all frequencies are detected simultaneously.

In order to elucidate the present invention, a theory of inverse scattering is presented that has been developed for optical coherence tomography (OCT) and that is used to resolve three-dimensional object structure, taking into account the finite beam width and focusing. While the invention is described herein in optical terms, it is to be understood that the invention is not so limited, and that the teachings provided herein are equally applicable to any radiation, whether acoustic or of other particles, massive or otherwise, that may be characterized in terms of wave propagation.

By using the invention, transverse and axial resolution produced by conventional OCT imaging inside the confocal volume can be achieved outside of the confocal volume. Explicitly, experiments show that scatterers can be resolved outside of the confocal volume with resolution comparable to that achievable inside the confocal volume. Numerical simulations and experimental results demonstrate the effectiveness of this technique. When the algorithm is applied to experimentally-acquired OCT data, the transverse and axial resolutions outside of the confocal parameter are improved, extending the apparent confocal parameter range. These results further improve the high-resolution cross-sectional imaging capabilities of OCT.

Figures 19A, 19B:
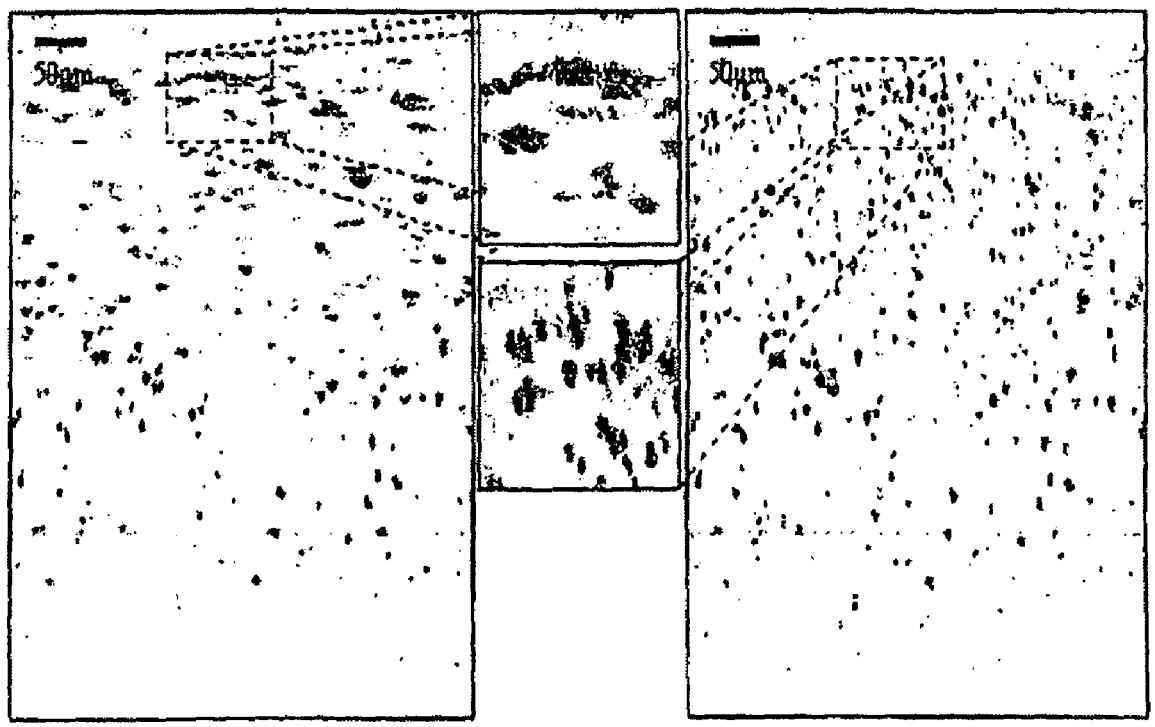
FIG. 19(*a*) is an example of OCT data derived from microparticles embedded in a tissue phantom outside of the focus, while FIG. 19(*b*) is an ISAM reconstruction of the data.

To illustrate the problem in OCT that is solved with ISAM, a sample is designed and imaged, which clearly shows the effect of the probing beam. A tissue phantom, a collection of titanium dioxide scatterers having a mean diameter of 1 µm suspended in silicone, was imaged with a spectral-domain OCT (SD-OCT) system. FIG. 19(a) displays the OCT data with no beam consideration. The 2D ISAM reconstructed image of an area of 500 µm (transverse) by 1000 µm (axial) is depicted in FIG. 19(b), where the bandwidth is 100 nm, the focal length of the lens is 15 mm, the spot size is 11 μm, and the confocal parameter is 996 μm. The image resolution of point scatterers outside of the confocal region for the original experimental image data is not constant, but for the reconstruction, the resolution is relatively constant along the entire image with only amplitude variations. The interference between the light scattered from a group of adjacent particles (boxed) is evident in the original image (top magnified). Methods in accordance with the present invention properly rephase the signal from scatterers to produce a well-resolved image (bottom magnified).

The sample imaged in FIG. 19 consists of a uniform number of scatterers, yet when looking at the reconstruction the number of scatters outside of the confocal region seems to increase. The 2D equivalent of the algorithm resolves only a perpendicular projection of the 3D data set. The imaging beam has a wider contour outside of the confocal region, and thus the beam is incident upon a larger volume illuminating more scatterers.

ISAM fundamentally relies on the solution of the inverse scattering problem, S=Kη, where K is a linear operator which transforms the collected signal S to the object's spatial susceptibility η. (The dimensionalities of S and η are discussed below.) In some geometries, K can be diagonalized in the Fourier domain producing an efficient algorithm for attaining spatially invariant resolution.

There are many embodiments for ISAM, each of which relies on specific imaging geometries and the various embodiments may advantageously be employed in variations on the instrumentation. Different geometries require somewhat different formulations of the forward and inverse scattering problems. Included here are the solutions for three geometries that are most likely to be useful in practice. The first geometry, for a Gaussian beam with a focus transversely scanned over a plane, is the most often used geometry of OCT when external surfaces are to be imaged. The second geometry, for an azimuthally scanned beam, is typically employed for catheters for imaging internally inside the human body, and may be utilized in applications wherein the beam is delivered to the irradiated sample by a needle, a probe, an endoscope, or a laparoscope. Finally, the full-field geometry is useful when external surfaces are to be imaged and speed of data acquisition is paramount. Other instruments will likely be amenable to be adapted to these geometries, and the ability to perform ISAM is not limited to these geometries. The types of incident fields that we have specifically addressed are focused Gaussian beams and plane waves because they are the most common and readily produced and detected beams used for OCT, however the scope of the present invention is not limited to these types of incident field.

In accordance with embodiments of the present invention, the capabilities of both OCT and OCM are greatly extended by computed imaging and synthetic aperture techniques. Among recently demonstrated advantages is the ability to resolve features in the sample that are outside of the confocal region. A more quantitatively accurate and faithful representation of the sample structure than hitherto available is provided by solution of the inverse scattering problem as applied both to full-field planar OCT/OCM as well as to OCT from an azimuthally-scanned catheter. In either case, and in accordance with preferred embodiments of the invention, the focus may advantageously remain fixed at the surface of the sample, while computed imaging techniques are used to infer the structure inside and outside of the depth-of-field. By applying the invention, the focus need not be scanned through the sample.

As further described below, a forward scattering model is derived which relates the measured data to the object structure. From this model, a solution of the inverse scattering problem is obtained that infers the object structure from the data. The achievable resolution and system bandpass is also derived from this forward model, and application of the method is demonstrated by means of a simulation.

Full-Field Non-Scanned Beam Implementation

By means of the novel methods described herein, computed imaging techniques are employed to reconstruct features that are both inside and outside the focus. Instead of scanning the focus through the sample, the focus is fixed at the surface of the sample, and no relative translation is needed between the objective and the sample. A frequency-swept source can be utilized to provide a new degree of freedom, replacing information lost by fixing the focus, without sacrificing detail outside of the focus. Because the objective and sample can remain fixed relative to each other, no translation hardware is needed which makes placing the objective on a fiber optic or a handheld probe easier. This method may lead to faster and more accurate full-field OCT imaging because data acquisition can be very rapid, requiring only that the two-dimensional interferogram is sampled while the frequency of the source is scanned. By virtue of computational image formation, the need to physically form an image of each plane in the volume, as typically done in full-field OCT, is obviated. As data acquisition speed and computational speed continue to increase, video-rate scanning of three-dimensional volumes may become possible.

In order to provide an understanding of computational image formation in the context of full-field OCT, a physical model for the scattering process is developed, and from this, a relationship between the data and the object structure is derived. Based on this relationship, the inverse scattering problem is solved to infer the sample structure from the data.

Full-field OCT allows an entire plane of scatterers to be ranged simultaneously, which makes it a very rapid way to acquire the structure of a volume. A full-field OCT system that is typical of the current state-of-the-art consists of a Michelson interferometer, again, with a broadband illumination source. Reference and sample beams are derived from the broadband source using a beam splitter. An extended area of the sample is illuminated by a broadband collimated beam through a microscope objective. The objective is focused at the depth of features of interest. A signal is scattered by the sample back through the objective. A reference beam is delayed to return to the beam splitter at the same time the signal scattered from the focus arrives. The reference and signal are superimposed and focused on a focal plane array (such as a charge-coupled device (CCD) sensor) which detects the interference signal. The amplitude of the interference signal corresponds to the reflections of scatterers at the focus plane. By translating the sample through the focus plane, the scatterers at many different depths may be ranged.

While this method can be used to obtain high resolution images for entire volumes of a sample quickly, it has a number of disadvantages. First, the sample and microscope objective must be translated relative to each other, which is relatively slow and requires fine positioning. Second, this method uses time-domain detection that produces a lower signal-to-noise ratio than Fourier-domain, or frequency-swept, OCT.

Figure 20A:
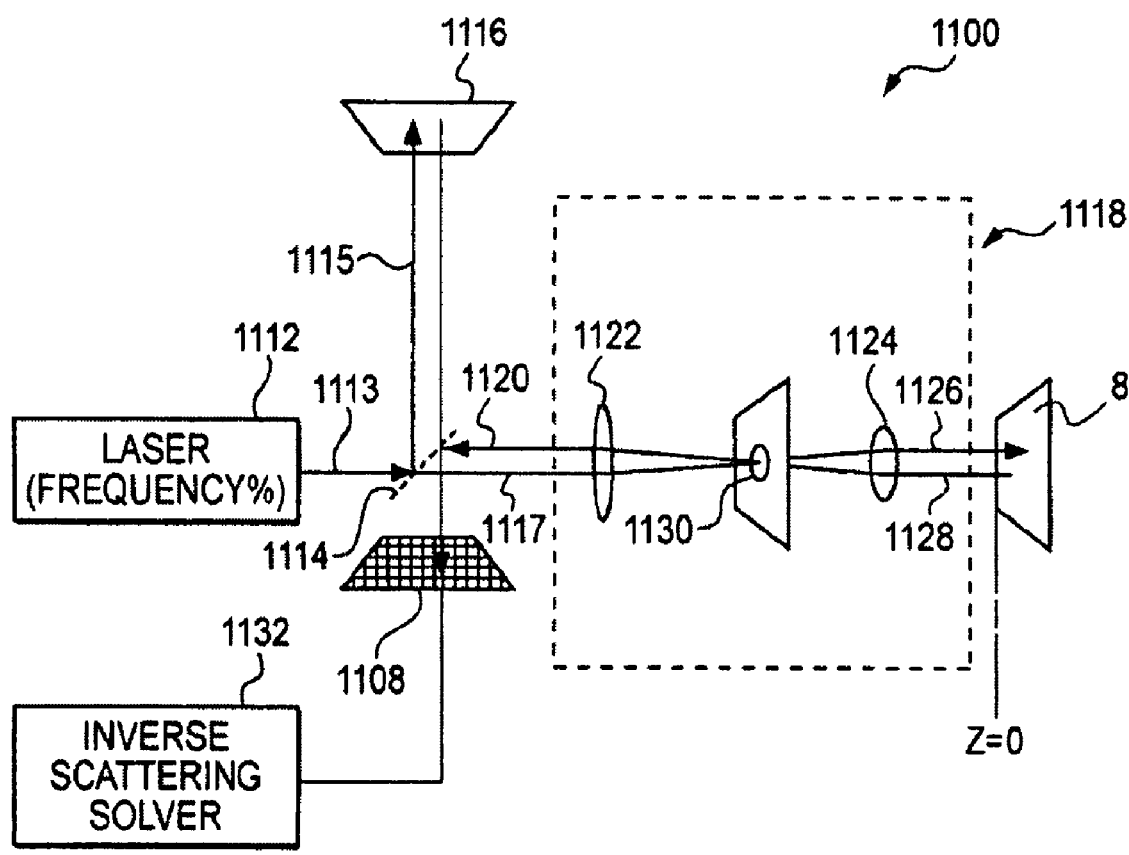
FIG. 20(*a*) is a schematic depiction of a full-field OCT system in accordance with a preferred embodiment of the present invention.

A full-field OCT system, in accordance with embodiments of the present invention, is now described with reference to FIG. 20(a) and is designated generally by numeral 1100. While system 1100, as shown, is based on a Michelson interferometer, other interferometric configurations such as that of a self-referencing Fizeau design, may be used and are encompassed within the scope of the present invention and of any claims appended hereto. In system 1100, the illumination source is a tunable narrow band laser 1112. It is to be understood that partially coherent sources may also be employed within the scope of the present invention, where their application is consistent with the methods described, and that references herein to a laser may also encompass sources that lack temporal or spatial coherence, or both, unless the particular context dictates otherwise.

Laser 1112 is tuned to wavelengths λ that correspond to spatial frequencies k. Laser 1112 nominally emits a plane wave (or is spatially filtered to produce one). The coherence length of this laser should be at least as twice as long as the total depth of the sample 8 under study, to ensure that fields scattered throughout the entire sample simultaneously interfere with the reference field.

Laser illumination 1113 is split by a beam splitter 1114 into two components. One component 1115 travels to a reference mirror (or delay mirror) 1116, and is reflected back through the beamsplitter 1114 to the output port where the focal plane array 1108 is located. It is to be understood that, most generally, numeral 1108 designates a detector, and that references to detector 1108 as a focal plane array are by way of non-limiting example. The other beam component 1117 is demagnified by a factor 1/M using a telescope 1118 of magnification M. The purpose of telescope 1118 is to concentrate the illumination onto the sample 8, and then relay a magnified scattered field 1120 to the focal plane array 1108. This telescope consists of two converging lenses: a relay lens 1122 and a microscope objective 1124. The illumination on the sample is a normally incident plane wave 1126. The sample scatters some radiation 1128 backwards through the telescope 1118. The telescope is aligned to afocally and telecentrically image the front surface of the sample to the focal plane array. Sitter et al., Three-dimensional Imaging: a Space-invariant Model for Space Variant Systems, Appl. Opt., vol. 29, pp. 3789-94 (1990) discusses three-dimensional imaging problems, and is incorporated herein by reference.

It is to be noted, significantly, that in a manner distinct from that of standard full-field OCT microscopy, the focus of the objective 1124 may remain fixed, in accordance with the present invention, at the surface of sample 8. For purposes of the following heuristic analysis, it is assumed that telescope 1118 is aberration free and vignetting inside the telescope is negligible. If the telescope is assumed to correct spherical aberration, then there is a finite volume within the sample space for which these assumptions hold. A pupil 1130 is placed at the focus of the illumination beam inside the telescope to spatially filter the backscattered signal so as to enforce a well-defined spatial bandlimit. The response of the telescope is modeled by a space-invariant convolution with a bandwidth determined by the pupil size. At the focal plane array 1108, the reference and sample signals superimpose and interfere, and the intensity of the interference is detected. The interference signal from detector 1108 is coupled to an Inverse Scattering Solver 1132, the operation of which is now described.

Figure 31:
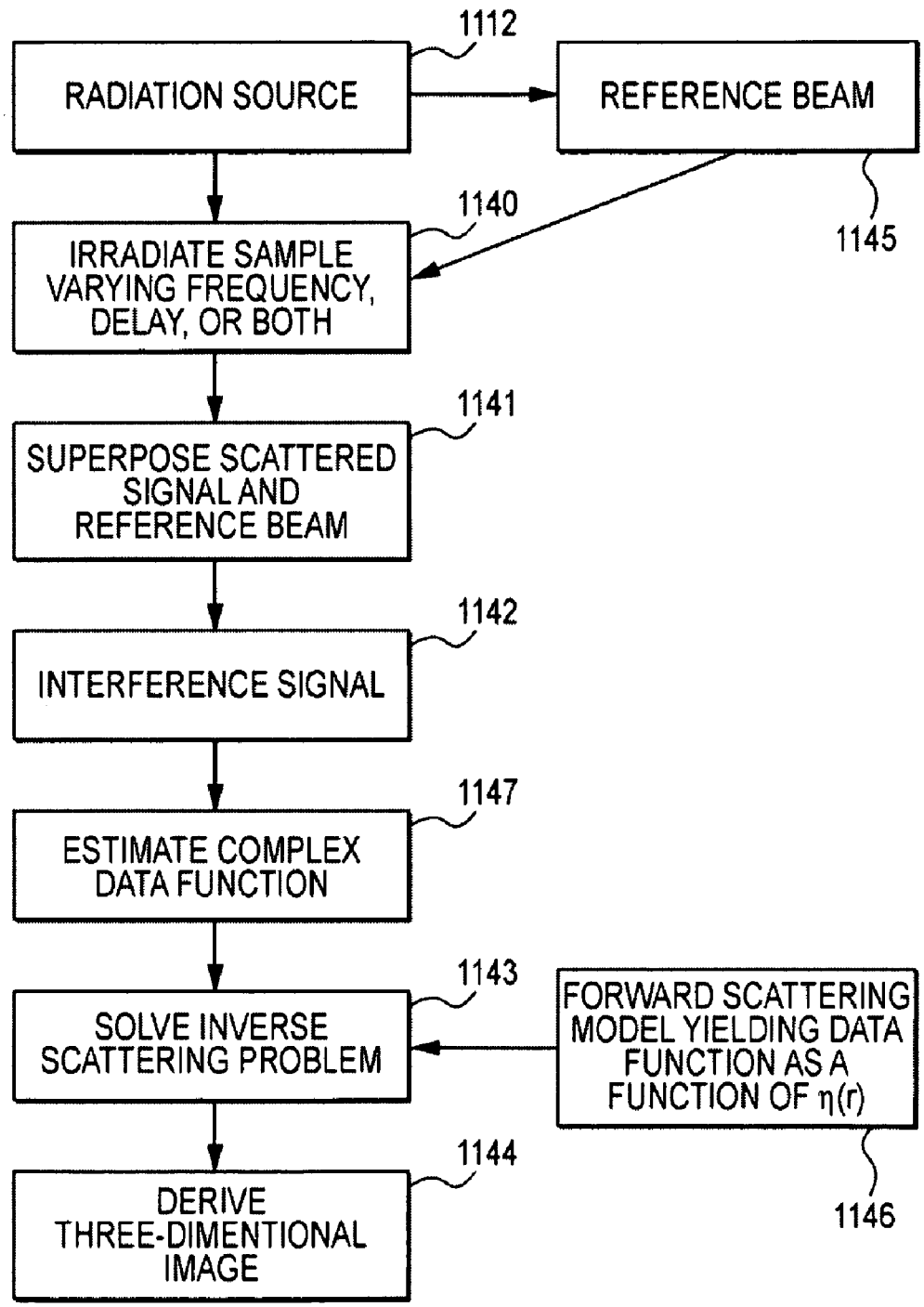
FIG. 31 is a flowchart depicting steps in imaging a sample using in accordance with embodiments of the present invention.

To derive the relationship between the object structure and the data detected on the sensor, a mathematical model of scattering of the illumination field by the object and interferometric detection at the sensor is now described with reference to FIG. 31. For convenience of description, a scalar field is substituted for the electromagnetic field, neglecting polarization effects. The incident field on the sample, provided in step 1140, is given by the expression:

$$E_i(r;k) = A(k)\exp(ikz) \tag{1}$$

where r is a location within the volume of sample 8, k is the spatial frequency of the illumination, A(k) is the amplitude of the illumination at frequency k, and $\hat{z}$ is the direction of increasing depth into the sample. For present purposes, it is assumed that the scattering is well-modeled by the weak or first Born scattering approximation, where the scattering by the object is modeled as a source. The susceptibility of the object is given by η(r) such that η(r)=0 for z<0.

The secondary scattered field $E_s(r';k)$ from the object at the plane z=0 is given by the expression $$E_s(r';k) = \int_V d^3 r E_i(r;k)\eta(r)\frac{\exp(ik|r'-r|)}{|r'-r|}. \tag{2}$$

To simplify this relationship, it is useful to define the two-dimensional Fourier transform $$\tilde{E}_s(q;k) = \int_{z'=0} d^2 r' E_s(r';k)\exp(iq\cdot r')$$

with q being a transverse spatial frequency such that $q\cdot\hat{z}$=0. In terms of q, Eq. (2) is found to be $$\tilde{E}_s(q;k) = A(k)\int_V d^3 r \eta(r)\exp\{i[q\cdot r]+iz[k+k_z(q)]\}k_z(q)^{-1} \tag{3}$$

where $k_z(q)=\sqrt{k^2-q^2}$, and substituting Eq. (1) into Eq. (2). (In accordance with convention, $x^2$ designates the square modulus of a vector x.) The three-dimensional Fourier transform is defined such that $$\tilde{\eta}(Q) = \int_V d^3 r \eta(r)\exp(iQ\cdot r).$$

It is then found that the right-hand integral can be expressed in terms of $\tilde{\eta}(Q)$:

$$\tilde{E}_s(q;k)=A(k)k_z(q)^{-1}\tilde{\eta}\{q+\hat{z}[k+k_z(q)]\} \tag{4}$$

The field $E_f(r;k)$ is produced by the propagation of $E_s(r';k)$ through telescope 1118 to focal plane array 1108 (shown in FIG. 20(*a*)). Because the telescope is assumed to be an aberration-free telescope which afocally and telecentrically images the plane at the sample z=0 to the focal plane array in the plane $z=z_f$, its function can be modeled by a simple convolution with a point spread function accounting for the finite bandwidth of the telescope, and a magnification factor given by M. The field at the focal plane array is given by $E_f(r;k)$, and the point spread function of the telescope is given by P(r;k). The relationship between $E_f(r;k)$ and $E_s(r';k)$ is $$E_f(r;k)=M^{-1}\int d^2 r' E_s(r';k)P(r/M-r';k) \tag{5}$$

where the factor $M^{-1}$ accounts for energy conservation between the two planes.

If we further define the Fourier transforms $$\tilde{E}_f(q;k) = \int_{z=z_f} d^2 r E_f(r;k)\exp(iq\cdot r)$$

and the coherent transfer function of the telescope $\tilde{P}(q;k)=\int d^2 r\, P(r;k)\exp(iq\cdot r)$ the convolution of Eq. (5) may be expressed as $$\tilde{E}_f(q;k) = M\tilde{E}_s(Mq;k)\tilde{P}(Mq;k) \quad (6)$$
$$= MA(k)\tilde{P}(Mq;k)k_z(Mq)^{-1}\tilde{\eta}\{Mq + \hat{z}[k + k_2(Mq)]\}.$$

Eq. (6) specifies a relationship between Fourier components of the field on the focal plane array and those of the object susceptibility.

In accordance with preferred embodiments of the invention, reference mirror 1116 is placed to effect a delay on the reference beam 1145 of $\tau$ relative to the total delay required for the beam to travel from the beamsplitter 1114 to the plane $z=0$ in the sample arm and back. The reference field $E_r(r;k,\tau)$, relayed to the focal plane array is then given by $$E_r(r;k,\tau) = A(k)\exp[i\omega(k)\tau], \quad (7)$$

where $\omega(k)$ is a dispersion relation relating the temporal frequency with the spatial frequency in the sample medium.

For example, if the object medium is free space, then $\omega(k) = kc$, where c is the speed of light in vacuum. The interference intensity $I(r;k,\tau) = |E_r(r;k,\tau) + E_f(r;k)|^2$ on the focal plane array is then given by $$I(r;k,\tau) = |A(k)| + |E_f(r;k)|^2 + 2A(k)Re\{E_f(r;k)\exp[-i\omega(k)\tau]\}. \quad (8)$$

The part of the signal 1142 that is due to interference between the signal and reference beams occurring in step 1141 is defined as the data function $D(r;k) = A(k)E_f(r;k)$. The complex $D(r;k)$ can be estimated from measurements of $I(r;k,\tau)$. For example, three measurements of $I(r;k,\tau)$ such that $\omega\tau = 0, \pi/2,$ and $\pi$ may be summed (in step 1147 of FIG. 31) to yield, as an approximation:

$$D(r;k) = \frac{1-i}{4}I(r,k,0) - \frac{1+i}{4}I(r,k,\pi/\omega) + \frac{i}{2}I(r,k,\pi/2\omega). \quad (9)$$

The foregoing method of phase-shifting for interferometry is described, for example, in Hariharan, Optical Interferometry (Academic Press, 2003), which is incorporated herein by reference. Inserting the results of Eq. (6), the Fourier transform of the data function, which is $\tilde{D}(q;k) = \int d^2r\, D(r;k)\exp(iq\cdot r)$, can be expressed as $$\tilde{D}(q;k) = \tilde{K}(q;k)\tilde{\eta}\{Mq + \hat{z}[k + k_z(Mq)]\}, \quad (10)$$

where, for convenience, the bandpass function is defined $$\tilde{K}(q;k) = MA(k)^2\tilde{P}(Mq;k)k_z(Mq)^{-1}. \quad (11)$$

Thus, the data are expressed in terms of the 3-D Fourier transform of the sample structure, and, so, the resolution of the reconstruction of the sample structure is space invariant. However, vignetting and aberrations in the telescope limit the volume over which this resolution can be obtained.

To obtain the measurements needed to reconstruct $\eta(r)$, one must vary both k and $\tau$. In practice, however, it is often slow and inconvenient to adjust both. If one is willing to tolerate some image artifacts, just one of these parameters need be scanned. For simplicity, it is assumed that the pupil function $P(r';k)$ is real and symmetric, which is often the case (for example, when pupil 1130 is circular), so that $\tilde{P}(q;k)$ is likewise real and symmetric.

If mirror 1116 is fixed such that $\tau=0$, then the imaginary component of $D(r;k)$ is not obtainable. If the imaginary part of $D(r;k)$ is assumed to be zero, then due to the Hermitian symmetry of the Fourier transform of real functions $\tilde{D}(-q,k) = \tilde{D}(q,k)$. The function $\tilde{\eta}(Q)$ then also has Hermitian symmetry reflected over the axis. The effect is that a conjugate image of the susceptibility is present, reflected across the plane $z=0$. Because the delay $\tau=0$ corresponds to the plane $z=0$, as long as the entire sample is contained such that $z>0$, the conjugate image and the real image do not overlap. In addition, there is an artifact corresponding to the term $|E_f(r;k)|^2$ in Eq. (8). If the magnitude of the sample signal is small relative to the reference signal, the magnitude of this artifact is also small compared to the real image and can be neglected. This term may also be eliminated by modulating the phase of the reference field and locking in only on the modulation, i.e., by phase-sensitive detection of the interference signal.

If the delay $\tau$ is scanned, and the laser emits all frequencies k simultaneously (such as occurs in a mode locked laser or a spontaneous emission source), the signal $I_T(r;\tau)$ is the sum of the interference patterns over all emitted frequencies:

$$I_T(r;\tau) = \frac{1}{2\pi}\left[\int_{-\infty}^{\infty}dk\left(\frac{d\omega}{dk}\right)(|A(k)|^2 + |E_f(r;k)|^2)\right] + \frac{1}{\pi}Re\left\{\int_{-\infty}^{\infty}dk\left(\frac{d\omega}{dk}\right)D(r;k)\exp[-i\omega(k)\tau]\right\}. \quad (12)$$

The term in square brackets in Eq. (12) is a background intensity that is independent of T and therefore is easily subtracted to remove its contribution from the measured intensity. Neglecting the background intensity and the slowly-varying Jacobian $$\left(\frac{d\omega}{dk}\right),$$

Eq. (12) relates the real part of the inverse Fourier transform of $D(r;k)$ with respect to k to the total intensity $I_T(r;\tau)$. To be able to remove the Re{ } operation so that a unique solution for $D(r;k)$ can be found, one equates $D(r;-k) = D(r;k)^*$. Eq. (10) then likewise enforces Hermitian symmetry on $\eta(-Q) = \eta(Q)^*$. Therefore in this case the reconstructed susceptibility is assumed to be real-valued.

In this derivation, the focal plane of the objective and the front surface of the sample are assumed to coincide (at $z=0$). This assumption has simplified the preceding analysis and presentation, but it is not required within the scope of the present invention. If the focus is placed below the sample surface by a distance z0, but the delay produced by the reference still coincides with the delay of the sample surface, the data can be modified to account for the displacement. In particular, the modified data $\tilde{D}'(q;k)$ is related to the sampled data $\tilde{D}(q;k)$ by:

$$\tilde{D}'(q;k) = \tilde{D}(q;k)\exp\{iz_0[k - k_z(Mq)]\}. \quad (13)$$

This formula can be found by noting that the field relayed by the telescope is now situated at the plane $z=z_0$, adding an extra term $\exp\{-iz_0[k+k_z(q)]\}$ to the right side of Eq. (3). At the same time, the delay reference mirror must be moved a distance further from the beamsplitter so that the new effective delay corresponds to the front surface of the sample, adding a factor of $\exp(-2ikz_0)$ to the right side of Eq. (7) to place the reference delay coincident with the front surface of the sample. Effectively the measured field is computationally propagated at each frequency to the surface of the sample.

Using the mathematical model 1146 developed in the foregoing discussion, a solution to the inverse scattering problem may be derived in step 1143. In general, the solution is ill-posed and so regularization techniques are used to produce a stable solution. Because the forward problem is linear, we derive a linearized inverse based on least-squares error. To do so, we first specify the complete forward operator K such that $D=K\eta$, which relates the data to the object structure $$\tilde{D}(r;k)=K\eta=\int d^3r' K(r',r;k)\eta(r') \quad (14)$$

where the kernel $K(r',r;k)$ of the operator K is given by $$K(r', r; k) = M^{-1}A(k)^2 \int d^2 r'' \frac{\exp(ik|r''-r'|)}{|r''-r'|} P(r/M - r''; k). \quad (15)$$

Given this relation between the data and the object, we can define a least-squares solution $\eta^+(r)$ for object susceptibility as $$\eta^+(r) = \underset{\eta}{\mathrm{argmin}}|D - K\eta|^2 \quad (16)$$

$$= \underset{\eta}{\mathrm{argmin}} \int d^2 r' \int dk |\tilde{D}(r';k) - K\eta(r)|^2.$$

Expressed in operator notation, the solution to this least squares problem is given by the pseudo inverse $\eta^+ = (K^\dagger K)^{-1} K^\dagger D$ where $K^\dagger$ is the Hermitian conjugate of K and $K^\dagger K$ is assumed to be invertible. It is much simpler to formulate the least-squares problem in the Fourier domain, using the relation of Eqs. (10) and (11). If we instead define the operator K such that $D=K\tilde{\eta}$. This operator can be used to construct a least squares solution $\tilde{\eta}^+$ such that:

$$\tilde{\eta}^+(Q) = \underset{\tilde{\eta}}{\mathrm{argmin}}(|D - K\tilde{\eta}|^2 + \gamma|\tilde{\eta}|^2) = \quad (17)$$

$$\underset{\tilde{\eta}}{\mathrm{argmin}}\left(\int d^2 q \int dk |\tilde{D}(q;k) - \tilde{K}(q;k)\tilde{\eta}\{Mq + \hat{z}[k + k_z(Mq)]\}|^2 + \right.$$

$$\left. \gamma|\tilde{\eta}\{Mq + \hat{z}[k + k_z(Mq)]\}|^2\right)$$

with $\tilde{K}(q;k)$ taken from Eq. (11). A Tikhonov regularization term with regularization constant $\gamma$ has been added to stabilize the solution and ensure that a unique solution exists. The solution $\tilde{\eta}^+$ is given in step 1144 by $$\tilde{\eta}^+\{Mq + \hat{z}[k + k_z(Mq)]\} = (K^\dagger K + \gamma)^{-1} K^\dagger D \quad (18)$$

$$= \frac{\tilde{D}(q;k)\tilde{K}^*(q;k)}{|\tilde{K}(q;k)|^2 + \gamma}.$$

Resolution and Bandpass of Full-Field ISAM

Eq. (10) expresses a relationship between the 2-D Fourier transform of the data and the 3-D Fourier transform of the object. As mentioned previously, this relationship implies that the resolution of the reconstructed object is space invariant. With suitable specifications of the instrument, it is possible to identify the region of the Fourier space of the structure function that can be sampled. This region is called the "band volume" and is an analogue to the bandlimit of one-dimensional signals, except that the band volume consists of the interior of a shape in three-dimensional Fourier space rather than just a one-dimensional interval.

There are two specifications of the instrument that determine the shape of the band volume. The first is the bandwidth of the illumination, which is specified by the interval of frequencies $k_{min} < k < k_{max}$. The other parameter is the numerical aperture (NA) of the imaging system $0 < NA < 1$. A particular numerical aperture implies a pupil bandpass $$\tilde{P}(q;k)=1 \text{ for } |q| \leq (NA)k$$

$$\tilde{P}(q;k)=0 \text{ for } |q| > (NA)k. \quad (19)$$

These inequalities constrain which points on the data function $\tilde{D}(q;k)$ can be sampled. The relation of Eq. (10) is a one-to-one mapping between each of these points in the data function and points in the 3-D Fourier space of the object $\tilde{\eta}(Q)$. The band volume is the intersection of the volumes defined by the two inequalities expressed in terms of the object spatial frequency Q $$k_{min} < Q^2/(2Q \cdot \hat{z}) < k_{max} \quad (20)$$

$$(2Q \cdot \hat{z})\sqrt{Q^2 - (Q \cdot \hat{z})^2} / Q^2 < NA.$$

Figure 20B:
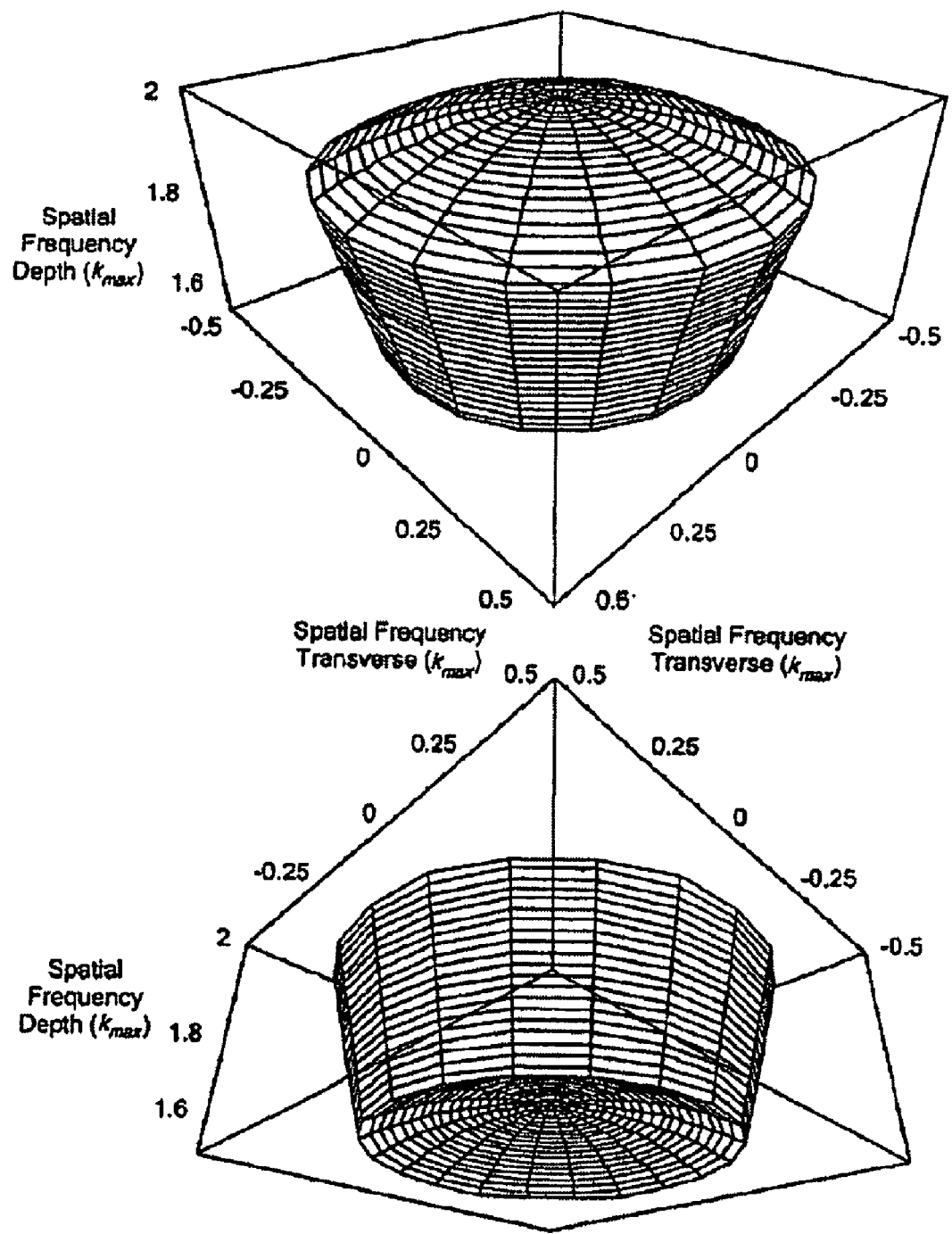

FIG. 20(b) shows an example of a band volume for an instrument with 0.5 NA and bandwidth from 0.8 $k_{max} < k < k_{max}$. The units of the axes are all scaled by $k_{max}$. There are two views so that the top and bottom surfaces are both visible. The top and bottom surfaces are spherical (with different radii and centers), and the side surface is a right circular cone with its vertex at the origin.

In the limit of small bandwidth and low numerical aperture, the band volume shape approaches that of a circular cylinder. In this limit, the resolution in the axial direction is determined solely by the bandwidth, and the transverse resolution is determined by the numerical aperture, as is normally assumed in OCT. However, the band volume becomes less cylindrical and more cone-shaped as the numerical aperture and bandwidth increase, and axial and transverse resolutions are dependent on both the bandwidth and numerical aperture.

Simulation of Full-Field ISAM

A simulation is now presented to demonstrate inverse scattering in full-field OCT. For purposes of the simulation, an object (element 8 shown in FIG. 20(a)) is taken as comprising a set of randomly placed point scatterers. The simulated object was imaged with a simulated full-field OCT system, and then the structure of the object was reconstructed from the data. The simulated object volume cross-sectional area was 25 wavelengths in depth, and 40 by 40 wavelengths in the transverse direction. The illumination source had a Gaussian spectrum with a 40% fractional full-width-half-max bandwidth (corresponding, for example, to 320 nm of bandwidth centered at 800 nm). The simulated numerical aperture of the imaging objective was 0.5.

To synthesize the data, first the scattered field $E_s(r;k)$ was calculated using Eq. (2), where the object $\eta(r)$ was a collection of randomly chosen discrete points. From this, a two-dimensional Fourier transform computed $\tilde{E}_s(q;k)$. Then the synthesized data function was calculated by $\tilde{D}(q;k)=A(k)\tilde{E}_s(q;k)\tilde{P}(q;k)$. Finally, a two-dimensional inverse Fourier transform yielded $D(r';k)$ Eq. (10) was deliberately not used to compute the data because using an alternate and more direct method of computing the data provided a better test of the inverse scattering method.

Figure 20C:
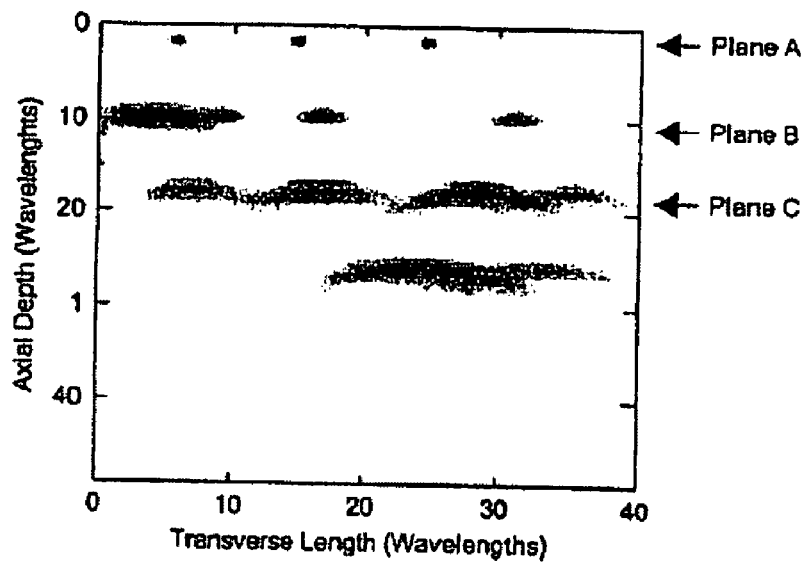

FIG. 20(c) shows the projection of the simulated data collapsed (summed) along one transverse direction. The units are in terms of the center wavelength. Instead of showing the Fourier-transformed function $\hat{D}(r;k)$ itself, which would be difficult to interpret if it was plotted directly, we show the inverse Fourier transform of $\hat{D}(r;k)$ with respect to k. It is the data on the focal plane array that would be observed if the delay $\tau$ were scanned, rather than the frequency k, which is given by the intensity function of Eq. (12). The focus is on the top surface at zero depth, which also corresponds to zero delay. As can be seen, as the delay is increased from zero, the diffracted images of the point scatterers become increasingly large. This corresponds to the standard degradation in resolution one expects from defocus when inverse scattering is not used.

To compute the image estimate $\eta^+(r)$ from the synthetic data $D(r; k)$, first $\tilde{D}(q;k)$ was computed using the two-dimensional Fourier transform. Next, Eq. (18) was used to compute $\tilde{\eta}^+ + \{q + \hat{z}[k+k_z(q)]\}$. However, in practice to find $\eta^+(r)$ from $\eta^+(Q)$ numerically, one would likely use the three-dimensional inverse discrete Fourier transform. Unfortunately, Eq. (18) does not specify $\tilde{\eta}^+$ in a form to which the inverse discrete Fourier transform can be readily applied, because it is a function of the more complicated argument $q + \tilde{z}[k+k_z(q)]$. In practice, this means that the discrete sampling of the function $\tilde{\eta}^+$ is uniform in the variables q and k and not in Q to which the inverse Fourier transform can be directly applied. By using an interpolator, one can compute the samples of $\tilde{\eta}^+$ on points that are uniform in Q from existing samples of $\tilde{\eta}^+ \{q+\hat{z}[k+k_z(q)]\}$. In this simulation, a one-dimensional cubic B-spline interpolator was used to interpolate from the coordinates $q+\hat{z}[k+k_z(q)]$ to Q. Because only the $\hat{z}$ coordinate is not sampled uniformly, the resampling only needs to occur along this direction.

Figure 20D:
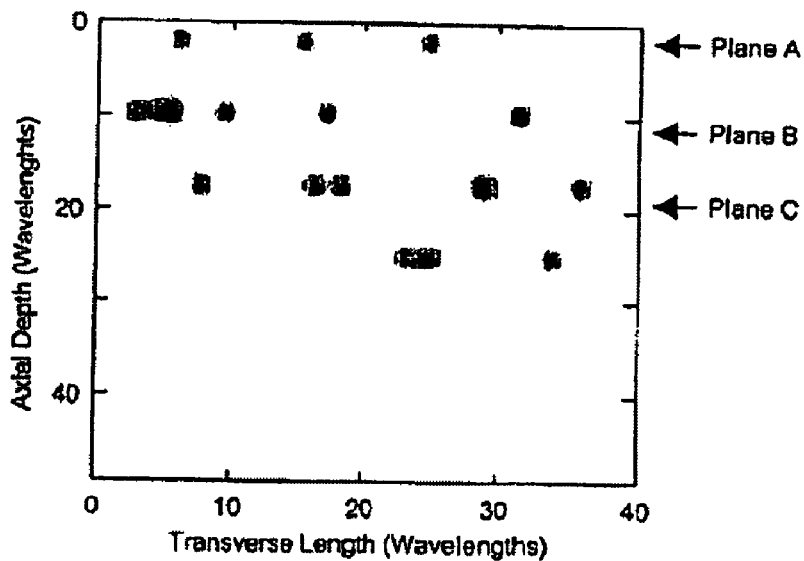

Finally, after taking the three-dimensional inverse Fourier transform of $\tilde{\eta}^+(Q)$, the reconstruction $\eta^+(r)$ results, which is shown in FIG. 20(d). As can be seen, the reconstruction corrects for the diffraction of the data, and produces point-like images. FIG. 21 shows three en face planes corresponding to the depths A, B, and C marked in FIG. 21(c). The left column is the time-domain data measured in each of the en face planes, and the right column is the image of the scatterers computed by inverse scattering. Planes that are further from the focus have more diffuse images when viewed in the raw data because of the effect of defocus. One can also see the interference between the images of adjacent scatterers. Despite the interference between scatterers, each point is clearly resolved with space-invariant resolution in the reconstructed image. This shows the algorithm correctly separates the interference patterns from scatterers to produce high resolution images.

Figure 22A:
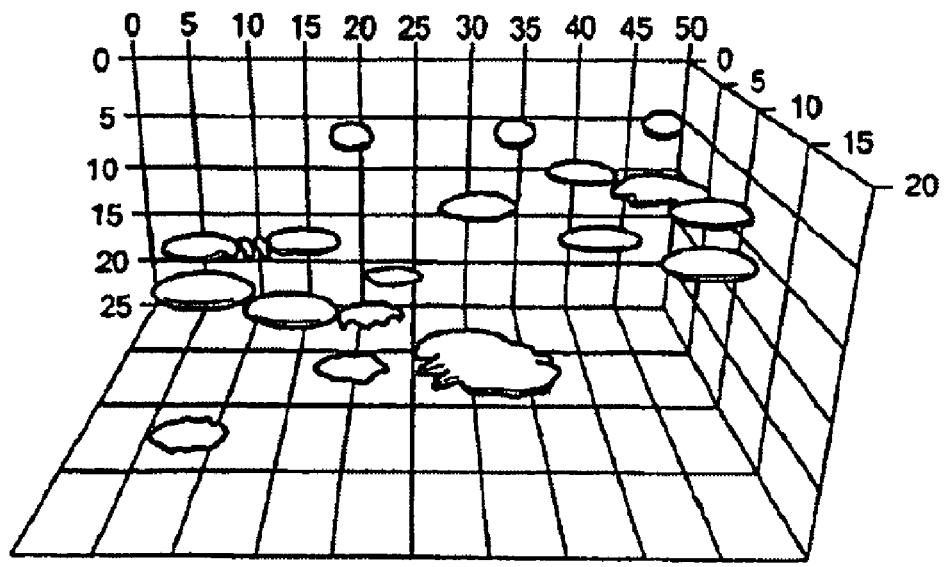
FIG. 22(*a*) compares a volume isosurface plot of the raw data with the reconstructed computed image of FIG. 22(*b*).
Figure 22B:
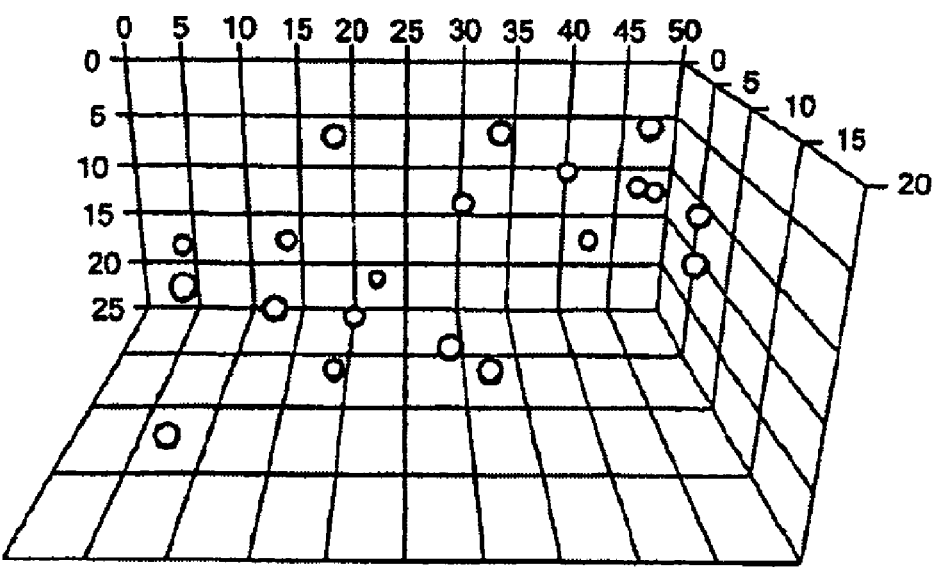

To show the overall improvement to the data, FIG. 22(a) is a volume isosurface plot of the raw data, while the reconstructed computed image is shown in FIG. 22(b). Again, the blurring of the data is increasingly apparent with increasing distance from the focus plane at the top of the volume. In addition, stripe-like features can be seen for the isosurfaces corresponding to interfering scatterers. This method can correct for the diffraction effects and produce point-like images in FIG. 22(b) for each of the scatterers. The planes of the scatterers need not be so widely separated for the algorithm to distinguish them, but was deliberately done to make the diffraction effects easier to visualize.

There is an important difference in the reconstructions of full-field OCT and conventional scanned beam OCT. In conventional scanned beam OCT, it has been shown by Ralston et al., Inverse Scattering for Optical Coherence Tomography, J. Opt. Soc. Am. A, vol. 23, pp. 1027-1037, (2006), incorporated herein by reference, that the magnitude of the signal captured from scatterers away from the focus is inversely proportional to the distance from the focus. In practice this places a limit on the axial range of the sample that can be imaged before the signal-to-noise ratio becomes unacceptable. However, there is no such attenuation of the signal away from the focus in the full-field OCT case. The practical limit to the depth of full-field OCT is determined by vignetting of the relayed field inside the relay telescope, and the scattering of the sample. However, this advantage may be offset because full-field OCT may be less able to discriminate between single scattering and multiply scattered photons due to its multimode detection.

Transverse-Scanned Focused Gaussian Beam Implementation

Figure 23:
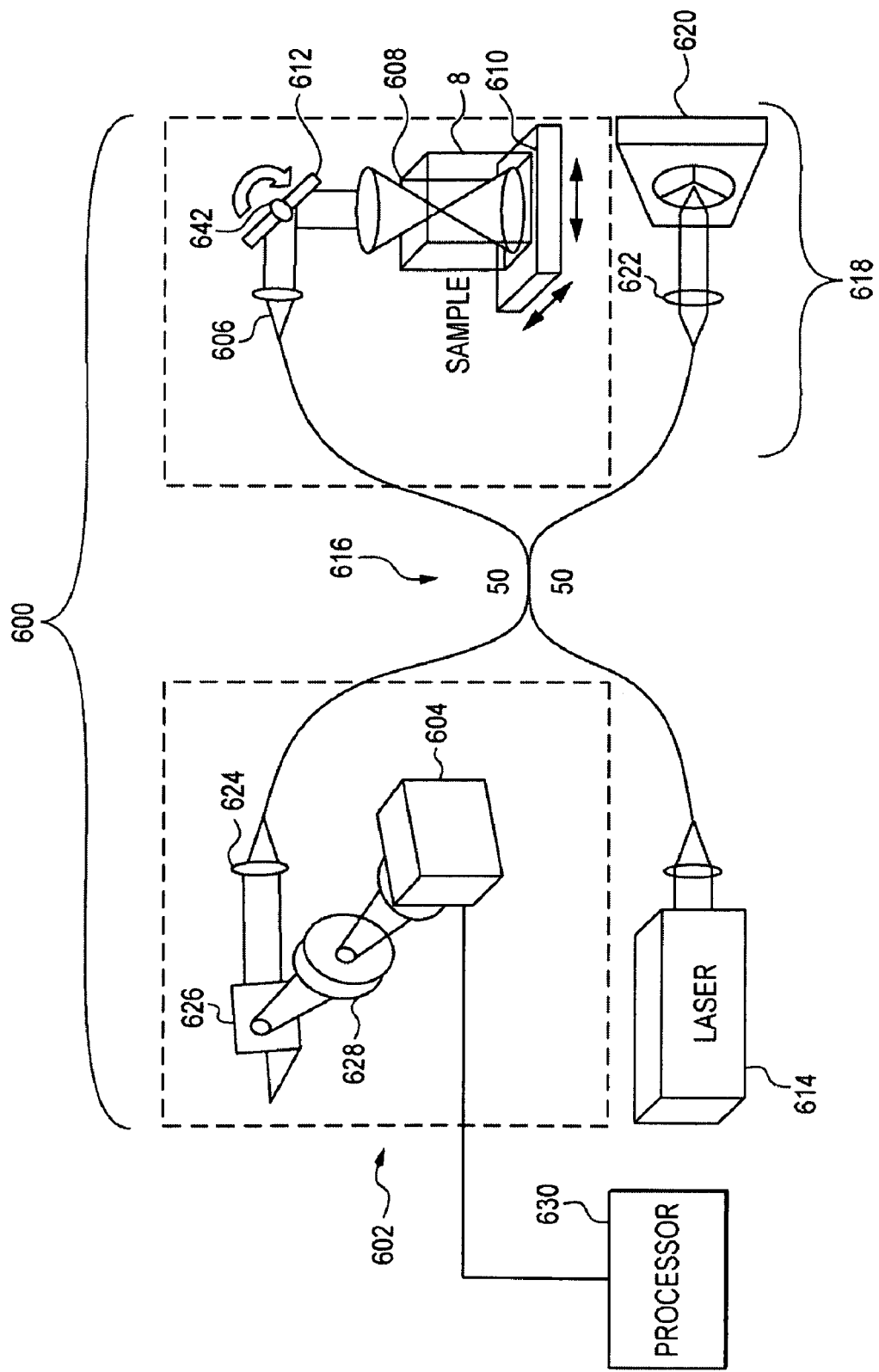
FIG. 23 is a schematic depiction of an interferometric synthetic aperture microscope using spectral detection in accordance with an embodiment of the present invention.

Preferred embodiments of the present invention implement computed interferometric imaging by employing a fiber-optic Michelson interferometer 600 seeded by a source of femtosecond pulses, as now described with reference to FIG. 23. A spectral interferometer, designated generally by numeral 602, measures the interferometric cross-correlation between a fixed-delay reference pulse and a pulse reflected back from a sample 8. The measured spectrum on a line camera 604 corresponds to the Fourier transform of the cross-correlation signal, from which the amplitude and phase of the reflected field from the sample are inferred. The sample probe beam 606 is focused by a microscope objective 608 so that the beam focus is at a fixed distance inside the sample. At each position of the beam, the spectral interferogram of the backscattered optical field is measured. The beam is laterally translated in two-dimensions through the sample by moving a stage 610 or by steering the beam with a pair of galvanometer-driven mirrors 612 before entering the objective.

Measurements are made using a femtosecond spectral interferometer 600. Fourier-domain, or frequency-swept, OCT, has been described by Choma et al., Sensitivity advantage of swept source and Fourier domain optical coherence tomography, Opt. Expr., vol. 111, pp. 2183-89 (2003), which is incorporated herein by reference. A femtosecond laser 614 (such as supplied by Kapteyn-Murnane Laboratories of Boulder, Colo.) delivers ultrashort pulses to provide broadband illumination for the system. In one embodiment of the invention, the center wavelength of the source is 800 nm, with a bandwidth of 100 nm. These first-order field quantities fluctuate too rapidly to be detected directly, thus an optical fiber-based Michelson interferometer is incorporated. The illumination is divided by a 50:50 fiber-optic coupler (splitter) 616 between a reference arm 618 containing a delay mirror 620 and a sample arm that contains a lens (objective) 622 to focus the Gaussian beam into the sample 8. Light returns from the sample and reference arms and is directed into spectrometer 602. In the spectrometer, the light is collimated with an achromatic lens 624 and dispersed off of a blazed gold diffraction grating 626, which, in one embodiment, has 830.3 grooves per millimeter and a blaze angle of 19.70 degrees for a blaze wavelength of 828 nm. To reduce lens aberrations, the dispersed optical spectrum is focused using a pair of achromatic lenses 628. The focused light is incident upon a line-scan camera (L104k-2k, Basler, Inc.) 604 which contains a 2048-element charge-coupled device (CCD) array with 10×10 µm detection elements. Camera 604 operates at a maximum read-out rate of over 29 kHz, thus one axial scan can be captured during an exposure interval of about 34 µs. The data is sent to processor 630 which may also govern operation of a galvanometric controller 642 and receive a trigger derived therefrom in order to activate frame acquisition, for example.

We obtain a mathematical model of interferometric synthetic aperture microscopy (ISAM) by considering the propagation of the focused beam from the objective into the sample (into some volume V), scattering within the sample (in the first Born approximation), the propagation of the scattered light back into the objective (over some surface Σ), and the measurement of the cross-correlation with the reference pulse. The expression that models these steps (17) is given by $$S(r_0, k) = A(k) \int_\Sigma d^2 r \int_V d^3 r' G(r', r, k) g(r' - r_0, k) \eta(r') g(r - r_0, k) \quad (21)$$

where k is the wave number of the illumination, $r_0$ is the transverse position of the Gaussian beam, g describes the normalized Gaussian beam profile, $A^2(k)$ is the power spectral density of the source, G is the Green function, and η is the susceptibility of the sample. The normalized beam profile is given by $g(r,k)=W^{-2}(k)e^{-r^2/2W^2(k)}/2\pi$, where $W(k)=\alpha/k$, $\alpha=\pi/$NA, and NA is the numerical aperture of the beam. The Green function is given by $G(r',r,k)=e^{ik(r-r')}/|r-r'|$. After two-dimensional (2-D) Fourier transformation with respect to $r_0$, and further manipulation, the 2-D Fourier transform of the signal is given by the expression $$\tilde{S}(Q, k) = A(k) \int d^2 q \quad (22)$$
$$\int dz' \frac{i 2\pi}{k_z(q)} e^{ik_z(q)(z'-z_0)} \tilde{g}_0(q, k) e^{ik_z(z'-z_0)} \tilde{g}_0(Q - q, k) \tilde{\eta}(Q; z'),$$

where $k_z(q)=\sqrt{k^2-q^2}$, $z_0$ is the position of the beam focus, $\tilde{\eta}(Q,z')$ is the 2-D transverse Fourier transform of the susceptibility, and $\tilde{g}_0(q,k)=e^{-q^2\alpha^2/2k^2}$ is the 2-D Fourier transform for the beam profile g(r,k) in the waist plane of the beam. After the expression for $\tilde{g}_0$ is substituted into Eq. (22), and an asymptotic expansion of $\tilde{S}$ is made for large $\alpha^2$, this relationship reduces to $$\tilde{S}(Q, k) = A(k) \left( \frac{i 2 \pi^2}{k_z(Q/2)} \frac{k^2}{\alpha^2} e^{-2ik_z(Q/2)z_0} e^{-\frac{\alpha^2 Q^2}{4k^2}} \right) \tilde{\tilde{\eta}}(Q; -2k_z(Q/2)), \quad (23)$$

where $\tilde{\tilde{\eta}}$ is the 3-D Fourier transform of η, i.e. the one dimensional Fourier transform of $\tilde{\eta}(Q;z)$ with respect to z. This expansion is valid even when NA≈1 because $\alpha^2$ is sufficiently large for the first term of the expansion to dominate. Eq. (23) relates the 3-D Fourier transform of the object susceptibility to the 2-D Fourier transform of the signal. Implicit in this formula is a diagonal linear integral operator in the 3-D Fourier space of the susceptibility, and so the achievable resolution is spatially-invariant and does not depend on the proximity to the focus.

Because of the simple relationship between the susceptibility and the signal, ISAM can be implemented efficiently by resampling or interpolating the data in a manner analogous to the numerical implementation of the Fourier projection slice theorem, as described in Natterer, The Radon Transform, (Wiley, 1986, incorporated herein by reference) and as used in x-ray computed tomography or synthetic aperture radar (SAR), but the resampling grid for ISAM is hyperbolic rather than polar. In addition, since Eq. (23) is a multiplicative (or diagonal) form, generalization to a regularized inverse method such as Tikhonov regularization (Tikhonov, Dokl. Akad. Nauk SSR, vol. 39, p. 195, 1943) is straightforward.

Regardless of the type of detection used, the beam orientation is fixed while the axis is translated over the sample on a Cartesian grid in directions orthogonal to the beam axis and subsequent axial scans are displayed on adjacent lines to form a tomogram. Suppose the beam is generated by light emerging from an optical fiber and then propagating through a lens to form a focused beam incident on the sample. With the axis of the fiber passing through the point $r_0$ in the z=0 plane and with the waist plane of the focused field at $z=z_0$, the incident field may be described by the power spectrum $|A(k)|^2$ and a normalized mode g such that $$U_i(r;r_0,k) = A(k) g(r-r_0). \quad (24)$$

The beam may be described in a plane wave decomposition, $$g(r - r_0, k) = \frac{1}{(2\pi)^2} \int d^2 q e^{iq \cdot (r - r_0)} e^{ik_z(q)(z-z_0)} \tilde{g}_0(q, k), \quad (25)$$

where $\tilde{g}_0$ is the two dimensional Fourier transform of g in the $z=z_0$ plane, and the dispersion relation is given by $k_z=\sqrt{k^2-q^2}$. The beam waist is assumed to depend on the wave number, as $W_0(k)=\alpha/k$ where $\alpha=\pi/NA$ and NA is the numerical aperture of the output lens. Thus $$\tilde{g}_0(q,k) = e^{-q^2 W_0^2/2} = e^{-q^2\alpha^2/(2k^2)}. \quad (26)$$

The scattered field, within the first Born approximation, is given by $$U_s(r;r_0,k) = \int d^3 r' G(r',r,k) U_i(r',r_0,k) \eta(r'). \quad (27)$$

Making use of the expressions above for the incident field, $$U_s(r;r_0,k) = A(k) \int d^3 r' G(r',r,k) g(r'-r_0,k) \eta(r'). \quad (28)$$

The signal coupled back in to the fiber is given by the projection of the backscattered field onto the fiber mode g at the exit plane of the fiber. Thus $$S(r_0,k) = \int_{z=0} d^2 r U(r;r_0,k) g(r-r_0,k), \quad (29)$$

which becomes $$S(r_0,k) = A(k) \int_{z=0} d^2 r \int d^3 r' G(r',r,k) g(r'-r_0,k) g(r-r_0,k) \eta(r'). \quad (30)$$

The Green function for free-space is given by the angular spectrum $$G(r', r, k) = \frac{i}{2\pi} \int d^2 q e^{iq \cdot (r-r')} \frac{e^{-ik_z(q)(z-z')}}{k_z(q)}, \quad (31)$$

where it is assumed that the scatterers are all located such that z<z' for the whole support of the scatterers. Making use of this expression and Eq. (30), it may be seen that the two-dimensional Fourier transform of S with respect to $r_0$ is given by the expression $$\tilde{S}(Q, k) = i 2\pi A(k) \int d^2 q \int dz' \frac{1}{k_z(q)} e^{ik_z(q)(z'-z_0)} \quad (32)$$
$$e^{ik_z(q-Q)(z'-z_0)} e^{-\frac{\alpha^2 q^2}{2k^2}} e^{-\frac{\alpha^2 |q-Q|^2}{2k^2}} \tilde{\eta}(Q, z').$$

This equation may be solved for $\eta$ by blunt numerical methods. Such methods are numerically expensive. An analytic result may be obtained by considering the shifted form of the integral $$\tilde{S}(Q, k) = i2\pi A(k) \int d^2 q \int dz' \frac{1}{k_z(q)} e^{ik_z(q)(z'-z_0)} \qquad (33)$$

$$e^{ik_z(q-Q)(z'-z_0)} e^{\frac{-\alpha^2 Q^2}{4k^2}} e^{\frac{-\alpha^2|q-Q/2|^2}{k^2}} \tilde{\eta}(Q, z').$$

For large values of $\alpha$ this integral may be evaluated asymptotically. The integrand, modulo the Gaussian, may be expanded in a Taylor series around the point $q=Q/2$, $$\frac{e^{i[k_z(q)+k_z(q-Q/2)](z_0-z')}}{k_z(q)} = \qquad (34)$$

$$\frac{e^{2ik_z(Q/2)(z'-z_0)}}{k_z(Q/2)} + q \cdot \nabla_q \frac{e^{i[k_z(q)+k_z(q-Q/2)](z_0-z')}}{k_z(q)} \bigg|_{q=Q/2} + \ldots$$

Replacing this part of the integrand, the leading term is given by an integral over the constant term in the Taylor expansion:

$$\tilde{S}(Q, k) = \qquad (35)$$

$$i2\pi A(k) e^{\frac{-\alpha^2 Q^2}{4k^2}} \int dz' \frac{e^{2ik_z(Q/2)(z'-z_0)}}{k_z(Q/2)} \int d^2 q e^{\frac{-\alpha^2|q-Q/2|^2}{k^2}} \tilde{\eta}(Q, z').$$

The Gaussian integral may be easily carried out and the remaining integral is seen to be a Fourier transform with respect to $z'$, $$\tilde{S}(Q, k) = \frac{k^2}{\alpha^2} i2\pi^2 A(k) \frac{e^{-2ik_z(Q/2)z_0}}{k_z(Q/2)} e^{\frac{-\alpha^2 Q^2}{4k^2}} \tilde{\tilde{\eta}}[Q, -2k_z(Q/2)], \qquad (36)$$

where $\tilde{\tilde{\eta}}$ is the three-dimensional Fourier transform of $\eta$. The next term in the expansion yields a contribution proportional to $\alpha^{-4}$. In the extreme limit that NA→1, it may be seen that $\alpha \to \pi$ so that we expect the leading term approximation to be sufficient even in the case of high numerical aperture. It might be noted that this expansion is distinct from the paraxial approximation (essentially a small $|q|$ expansion of $k_z(q)$) which fails as NA→1.

Eq. (36) expresses a resampling scheme illustrated in FIG. 18. To find an appropriate regularization scheme, we will write $$\tilde{S}(Q, k) = \int d\beta H(Q, k, \beta) \tilde{\tilde{\eta}}(Q, \beta), \qquad (37)$$

where $$H(Q, h, \beta) = \frac{k^2}{\alpha^2} i2\pi^2 A(k) \frac{e^{-2ik_z(\frac{Q}{2})z_0}}{k_z(\frac{Q}{2})} e^{\frac{-\alpha^2 Q^2}{4k^2}} \delta\left[\beta + 2k_z\left(\frac{Q}{2}\right)\right] \qquad (38)$$

$$\equiv f(Q, k, \beta) \delta\left[\beta + 2k_z\left(\frac{Q}{2}\right)\right].$$

Then the kernel of the normal operator is given by the expression $$H^*H(Q, \beta, \beta') \equiv \left|f\left(Q, \frac{1}{2}\sqrt{\beta^2 + Q^2}, \beta\right)\right|^2 \frac{\beta}{2\sqrt{\beta^2 + Q^2}} \delta(\beta - \beta'). \qquad (39)$$

And the kernel of the Tikhonov regularized psuedo-inverse, with white noise N is given by the expression $$H^+(Q, k; \beta) = \frac{f^*(Q, k, \beta)\delta\left(k - \frac{1}{2}\sqrt{\beta^2 + Q^2}\right)}{|f(Q, k, \beta)|^2 + 2Nk/k_z\left(\frac{Q}{2}\right)}. \qquad (40)$$

The object structure is then given by $$\tilde{\tilde{\eta}}^+(Q, \beta) = \left[\frac{f^*(Q, k, \beta)\tilde{S}(Q, k)}{|f(Q, k, \beta)|^2 + 2Nk/k_z\left(\frac{Q}{2}\right)}\right]_{k=\frac{1}{2}\sqrt{\beta^2+Q^2}} \qquad (41)$$

The object structure in the coordinate domain is obtained by applying the three-dimensional inverse Fourier transform.

To achieve phase stability of the signal, a microscope coverslip (not shown) may be placed on top of sample 8 and the top reflection from the air-coverslip interface acts as a fixed reference delay relative to the object. The delay fluctuations of the interferometer are removed from each cross-correlation interferogram by locating the air-coverslip reflection in each interferogram, estimating the phase and group delay of the reflection, and applying the opposite phase and group delay to the entire interferogram. Prior to processing, the spectra, each representing a column of depth-dependent data, are assembled adjacently as the beam is transversely scanned over the sample. The detected digital signal is interpolated to account for the non-uniform sampling of the spectrum and to compensate for up to third-order dispersion. Specifically, the signal is interpolated by a factor of two by a band-limiting interpolator implemented using the fast Fourier transform (FFT). This prepares the signal for the cubic B-spline interpolation, which has a transfer function with an amplitude that attenuates frequencies close to the Nyquist limit. The cubic B-spline interpolator resamples the spectrum to a uniform frequency space according to a calibration procedure utilizing a single reflector placed at the focus of the objective lens. Sample movement, inducing phase and group delay changes, is tracked using a reference microscope coverslip, and the deviations are corrected. At this point, the quantity S(r0, k), in Eq. (1) has been estimated. Next, the two-dimensional FFT in the transverse directions is calculated to yield $\tilde{S}(Q,k)$. Then, the non-uniform ISAM resampling and filtering of Eq. (3) using cubic B-splines is implemented to yield $\tilde{\tilde{\eta}}$. Finally, the 3-D inverse FFT is used to attain the ISAM reconstruction, an estimate of $\eta(r)$.

By application of ISAM techniques as described, in vivo imaging may advantageously be performed on larger volumes of tissue than volumes that would otherwise have to be resected. Furthermore, ISAM achieves high-speed, high-resolution imagery without need for the timely processing, sectioning, and staining of a resection.

With the use of near-infrared light, high-resolution ISAM facilitates the noninvasive monitoring of cellular and nuclear development with penetration depths up to 3 mm. Of course, in regions of extreme scattering or absorption penetration depths may be reduced.

Image formation algorithms are characterized differently than image post-processing routines. In particular, ISAM is a unique image formation method that utilizes the fundamental resolution capabilities of the acquired optical signal based on the physics of the scattering within the detection beam. In contrast, a simple image post-processing algorithm may attempt to extrapolate beyond the information inherent an image. For example, maximum likelihood, blind-deconvolution, or entropy-constrained algorithms can effectively produce energy compaction as an estimated solution to an image reconstruction. Such estimation may incorrectly reconstruct features in an image, thus misrepresenting the true biological structure and potentially leading to an incorrect diagnosis. ISAM is not based on estimation, thus such misrepresentations do not exist. Furthermore, estimation algorithms often exceed the limited computational complexity necessary for real-time imaging. The ISAM image formation algorithm can be implemented with computational complexity of O(N log N), where N is the number of volume elements to resolve, which makes ISAM amenable to real-time imaging. Furthermore, the ISAM algorithm can be applied to planes as well as volumes, thus enhancing cross-sectional imaging.

Azimuthally-Scanned Implementation

Embodiments of the invention are now described in which a focused beam is directed perpendicular to an OCT catheter, which might, for example, be incorporated into an endoscope. An endoscope, used for exploring the tubular lumens within the human gastrointestinal tract, typically consists of a long, flexible device of 1 cm diameter or less. Inside the endoscope, in addition to a source of white light illumination and optics for imaging, for example, on a charge-coupled device (CCD) detector, are working channels through which various instruments for biopsy or manipulating tissue are passed. For example, tissue biopsy samples can be extracted and withdrawn by forceps or suction. Smaller diameter catheters are used in the cardiovascular system, e.g. for the insertion of balloons for angioplasty or to deploy stents. Intravascular catheters minimize invasiveness and provide access to vascular lesions associated with cardiovascular disease.

An azimuthally-scanned OCT system would typically include a working channel containing a single-mode optical fiber, a focusing lens (typically a graded index lens cemented or fused to the fiber), and a right-angle prism or a custom cleaved surface for reflecting the beam by 90 degrees to the side of the catheter.

Fiber-optic OCT catheters have been integrated with endoscopes to image the esophagus, colon, and other internal organs and mucosal tissue, as described, for example, by Tearney et al., In vivo endoscopic optical biopsy with optical coherence tomography, Science, vol. 276, pp. 2037-39 (1997), incorporated herein by reference. In instruments based on fiber-optic OCT, the illumination originates inside the object or tubular lumen being imaged, and is usually scanned azimuthally around the long axis of the catheter. As the catheter is azimuthally scanned and translated along the long-axis of the catheter, a 3-D image of the object is acquired. Because the beam is typically focused at a fixed distance from the catheter, the depth-of-focus of the resulting images is confined to a narrow annulus.

By rotating the catheter about its long-axis, the beam may be directed along any path perpendicular to the axis. By pushing or pulling the catheter, the beam is translated along the long-axis of the catheter. Together these two degrees of freedom enable the instrument to scan a cylindrically shaped volume around the catheter. Typical imaging with this catheter design involves acquisition of axial scans (either in the time or frequency domain) while rotating the catheter through 360 degrees, advancing the catheter a small distance along its long-axis, and repeating the measurement. After acquisition, one possesses a data set parameterized by the illumination frequency (or time delay), the angular coordinate of the catheter during the scan, and the translational position of the catheter along its axis. With our solution of the inverse problem, we infer the object susceptibility from these data.

An algorithm that infers the susceptibility of a scatterer from the signal acquired in angularly scanned OCT is now described. These may be advantageously employed in catheter-based optical coherence tomography, but the scope of the present invention is not limited and may include application in endoscopic or intravascular ultrasound as well. Other applications may include acoustic, sonar, and seismic sensing where the imaged object is close to a focused transducer, and radar sensing of objects near a rotating dish antenna.

The Forward Problem for Azimuthally-Scanned ISAM

In contradistinction to the forgoing discussion wherein the illuminating Gaussian beam was translated in a straight line perpendicular to its axis, in the following discussion, rotation of the Gaussian beam is considered about the origin.

We consider an experiment in which a Gaussian beam originates at a position with Cartesian coordinates (0, p, 0). Let us denote Cartesian coordinates fixed relative to the sample by r=(x, y, z) and let us denote Cartesian coordinates fixed relative to the beam by r'=(x', y', z'). For each fixed axial position of the fiber y=y=p. The beam is directed at an angle θ from the z-axis, and along the z' axis. The coordinates may be related by a rotation matrix R(θ) so that r=R(θ)r' where $$R(\theta) = \begin{pmatrix} \cos\theta & 0 & \sin\theta \\ 0 & 1 & 0 \\ -\sin\theta & 0 & \cos\theta \end{pmatrix}. \tag{42}$$

Figure 24:
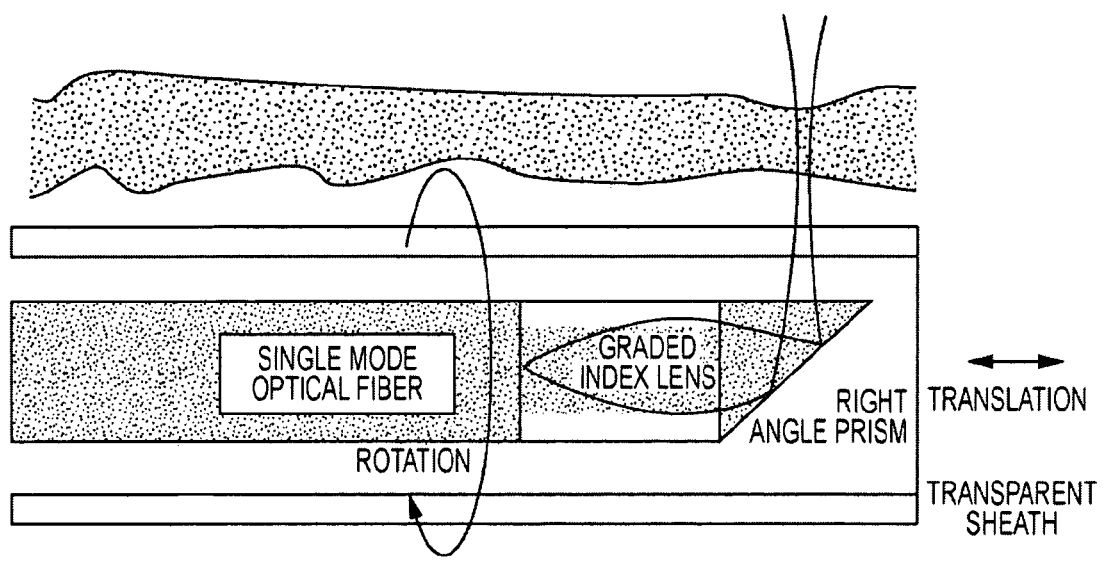
FIG. 24 is a schematic view of an OCT catheter shown in cross-section.
Figure 25:
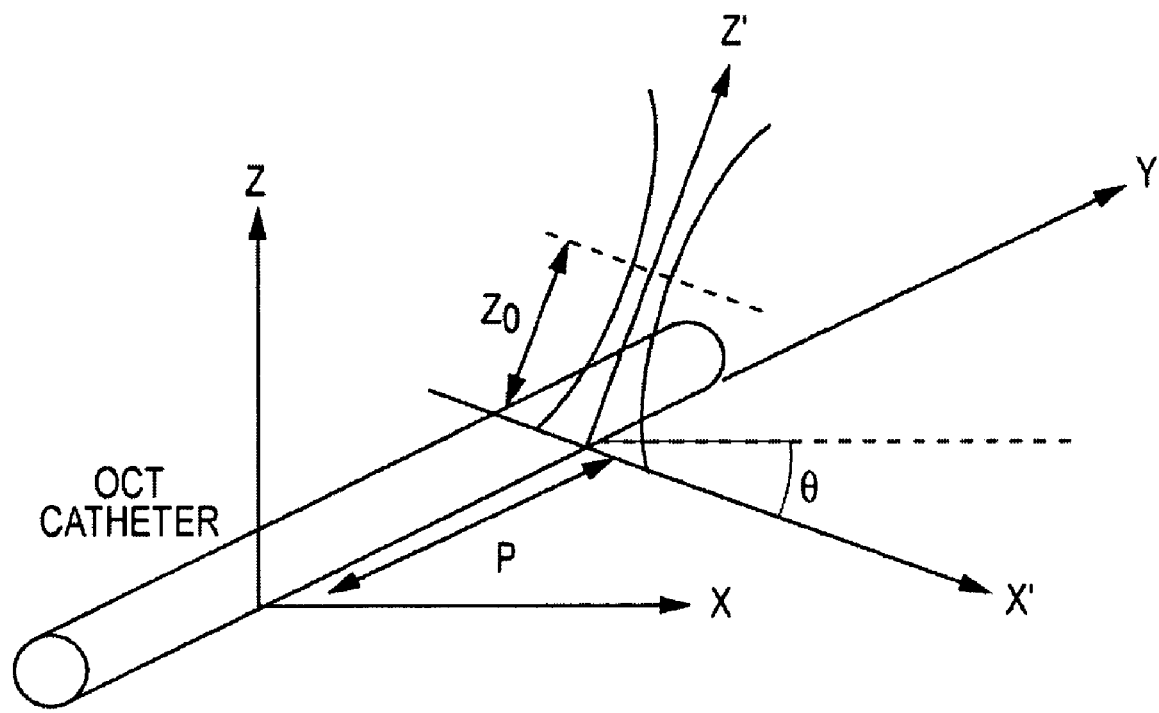
FIG. 25 defines the coordinates used in the description of the OCT catheter.

The beam is focused a distance z0 from the y axis. The field is polychromatic with power spectrum $A^2(k)$ where $k=\omega/c$ is the wave number associated with frequency $\omega$. The width of the beam waist is a function of frequency given by $W(k)=\alpha/k$, where $\alpha=\pi/NA$, and NA, as above, is the numerical aperture of the focused beam. The beam is rotationally scanned so that the signal is sampled for all angles $-\pi \leq \theta < \pi$, and the beam is also translated along the y axis to cover all axial coordinates p. FIG. 24 illustrates this notation.

In the discussion above, it was assumed that the direction of propagation of the beam was fixed to be along the z direction. The location of the center of the beam in the waist plane was given by r0. Then the signal measured in the interferometer is given by the expression $\tilde{S}(r,k)$, which is given by $$\tilde{S}(r, k) = i(2\pi)^{-2} A(k) k^{-1} \int_V d^3 r \, \eta(r) f^2(r - r_0; k), \tag{43}$$

Where $\eta(r)$ is the susceptibility of the sample being probed, $f^2(r';k)$ is given by the expression:

$$f^2(r'; k) = \tag{44}$$

$$\frac{1}{(2\pi)^2} \int d^2 \xi \exp(-i\xi \cdot r') \frac{1}{2} \left( \frac{\alpha^2}{k^2} + \frac{i(z'-z_0)}{k} \right)^{-1} \exp\left(-\frac{\xi^2 \alpha^2}{4k^2}\right)$$

$$\exp\left[i(z'-z_0)\sqrt{(2k)^2 - \xi^2}\right]$$

where $\xi=(\xi_x, \xi_y, 0)$ and the integral is over the $\xi_x$, $\xi_y$ plane. Note that we do not now make the paraxial approximation for the phase term. The signal depends on frequency, position along the y-axis, and the angle of propagation of the beam as described above. This signal, $\tilde{S}(k,p,\theta)$, may be found from Eq. (39) by writing the integrand in the coordinates stationary with respect to the beam. Thus we obtain $$\tilde{S}(k, p, \theta) = i(2\pi)^{-2} A(k) k^{-1} \int_V d^3 r' \eta[R(\theta)r'] f^2(r' - p\hat{y}; k). \tag{45}$$

By substituting Eq. (44) into Eq. (45) and rearranging terms, we find $$\tilde{S}(k, p, \theta) = \frac{i}{2} A(k) k^{-1} \int d^2 \xi \exp\left[-iz_0 \sqrt{(2k)^2 - \xi^2}\right] \tag{46}$$

$$\exp\left(-\frac{\xi^2 \alpha^2}{4k^2}\right) \int d^3 r' \exp[-i\xi \cdot (r' - p\hat{y})]$$

$$\eta[R(\theta)r'] \left[\frac{\alpha^2}{k^2} + \frac{i(z'-z_0)}{k}\right]^{-1} \exp\left[iz' \sqrt{(2k)^2 - \xi^2}\right].$$

In our analysis of the OCT inverse problem on a Cartesian grid, we found that under certain reasonable approximations, the data could be related to the object susceptibility through a resampling scheme in the Fourier domain. We derive a similar relation here. To do so, it will be advantageous to replace $$\left[\frac{\alpha^2}{k^2} + \frac{i(z'-z_0)}{k}\right]$$

with an approximation commensurate with the natural geometry of the problem. Explicitly, we replace z' with $\rho' = \sqrt{z'^2 + x'^2}$. For most OCT systems, the bandwidth is a small fraction of the central frequency and so we replace $$\frac{1}{k^2}$$

with $$\frac{1}{kk_0}.$$

Thus the factor $$\left[\frac{\alpha^2}{k^2} + \frac{i(z'-z_0)}{k}\right]$$

is replaced by $$\frac{1}{k}\left[\frac{\alpha^2}{k_0} + i\left(\sqrt{x'^2 + z'^2} - z_0\right)\right].$$

This expression is slowly varying relative to the rapidly varying phase of the term $\exp[iz'\sqrt{(2k)^2 - \xi^2}]$, and so approximations to it tend not to change the result greatly. With this substitution, $$\tilde{S}(k, p, \theta) = \frac{i}{2} A(k) \int d^2 \xi \exp\left[-iz_0 \sqrt{(2k)^2 - \xi^2}\right] \tag{47}$$

$$\exp\left(-\frac{\xi^2 \alpha^2}{4k^2}\right) \int d^3 r' \exp[-i\xi \cdot (r' - p\hat{y})]$$

$$\eta[R(\theta)r'] \left[\frac{\alpha^2}{k_0} + i(\rho' - z_0)\right]^{-1} \exp\left[iz' \sqrt{(2k)^2 - \xi^2}\right].$$

To evaluate this integral, we change variables in the inner integral to the coordinates stationary in the reference frame of the sample, $$\tilde{S}(k, p, \theta) = \frac{i}{2} A(k) \tag{48}$$

$$\int d^2 \xi \exp\left[-iz_0 \sqrt{(2k)^2 - \xi^2}\right] \exp\left(-\frac{\xi^2 \alpha^2}{4k^2}\right) \exp(i\xi_y p) \int d^3 r \exp$$

$$\left\{-i[\xi - \hat{z}\sqrt{(2k)^2 - \xi^2}] \cdot R[(-\theta)r]\right\} \eta(r) \left[\frac{\alpha^2}{k_0} + i(\rho - z_0)\right]^{-1},$$

where $\rho = \rho' = \sqrt{x^2 + z^2}$. It may be seen that the integral over r results in a Fourier transform if we note that $[\xi - \hat{z}\sqrt{(2k)^2 - \xi^2}] \cdot R(-\theta)r = R(\theta)[\xi - \hat{z}\sqrt{(2k)^2 - \xi^2}] \cdot r$, after which we obtain $$\tilde{S}(k, p, \theta) = \tag{49}$$

$$\frac{i}{2} A(k) \int d^2 \xi \exp\left[-iz_0 \sqrt{(2k)^2 - \xi^2}\right] \exp\left(-\frac{\xi^2 \alpha^2}{4k^2}\right) \exp(i\xi_y p)$$

$$\tilde{\eta}\{-R(\theta)[\xi - \hat{z}\sqrt{(2k)^2 - \xi^2}]\}$$

where $\tilde{\eta}(\beta)$ is the weighted Fourier transform of $\eta(r)$ given by $$\tilde{\eta}(\beta) = \int d^3 r \exp(ir \cdot \beta) \eta(r) \left[\frac{\alpha^2}{k_0} + i(\rho - z_0)\right]^{-1}. \tag{50}$$

To change the integral over $\xi$ to a cyclic convolution, we make the substitution $\sqrt{(2k)^2 - \xi_y^2} \cos\phi = \xi_x$ so that $\sqrt{(2k)^2 - \xi_y^2} \sin\phi = \sqrt{(2k)^2 - \xi^2}$, after which we obtain $$\tilde{S}(k, p, \theta) = \frac{i}{2} A(k) \int d\xi_y \exp(i\xi_y p) \int_0^\pi d\phi \tag{51}$$

$$\left\{\left[\sqrt{(2k)^2 - \xi_y^2} \sin\phi\right] \exp\left[-iz_0 \sqrt{(2k)^2 - \xi^2}\right] \exp\left(-\frac{\xi^2 \alpha^2}{4k^2}\right)\right\}$$

$$\tilde{\eta}\{-R(\theta)[\hat{x}\cos\phi\sqrt{(2k)^2 - \xi_y^2} + \hat{y}\xi_y - \hat{z}\sin\phi\sqrt{(2k)^2 - \xi_y^2}]\}.$$

For brevity, we define the kernel function $K(k, \xi_y, \phi)$.

$$K(k, \xi_y, \phi) = \tag{52}$$

$$\frac{i}{2} A(k) \left[\sqrt{(2k)^2 - \xi_y^2} \sin\phi\right] \exp\left[-iz_0 \sqrt{(2k)^2 - \xi^2}\right] \exp\left(-\frac{\xi^2 \alpha^2}{4k^2}\right).$$

We note that the cos φ next to x and the sin φ next to $\hat{z}$ in Eq. (51) effect a rotation in the x-z plane through an angle −φ of a vector $\hat{x}\sqrt{(2k)^2-\xi_y^2}$. Given this, we can express Eq. (51) as a cyclic convolution:

$$\tilde{S}(k,p,\theta) = \int d\xi_y \exp(i\xi_y p) \quad (53)$$

$$\int_0^\pi d\phi K(k,\xi_y,\phi)\tilde{\eta}\{-R(\theta-\phi)[\hat{x}\sqrt{(2k)^2-\xi_y^2}+\hat{y}\xi_y]\}.$$

By combining the rotations R(θ) and R(−φ), we find the integral over φ is a cyclic convolution. This cyclic convolution can be performed efficiently using the product of Fourier series. To put Eq. (51) into diagonal form, we define the following functions of the data, the kernel, and the structure function:

$$\tilde{\tilde{S}}(k,\xi_p,n_\theta) = \int_{-\infty}^\infty \int_{-\pi}^\pi dp\, d\theta \exp(ip\xi_p)\exp(i\theta n_\theta)\tilde{S}(k,p,\theta), \quad (54)$$

$$\tilde{\tilde{K}}(k,\xi_y,n_0) = \int_0^\pi d\theta \exp(i\theta n_\theta)K(k,\xi_y,\theta), \quad (55)$$

$$\tilde{\tilde{\eta}}(k,\xi_y,n_\theta) = \int_{-\pi}^\pi d\theta \exp(i\theta n_\theta)\tilde{\eta} \quad (56)$$

$$\{-[\hat{x}\cos\theta\sqrt{(2k)^2-\xi_y^2}+\hat{y}\xi_y+\hat{z}\sin\theta\sqrt{(2k)^2-\xi_y^2}]\}.$$

Where $n_\theta$ is an integer on $[-\infty,\infty]$. If we insert the definitions of Eqs. (36)-(38) into Eq. (35), we find the following relationship:

$$\tilde{\tilde{S}}(k,\xi_p,n_\theta)=\tilde{\tilde{K}}(k,\xi_p,n_\theta)\tilde{\tilde{\eta}}(k,\xi_p,n_0). \quad (57)$$

In this form we see that $\tilde{\tilde{S}}$ and $\tilde{\tilde{\theta}}$ are related by a diagonal integral operator whose kernel is $\tilde{\tilde{K}}(k',\xi_{p'},n_{\theta'})\delta(k-k')\delta(\xi_p-\xi_{p'})\delta_{n_\theta,n_{\theta'}}$. Explicitly $S=\hat{K}\tilde{\tilde{\theta}}$ where $\hat{K}$ is the integral operator $$[\hat{K}\tilde{\tilde{\eta}}](k,\xi_p,n_\theta) = \int dk' \int d\xi_{p'} \quad (58)$$

$$\sum_{n_\theta} \tilde{\tilde{K}}(k',\xi_{p'},n_{\theta'})\delta(k-k')\delta(\xi_p-\xi_{p'})\delta_{n_\theta,n_{\theta'}}\cdot \tilde{\tilde{\eta}}(k',\xi_{p'},n_{\theta'}).$$

This diagonal operator will simplify finding solutions to specific inverse problems.

The Inverse Problem for Azimuthally-Scanned ISAM

Eq. (57) defines a linear relationship between the object structure and data. To better understand how to invert this relationship, the relationship between the data $\tilde{S}(k,p,\theta)$ and the object η(r) is written explicitly:

$$\tilde{S}(k,p,\theta) = \frac{1}{4\pi^2}\int d\xi_y \exp(-i\xi_y p) \quad (59)$$

$$\sum_{n_\theta=-\infty}^\infty \exp(-i\theta n_\theta)K(k,\xi_y,n_\theta)\int d^3r\eta(r)\left[\frac{\alpha^2}{k_0}+i(\rho-z_0)\right]^{-1}$$

$$\int_{-\pi}^\pi d\phi \exp(i\phi n_\theta)\exp\{-ir\cdot R(\phi)[\hat{x}\sqrt{(2k)^2-\xi_y^2}+\hat{y}\xi_y]\}$$

Where $\tilde{K}(k,\xi_p,n_\theta)$ is given explicitly by $$\tilde{K}(k,\xi_p,n_\theta) = \frac{i}{2}A(k)\int_0^\pi d\theta \exp(i\theta n_\theta)\exp\left[-\frac{(2k)^2\cos^2\theta+\xi_p^2\sin^2\theta}{2}\frac{\alpha^2}{2k^2}\right] \quad (60)$$

$$\exp[-iz_0\sin\theta\sqrt{(2k)^2-\xi_p^2}]\sqrt{(2k)^2-\xi_p^2}\sin\theta.$$

Eq. (59) can be rewritten to use a Fredholm-type kernel κ(k, p, θ, r) Such that $$S(k,p,\theta)=\kappa\eta=\int d^3r\kappa(k,p,\theta,r)\eta(r). \quad (61)$$

Although Eq. (61) may not be strictly solvable, a least-squares solution $\eta^+$ can be found by minimizing a functional:

$$\eta^+ = \underset{\eta}{\mathrm{argmin}}|S-\kappa\eta|^2 \quad (62)$$

$$= \underset{\eta}{\mathrm{argmin}}\int_0^\infty dk\int_{-\infty}^\infty dp\int_{-\pi}^\pi d\theta|S(k,p,\theta)-\kappa\eta(r)|^2.$$

The least-squares solution is then given by the pseudo-inverse $\eta^+=(\kappa^\dagger\kappa)^{-1}\kappa^\dagger S$. While this solution is formally correct, the inverse $(\kappa^\dagger\kappa)^{-1}$ can be difficult to compute in practice. Instead, we find the least-squared error solution for the weighted Fourier transform $\tilde{\tilde{\eta}}^+$ that, while not directly minimizing the error relative to the measurements, still constrains the estimated object structure to be consistent with the data:

$$\tilde{\tilde{\eta}}^+ = \underset{\tilde{\eta}}{\mathrm{argmin}}|S-K\tilde{\tilde{\eta}}|^2+\lambda|\tilde{\tilde{\eta}}|^2 = \quad (63)$$

$$\underset{\tilde{\eta}}{\mathrm{argmin}}\int_0^\infty dk\int_{-\infty}^\infty d\xi_p \sum_{n_\theta=-\infty}^\infty |\tilde{\tilde{S}}(k,\xi_p,n_\theta)-K(k,\xi_p,n_\theta)|^2 +$$

$$\lambda|\tilde{\tilde{\eta}}(k,\xi_p,n_\theta)|^2.$$

This least-squares solution keeps the object estimate consistent with Eq. (57). Also included is a Tikhonov regularization term to stabilize the solution, with regularization parameter λ. The solution $\tilde{\tilde{\eta}}^+$ is:

$$\tilde{\tilde{\eta}}^+(k,\xi_p,n_\theta) = \frac{\tilde{\tilde{S}}(k,\xi_p,n_\theta)K^*(k,\xi_p,n_\theta)}{|K(k,\xi_p,n_\theta)|^2+\lambda}. \quad (64)$$

This least squares solution is a numerically simpler method of estimating the object structure. Starting with data given by S(k,p,θ), we can compute $\tilde{\tilde{S}}(k,\xi_p,n_\theta)$ using Eq. (52). Using Eq. (64) one can compute $\tilde{\tilde{\eta}}^+(k,\xi_p,n_\theta)$. Then Eq. (56) can be solved for $\tilde{\eta}^+$ by taking the discrete inverse Fourier transform of $\tilde{\tilde{\eta}}^+$ with respect to $n_\theta$. Finally, a 3-D inverse Fourier transform computes $\eta^+(r)$ from $\tilde{\eta}^+$. In the limit that λ→0 and all data are continuously available, this approach yields an exact solution for η(r). In the more realistic scenario that a regularized solution is employed, a stable solution is obtained.

Simulation of Azimuthally-Scanned ISAM

As in the full-field OCT embodiment discussed above, the azimuthally-scanned algorithmic embodiment is now demonstrated by implementing a simulation of the forward and inverse scattering in the radial OCT geometry. A synthetic object was created comprised of pointlike scatterers. The simulated OCT data were calculated from the exact forward problem using Eq. (45), and then the regularized solution of the inverse scattering solution was calculated using Eq. (64). The simulation is of a pseudo-three-dimensional object that is invariant along the y-axis, so that the object is effectively two-dimensional.

The simulation was performed with lengths in units of the central wavelength of the illumination. Typical center wavelengths for OCT imaging are between 800 nm and 1400 nm. The cross-section of the simulated object was taken to be approximately 135 by 135 wavelengths. The Gaussian illumination beam was assumed to be focused 45 wavelengths from the origin, with a beam waist width of 2.5 wavelengths. The scatterers were placed 15 to 60 wavelengths from the origin at randomly selected angles relative to the x-axis. The simulated source was taken to have a Gaussian spectrum with a full-width-half-maximum (FWHM) fractional bandwidth of approximately 25%. Each of the scatterers had the same susceptibility.

Figure 26A:
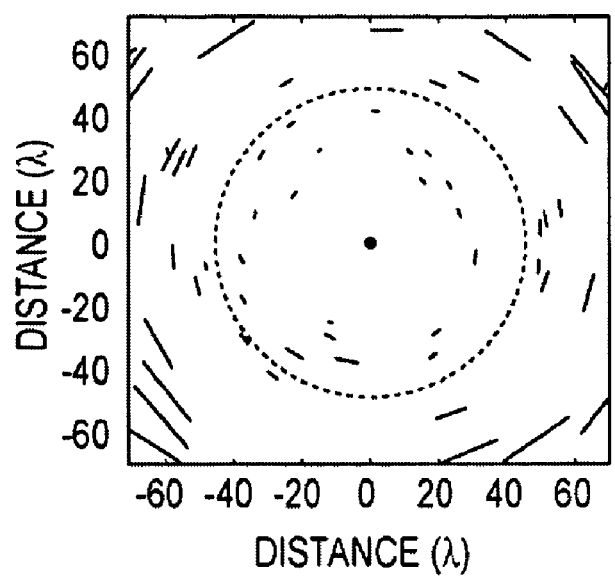
FIG. 26(*a*) is simulated OCT for randomly scattered point objects and FIG. 26(*b*) is a reconstruction of the point sources from the simulated data.

The forward scattering problem was implemented by directly summing the contribution of each point scatterer individually using Eq. (45). This was achieved by summing for each sampled data point $\tilde{S}(k,\theta)$ the total collected backscattered amplitude for all of the scatterers at their respective positions r' the amplitude $f^2(r';k)$ as specified in Eq. (44). Note that in Eq. (44) the exact phase rather than the Fresnel quadratic approximation was used to more accurately compute the data for a high numerical aperture beam. To show the equivalent OCT image, the data was inverse Fourier transformed along the k axis, yielding $S(r,\theta)$. The resulting $S(r,\theta)$ is displayed in a polar plot in FIG. 26(a).

The dotted circle in the diagram indicates the radius at which the Gaussian beam is focused. Note that the images of points located closer to the origin than the focus (inside the circle) curve towards the origin, and the points located further from the origin than the focus curve (outside the circle) away from the origin, as would be expected.

The inverse scattering problem was implemented using the approximate solution embodied in Eq. (64). The data is given as $\tilde{S}(k,\theta)$. To utilize Eq. (64), several Fourier transform steps were needed. The inverse scattering algorithm was implemented using the following steps:

The data $\tilde{S}(k,\theta)$ was Fourier transformed with respect to $\theta$ to yield $\tilde{\tilde{S}}(k,n_\theta)$.

The function $\tilde{K}(k,\theta)$ was calculated (using $\xi_p=0$) and then Fourier transformed with respect to $\theta$ to yield $\tilde{\tilde{K}}(k,n_\theta)$ as per Eq. (61).

The regularized $\tilde{\tilde{\eta}}^+(k,n_\theta)$ was calculated using Eq. 65.

$\tilde{\tilde{\eta}}^+(k,n_\theta)$ was inverse Fourier transformed with respect to $n_\theta$ yield $\tilde{\eta}^+(k,\theta)$.

The $\tilde{\eta}^+(k,\theta)$ was inverse Fourier transformed with respect to k to yield $\eta_R^+(l,\theta)$, the Radon transform of $\eta^+(x,z)$.

The inverse Radon transform of $\eta_R^+(l,\theta)$ was performed to yield $\eta^+(x,z)$, the Tikhonov-regularized inverse.

The inverse Radon transform was used as a convenient way to convert from the polar representation of the Fourier transform $\tilde{\eta}^+(k,\theta)$ to its inverse Fourier transform Cartesian counterpart $\eta^+(x,z)$, using the Fourier projection slice theorem. Unfortunately, many implementations of the inverse Radon transform, such as the filtered-backprojection method that was used for this simulation, are slow, and therefore care will need to be exercised to ensure that the computational burden is not too great. Methods exist to implement the inverse Radon transform in $O(N^2 \log N)$ time, rather than the $O(N^3)$ typical of most filtered-backprojection inverse Radon transform methods.

Figure 26B:
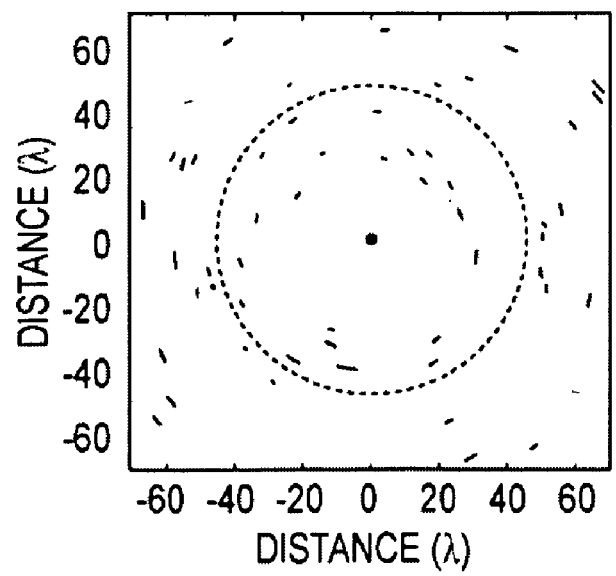

The results of the inverse scattering computation are shown in FIG. 26(b). As can be seen, the blurred arcs corresponding to the point sources in the uncorrected OCT data are corrected to be pointlike when inverse scattering is performed on the data. The algorithm correctly compensates for the range-dependent blur and curvature of the backscattered signal. Unlike in the translationally-scanned Gaussian beam or the full-field cases, the reconstructed image does not exhibit uniform resolution. The resolution of the reconstruction depends on the distance from the origin. Because the beam width is wide near the origin, points nearer the origin than the focus are overlapped by the beam for many angles $\theta$, so that the resolution of points near the origin is high. At the focus, the beam width is narrow and so points near the focus are also resolved well. Far from the origin, the beam is wide and points are only overlapped by the beam for a narrow range of angles given by the divergence of the beam, so that the resolution degrades with distance from the origin. Generally, the resolution is nearly constant between the origin and the focus radius, and slowly degrades to a constant angular resolution at radii further than the focus. Therefore, the most useful resolution will be achieved for distances at or closer than the focus radius.

Figure 27:
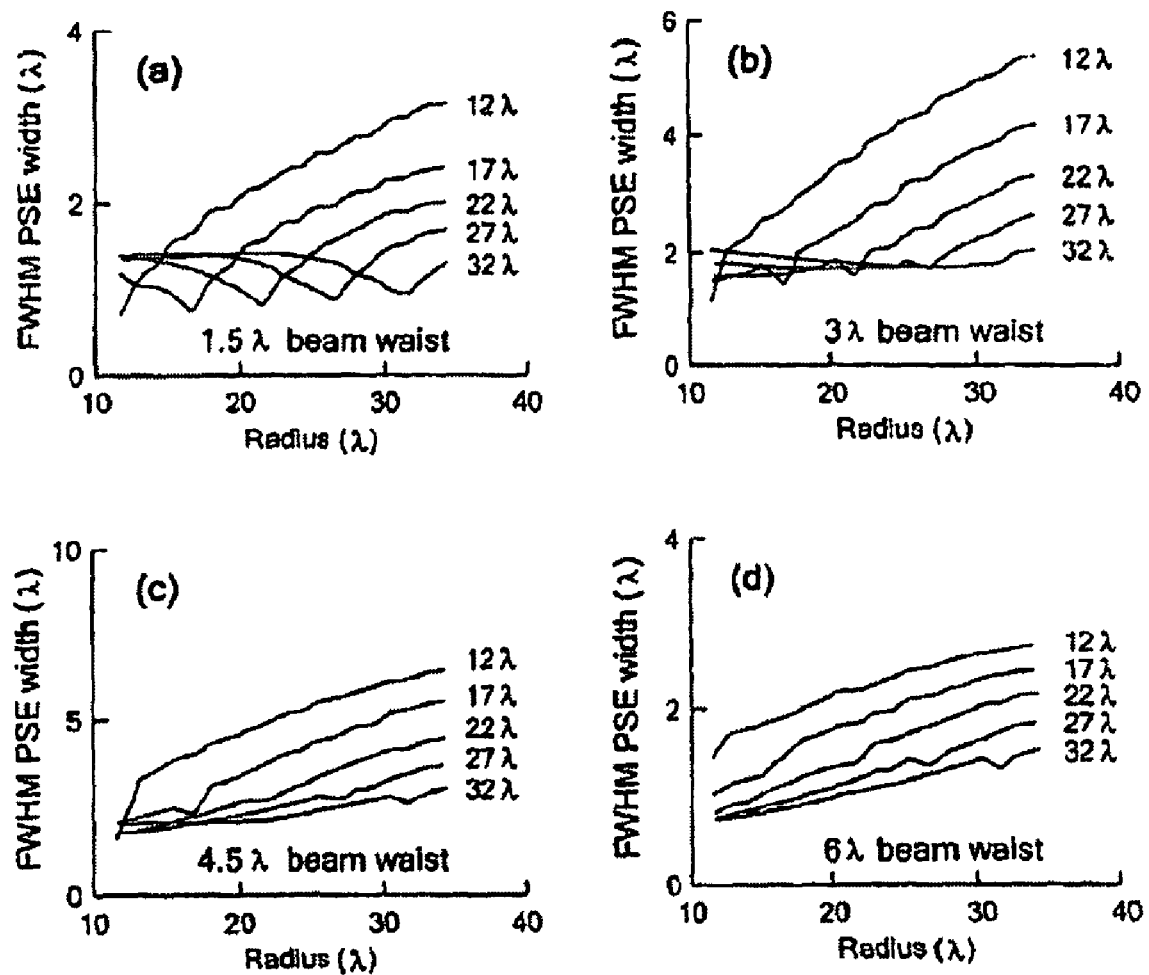
FIG. 27 is a plot depicting full-width-half-maximum transverse point-spread-function (PSF) resolution of simulated point sources situated at different distances from the catheter axis, as a function of focus radius and beam width. The abscissa is the distance from the origin from which the simulated point source is placed. In each part, the number next to each curve is the distance away from the origin the beam was focused. The beam waist for each part is (a) $1.5\lambda$, (b) $3\lambda$, (c) $4.5\lambda$, and (d) $6\lambda$.

To explore the range-dependent resolution further, a simulation of point scatterers reconstructed with beams with various widths and focus radii is now described with reference to FIG. 27. FIG. 27 has four parts, each of which is the simulated resolution of point scatterers for beams of different widths. The marking next to each curve is the focus radius for each simulated beam. The resolution is measured as the FWHM of the reconstructed point in the angular direction. Each graph relates the FWHM resolution to the distance from the axis to the simulated point. For small beam waists, as in parts (a), (b), and (c), the resolution is approximately constant for radii closer than the focus radius. Further than the focus the FWHM resolution starts to increase. For the wider beams, the transverse resolution near the origin can be somewhat better than the width of the beam waist.

Figure 28:
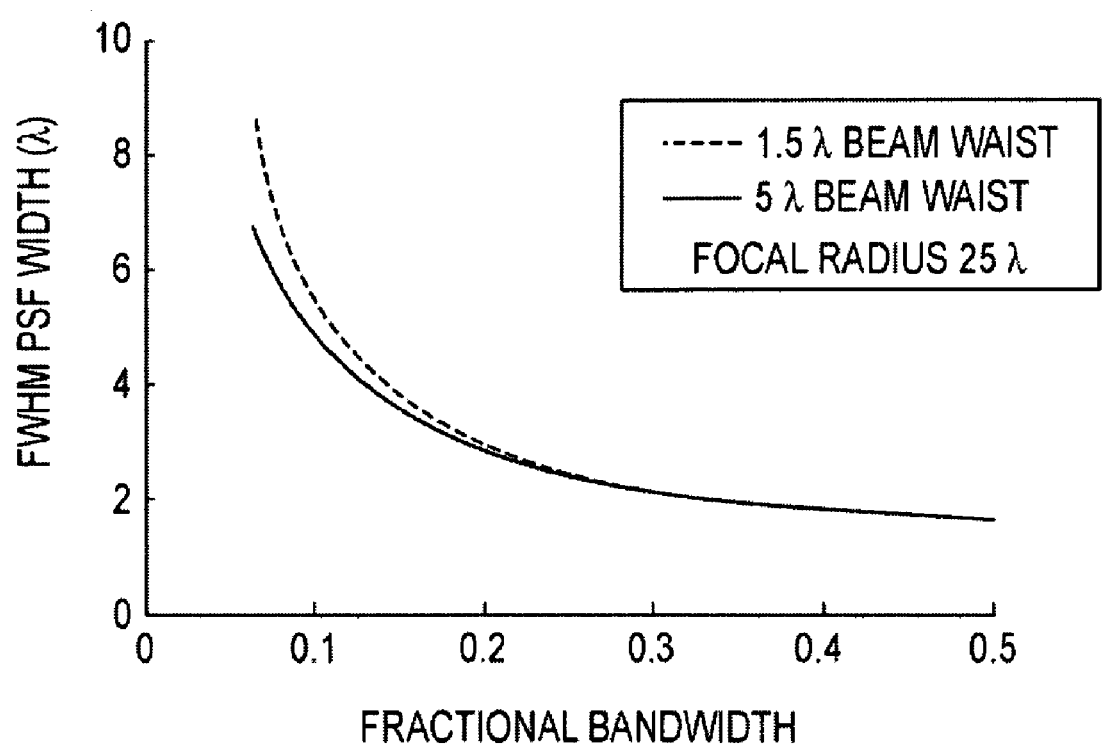
FIG. 28 is a plot depicting full-width-half-maximum axial resolution of simulated point sources imaged with two different beam widths focused 25 wavelengths from the catheter axis, for various fractional bandwidths of the source. The dotted curve corresponds to a $1.5\lambda$ beam waist, while the solid curve corresponds to a $5\lambda$ beam waist.

To examine the validity of the approximation made in Eq. 47 of small fractional bandwidth, we simulate the reconstruction of point scatterers imaged with various source bandwidths. The simulated focus radius is 25 wavelengths, and the beam widths are 1.5 and 5 wavelengths. FIG. 28 shows the FWHM axial resolution as a function of fractional bandwidth. The resolution should be approximately half the reciprocal of the fractional bandwidth, to which the simulation conforms.

Phase Stability in ISAM

The increased resolution gained by the ISAM solution relies upon phase stable measurements. The phases in cross-correlation signals correspond to the measured relative delay between the reference and sample signal at particular temporal frequencies of the illumination. The aforementioned methods rely on the phases of the cross-correlation measurements for a particular data set to correspond, i.e. the relative delays measured for various positions of the illumination beam need to reflect the true delays for the beam to scatter off of layers inside the object. Unfortunately, because of motions and changes in the object during the data acquisition, and thermal fluctuations that cause object dimensions to change, these delays can vary during the data acquisition interval. This is a problem for almost all computed imaging modalities, but can be exacerbated for optical imaging because the small size of the illumination wavelength (often less than a micron) means that very small motions can cause relatively large fluctuations in phase. If the data acquisition is brief, and the reference delay mechanism can produce a reliably repeatable delay to an accuracy of less than a wavelength, then phase stability between measurements can be easily achieved. For example, with the use of spectral detection for OCT, spectral-domain OCT (SD-OCT) seen in FIG. 23, we can be assured of phase stability within each axial data set because the reference mirror is typically fixed and the data acquisition is very rapid, typically occurring in fractions of a second. Specifically, each axial acquisition is determined directly from Fourier transform of the ensemble of spectral intensity measurements over the duration of the exposure time on a CCD camera. Thus, relative phases between adjacent reflections in the sample are fixed relative to each other and the reference for a single axial acquisition. Furthermore, if adjacent axial scans may be captured fast enough to avoid some minimum amount of phase drift then an accurate reconstruction is possible. Phase drift can occur in a system for multiple reasons including thermal changes, galvanometer or stage positioning accuracy, and system or sample jitter. The greater the time interval between scans, the more likely it is that random phase errors will occur. Adjacent axial scans in a single cross-sectional scan are thus less likely to suffer from distortions due to random phase jitter than adjacent axial scans from multiple cross-sectional scans.

Object reconstruction requires the phase to be stable relative to all axial scans of a 3D acquisition. There are several ways to achieve phase stability, whether it is one of many hardware and environmental configurations, implementations of reference objects, or algorithmic developments based on priors. In conventional scanned beam OCT, it has been shown by Ralston et al., Phase Stability Technique for Inverse Scattering in Optical Coherence Tomography, IEEE International Symposium on Biomedical Imaging., pp. 578-581, (2006), incorporated herein by reference, that one such possible method to achieve 3D phase stability in OCT for reconstruction of the inverse scattering solution is to use a flat reference reflector such as a microscope coverslip. Because the coverslip typically remains in contact with the object, its position relative to the object is fixed, and therefore can serve to indicate a delay that is consistent between axial scans. Such a method offers advantages over expensive environmental controllers and extremely fast acquisition hardware. Further, we develop an algorithm for tracking the air-glass interface. Other interfaces that are fixed relative to the object being measured can also be used, such as the interior or exterior surface of the transparent wall of a catheter.

The acquired SD-OCT signal can be represented after dispersion correction as a function of transverse position and wave number, $S(r_0,k)$, where the wave numbers k are related to the frequencies ω by the dispersion relation $k(\omega)=\omega n/c$, and n is the index of refraction.

We present a method that analyzes each axial scan individually and applies a phase to compensate variations of the position of the sample relative to the illumination beam. We place a reflective surface such as a microscope coverslip on top of the sample to act as a reference surface, which is used to infer the delay to the top surface of the sample. The signal for an arbitrary axial line of data can be represented as S(k), a function of k. We assume that there is a range of distances along the illumination beam zmin to zmax for which the signal reflected from the coverslip is known to reside in every axial scan. The inverse Fourier transform of S(k) is computed as Sc(z), and the signal corresponding to the reflection is contained in the samples Sc(z) for zmin<z<zmax. The spatial spectrum of the reflection is computed as the Fourier transform of Sc(z) over the window zmin<z<zmax, which is called $\tilde{S}_c(k)$.

Because the signal contained in $\tilde{S}_c(k)$ corresponds to a single reflection, it is reasonable to model it as $\tilde{S}_c(k)=A(k)e^{i\phi(k)}$, where the phase function $\phi(k)=\phi_0+kd$, where $\phi_0$ is an arbitrary phase and d is the true position of the surface where the reference reflection occurs. Because of the motion of the sample, the actual phase arg $\tilde{S}_c(k)=\phi'(k)$. By multiplying the axial scan data S(k) by the correction factor $e^{i[\phi(k)-\phi'(k)]}$, the phase of the axial scan can be adjusted to place the reflection at its true known position d.

We model the phase $\phi'(k)$, as a Taylor series around a center frequency $k_0$:

$$\phi'(k) = \phi'(k_0) + (k-k_0)\frac{\partial \phi'}{\partial k}\bigg|_{k=k_0} + \ldots,$$

To utilize this model, we must estimate the value of $\partial\phi'/\partial k|_{k=k_0}$ from the data function $\phi'(k)$. The function $\phi'(k)$ is wrapped to the range $-\Box$ to $\Box$, so calculating the derivative directly from the wrapped data will incorrectly incorporate the $2\Box$ jumps into the estimate. Instead, we form the unwrapped $\phi_w(k)$ by removing $2\Box$ discontinuities from $\phi'(k)$. The estimate then becomes $$\frac{\partial \phi'}{\partial k}\bigg|_{k=k_0} \approx \frac{\phi_w(k_2)-\phi_w(k_1)}{k_2-k_1}$$

where k1<k0<k2, with the frequencies k1 and k2 chosen to span the illumination spectrum, typically with k1 and k2 corresponding to the frequencies at which the power spectral density is half of that at the peak.

Once $\phi'(k_0)$ and $\partial\phi'/\partial k|_{k=k_0}$ are known, the empirical $\phi'(k)$ can be computed, and the corrected axial scan spectrum $S'(k)=S(k)e^{i[\phi(k)-\phi'(k)]}$. This corrected axial scan data will be modified such that the position of the reference reflection is always at the same location on the axial scan, removing the effective longitudinal relative motion between the sample and the scanned beam. For this method to work properly, the reference object must be located for each axial scan, otherwise that axial scan could contribute to a poor reconstruction. Furthermore, refinements to this method could utilize higher order terms of the series for $\phi'(k)$, which would account for instrument dispersion as well as motion.

Experimental Examples of ISAM Imaging

Figure 29:
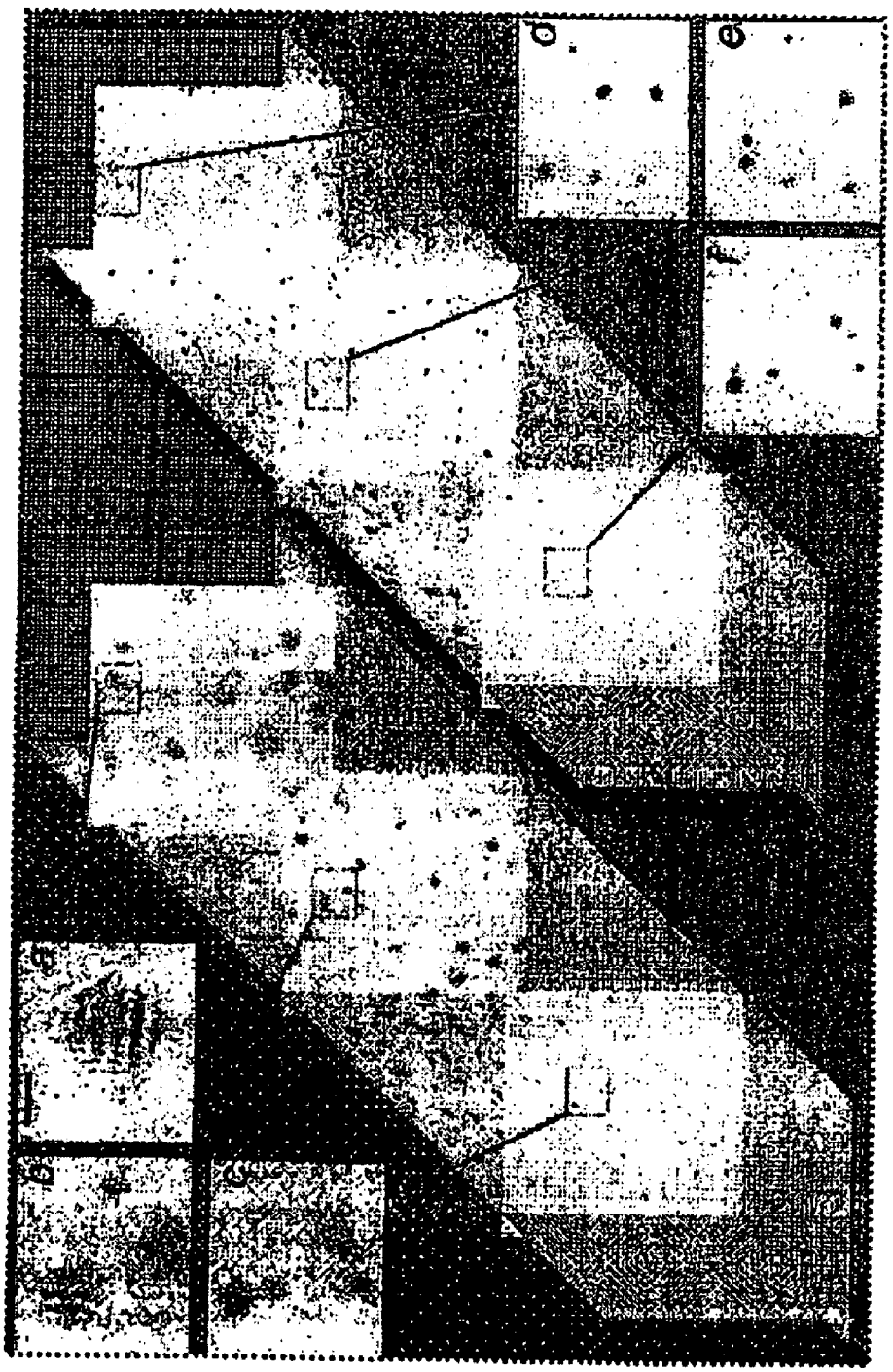
FIG. 29 shows interferometric data from a tissue phantom consisting of titanium dioxide scatterers suspended in silicone. Planar slices the 3-D unprocessed data (left) and ISAM reconstruction (right) are shown for two en face planes above the focus and one below the focus. Magnified unprocessed sections for three depths are shown in (a) at z=1100 µm, (b) at z=475 µm, and (c) at z=−240 µm, where z=0 µm is the focal plane. Magnified ISAM reconstructions for these corresponding planes are shown in (d), (e), and (f), respectively. The scale bar represents 18 µm.

A tissue phantom consisting of a collection of titanium dioxide scatterers having a mean diameter of 1 μm and uniformly suspended in silicone was imaged using low-coherence interferometry and a 0.05 NA objective. FIG. 29 displays cross-sections through an unprocessed data set (left) and ISAM reconstruction (right) of a volume 360 μm×360 μm (transverse)×2000 μm (axial). FIG. 29a-f contain three pairs of en face sections for both the unprocessed data (FIG. 29a-c) and the ISAM reconstructions (FIG. 29d-f). The distances from the en face section planes to the focus, located at z=0, are z=1100 μm (FIG. 29a and 29d), z=475 μm (FIG. 29b and 29e), and z=−240 μm (FIG. 29c and 29f). These sections show that the reconstruction has resolved the scatterers throughout a range of depths over nine times the Rayleigh range from the focus, where the Rayleigh range is commonly defined as half of the depth-of-field, or what is considered in-focus in optical imaging systems. In the unprocessed data, the interference between the signals scattered from adjacent scatterers is evident. Our method properly accounts for the diffraction of the beam, and so separates the superimposed signals from the scatterers to form well-resolved point images on all planes.

Figure 30:
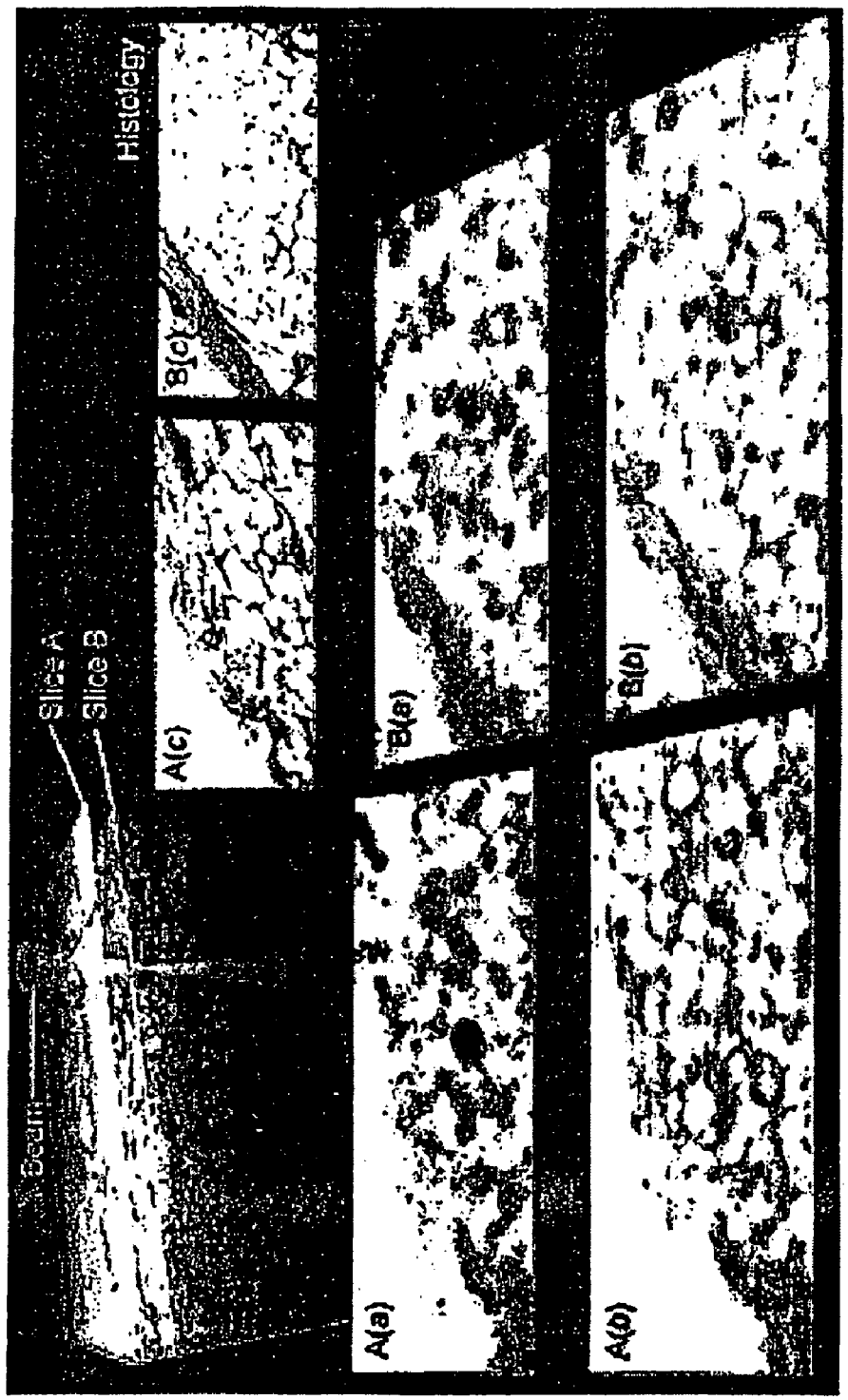
FIGS. 30(*a*)-(*c*) show en face images from human breast tissue. (a) Unprocessed interferometric data and (b) ISAM reconstructions are shown for depths located at z=591 µm (Slice A) and z=643 µm (Slice B), where z=0 µm is the focal plane. (c) The corresponding histological sections are shown for comparison.

Human tumor tissue was resected and imaged ex vivo. Sections were marked with India ink after imaging and before embedding to register locations. FIG. 30 includes en face planes (Slices A and B) of the unprocessed data (FIG. 30a) where the beam diffraction effects are evident, the computed ISAM reconstructions (FIG. 30b), and images of corresponding registered histological sections (FIG. 30c). Although embedding, sectioning, and staining of tissue can disrupt features to some degree, the registered histological sections provide prominent features for comparison. In the reconstruction, boundaries between adipose cells and the margin between adipose and fibrous tissue are clearly identified, with a strong correspondence to histology. While the histological images were obtained by destroying the sample, ISAM could readily be applied for in vivo applications because signal collection is in the back-scattered epi-direction.

Real-Time Cross-Sectional Processing

In order to provide the benefits of spatially-invariant resolution attainable by means of the hitherto described features of ISAM and to obtain immediate feedback in time-critical situations or for monitoring transient dynamics, methods are now described for real-time realization of ISAM computations.

As described in detail above, an object being imaged by spectral-domain OCT (SD-OCT) has a susceptibility represented by $\eta(r_\parallel, z)$, where $r\parallel$ is the transverse position and z is the longitudinal position. The collected SD-OCT signal is represented by $\tilde{S}(r_\parallel, \omega)$, whose arguments are the transverse position of the beam $r\parallel$ and the frequency $\omega$. After correcting for dispersion, the signal is represented by $\tilde{S}(r_\parallel, k)$, where k is the uniformly spaced wavenumber. The Fourier transform of $\tilde{S}(r_\parallel, k)$ with respect to k is $S(r_\parallel, t)$. Introducing a coordinate change from t to t' such that t'=0 coincides with the delay of the focal plane results in a signal $S(r_\parallel, t')$ The 3-D Fourier transform of $S(r_\parallel, t')$ is $\tilde{\tilde{S}}(Q, k)$.

The algorithm for ISAM is constructed as described above. A solution for high-numerical aperture optics is implemented, namely, a relation is derived that associates the Fourier transform of the object $\eta$ with the Fourier transform of the signal S. The 2-D Fourier transform of the spectral-domain OCT signal $\tilde{S}(r_\parallel, k)$, is given by the expression $$\tilde{\tilde{S}}(Q, k) = \frac{k^2}{\alpha^2} i 2\pi^2 A(k) \frac{e^{-2ik_z(Q/2)z_0}}{k_z(Q/2)} e^{\frac{-\alpha^2 Q^2}{4k^2}} \tilde{\eta}[Q, -2k_z(Q/2)], \quad (65)$$

where $\tilde{\eta}$ is the 3-D Fourier transform of $\eta$, the argument Q is the transverse wavevector, k is the wavenumber, $k_z(q) = \sqrt{k^2 - q^2}$, $z_0$ is the fixed position of the beam focus, A(k) is the square root of the power spectral density, $\alpha = \pi/NA$, and NA is the numerical aperture of the beam. The corresponding Tikhonov regularized solution, $\tilde{\eta}^+$, takes the form $$\tilde{\eta}^+(Q, \beta) = \left[ \frac{f^*(Q, k, \beta) \tilde{\tilde{S}}(Q, k)}{|f(Q, k, \beta)|^2 + 2\lambda k / k_z(Q/2)} \right]_{k=\frac{1}{2}\sqrt{\beta^2 + Q^2}} \quad (66)$$

where $$f(Q, k, \beta) = \frac{k^2}{\alpha^2} i 2\pi^2 A(k) \frac{e^{-2ik_z(Q/2)z_0}}{k_z(Q/2)} e^{\frac{-\alpha^2 Q^2}{4k^2}}, \quad (67)$$

$\beta$ is the longitudinal frequency coordinates of the object, and $\lambda$ is the regularization constant. Rearranging the terms of the Fourier space into multiplicative factors of magnitude, $\tilde{\tilde{B}}(Q,k)$, and phase, $e^{i(2k_z(Q/2)z_0 + \pi/2)}$, the pseudo inverse can be rewritten as $$\tilde{\eta}^+(Q, \beta) = \tilde{\tilde{B}}(Q, k) e^{i(2k_z(\frac{Q}{2})z_0 + \frac{\pi}{2})} \tilde{\tilde{S}}(Q, k) \Big|_{k=\frac{1}{2}\sqrt{\beta^2 + Q^2}}, \quad (68)$$

where $$\tilde{\tilde{B}}(Q, k) = \frac{-\frac{k}{\alpha^2} \pi^2 A(k) e^{\frac{-\alpha^2 Q^2}{4k^2}}}{\frac{k^3}{\alpha^4} \frac{2\pi^4 A^2(k)}{k_z(\frac{Q}{2})} e^{\frac{-\alpha^2 Q^2}{2k^2}} + \lambda}. \quad (69)$$

Without loss of generality, the same origin is designated for the depth coordinates z as the time delay coordinates t. The t=0 delay corresponds to the z=0 plane and coincide at the path length matched delay of the reference. Additionally, for a coordinate change, the t'=0 delay corresponds to the z'=0 plane and coincide at the focal plane, where then $z_0$ will equal zero, and equation (66) reduces to $$\tilde{\eta}^{+'}(Q, \beta) = \tilde{\tilde{B}}(Q, k) e^{\frac{i\pi}{2}} \tilde{\tilde{S}}(Q, k) \Big|_{k=\frac{1}{2}\sqrt{\beta^2 + Q^2}}. \quad (70)$$

Figure 32A:
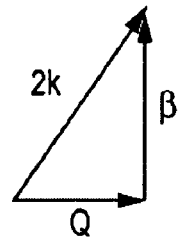
FIG. 32(*a*) depicts the relation between spatial frequencies of the signal space and spatial frequencies in the object space.
Figure 32B:
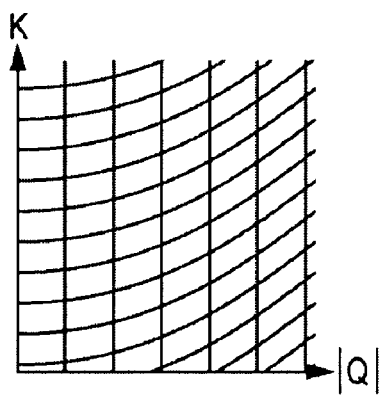

A coordinate change from t to t' is achieved by circularly shifting the data. The origin of the t coordinates is at the time corresponding to the arrival of the reference light. The origin of the t' coordinates is shifted such that t'=0 is at the focal plane. A zero pad of 2|t0| rows prevents aliasing of the shifted data, where t0 is the number of delay samples from the focus to t'=0. The model in FIG. 32(a) and the grid in FIG. 32(b) and (c) describe visually in 2D the ISAM resampling seen in equation (70).

A shift of t0 in $S(r_\parallel, t)$ is used to make the t=0 delay coincide with the z=0 plane as will be seen in the algorithm. $S(r_\parallel, t+t_0)$ has the Fourier transform relation $\tilde{\tilde{S}}(Q,k)e^{-ikt_0}$. If we substitute this into the equation.

$$\tilde{\eta}^+(Q, \beta) = \tilde{\tilde{B}}(Q, k) i e^{2ik_z(\frac{Q}{2})z_0} \tilde{\tilde{S}}(Q, k) e^{-ikt_0} \Big|_{k=\frac{1}{2}\sqrt{\beta^2 + Q^2}} \quad (71)$$

$$\tilde{\eta}^+(Q, \beta) = \tilde{\tilde{B}}(Q, k) i e^{i\{2k_z(\frac{Q}{2})z_0 - kt_0\}} \tilde{\tilde{S}}(Q, k) \Big|_{k=\frac{1}{2}\sqrt{\beta^2 + Q^2}} \quad (72)$$

This equation may be simplified by having the relative time offset $t_0$ and the focus offset $z_0$ coincide at $t_0=0$ and $z_0=0$.

Figure 33:
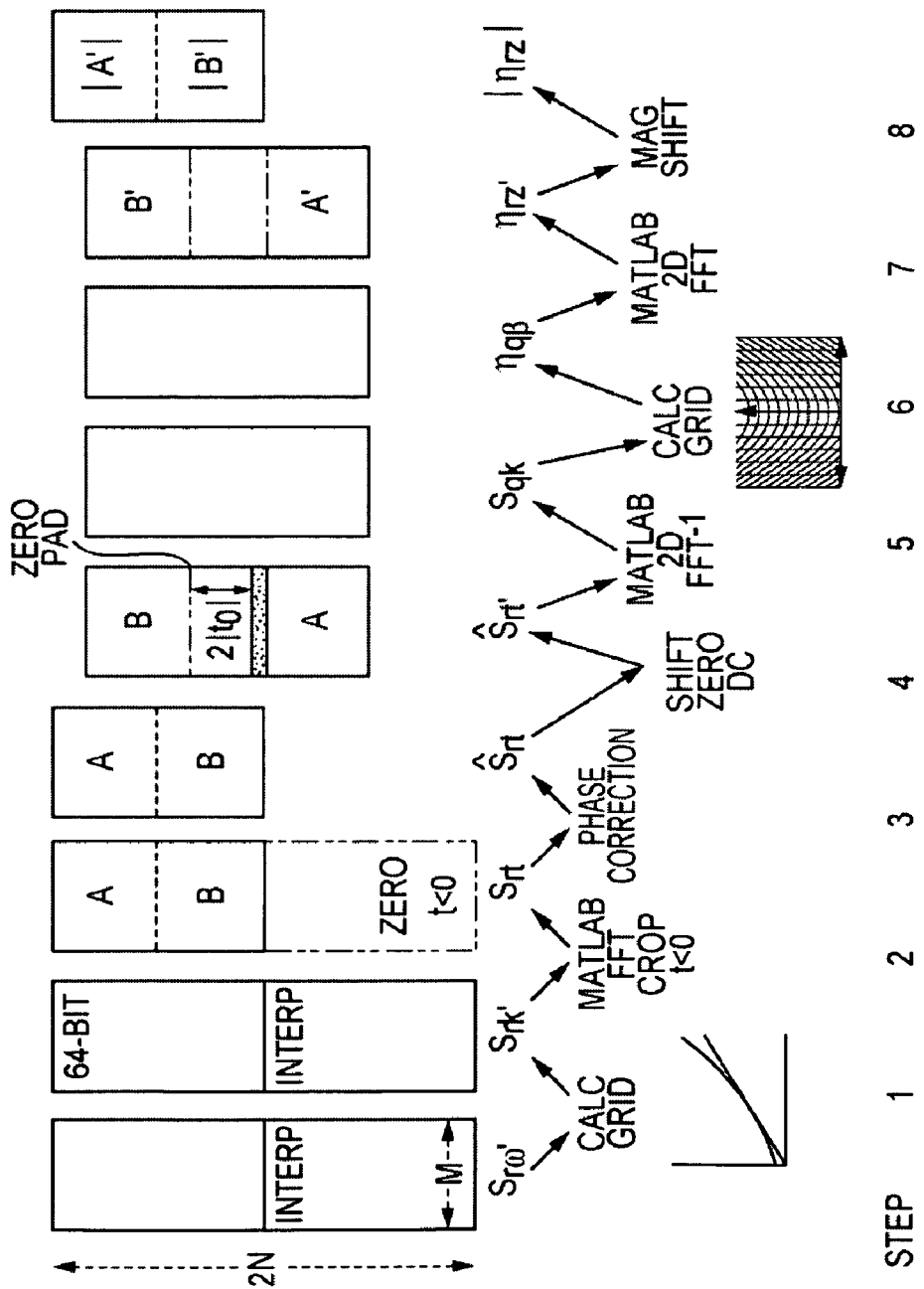
FIG. 33 is a data flow chart for ISAM processing, in accordance with embodiments of the present invention.

FIG. 33 shows a data flow diagram for the prototype ISAM algorithm for 2D imaging where in the paraxial limit $r\parallel$ now describes a single transverse dimension. It is noted that the other transverse dimension may be solved separately in so much as the paraxial approximation holds. The prototype algorithm was designed in Matlab, a mathematical software package, where all the calculations were done in double precision, 64-bit. The digitized spectra S$r\omega$ is a function of the M discrete positions r in the plane perpendicular to the beam axis and the N discrete frequencies $\omega$. A non-uniform interpolation is needed to map the sampled frequencies $\omega$ to the sampled wavenumbers k. Similarly, the ISAM solution requires a non-uniform interpolation mapping wavenumbers k to longitudinal frequency coordinates of the object $\beta$. The cubic B-spline is chosen as the non-uniform resampling interpolator; although, a windowed sinc interpolator, such as the prolate-spheroidal interpolator, may be chosen to select specific convergence characteristics. Unfortunately, the frequency response for many non-uniform interpolation procedures drops in performance for frequencies higher than half the Nyquist rate. To mitigate this effect, each spectrum is interpolated by performing a fast Fourier transform (FFT), padding with N zeros, and performing an inverse FFT (IFFT). The interpolated spectra are stored in a buffer with 2N rows and M columns. Thus, the new interpolated, digitized spectra S$r\omega$' is a function of the sampled positions r and the new sampled frequencies $\omega$'. Similarly, S$rk$ is interpolated by a factor of 2 to get S$rk$' as a function of r and the new uniformly sampled wavenumbers k'.

The non-uniformly sampled spectrum in spectral-domain OCT can be corrected in a fashion similar to material dispersion correction by resampling the Fourier spectrum from $\omega$' to k. A desired reindexing array in is based primarily on calibrated, second- and third-order correction factors $\alpha_2$ and $\alpha_3$, respectively.

$$i_n = 2n + \alpha_2 \left(\frac{2n}{N} - \omega_{ctr}\right)^2 + \alpha_3 \left(\frac{2n}{N} - \omega_{ctr}\right)^3, \quad (73)$$

where n is an integer between 0 and N−1, 2N is the number of samples of the interpolated spectrum $S_{r\omega'}$, and $\omega_{ctr}$ is the calculated centroid of the spectrum on a scale from 0 to 1. $\alpha_2$ and $\alpha_3$ are set through a calibration routine. A mirror models a perfect reflector with a minimized width of the point spread function (PSF). Thus, $\alpha_2$ and $\alpha_3$ are adjusted such that the imaged PSF is indeed minimized.

FIG. 33 shows a data flow chart of the prototype algorithm which has been broken down into the eight steps listed below.

Step 1 The spline coefficients and interpolations are computed as described above. The result is stored in an array $S_{rk'}$ where k' is the uniformly sampled wavenumber.

Step 2 The 1-D FFT of the columns of $S_{rk'}$ is taken to get the signal $S_{rt}$ where t is the sampled time delay of the optical signal. The Hermitian symmetric values, where t<0, are removed. There will be no ambiguity, if the reference arm is placed such that the reference light pulse arrives at the spectrometer before the sample light pulses. The complex analytic OCT signal is represented by $S_{rt}$.

Step 3 A phase correction procedure is implemented to ensure phase stability for the ISAM reconstruction. A glass coverslip can be placed on top of the sample to track and reduce system instabilities. The phase corrected signal is represented as $\hat{S}_{rt}$.

Step 4 The contribution of the constant spectral intensity is removed by setting $\hat{S}_{rt}$ to zero, for values near t=0. Then, a coordinate change from t to t' is made by circularly shifting the rows such that the focal plane lies at t'=0, which coincides with z'=0 where the solution is derived in equation (72). The data $\hat{S}_{rt'}$ is padded with 2|t$_0$| rows of zeros to prevent aliasing of the shifted data, where t$_0$ is the number of time delay samples from the focus to the center of $\hat{S}_{rt}$.

Step 5 The 2-D IFFT of $\hat{S}_{rt'}$ is taken to get $S_{qk}$.

Step 6 The 2-D ISAM resampling grid, spline coefficients, and the interpolations are calculated. Then the result is multiplied by $\tilde{\tilde{B}}(Q,k)e^{i\pi/2}$ to get $\eta_{q\beta}$.

Step 7 The 2-D FFT of $\eta_{q\beta}$ is taken to get $\eta_{rz'}$, where z'=0 at the focal plane.

Step 8 A coordinate change from z' to z is made by circularly shifting the rows such that the reference delay lies at the top of the image and corresponds to the z=0 plane. Then, the magnitude of the ISAM reconstruction $\eta_{rz}$ is calculated resulting in ISAM amplitude image $|\eta_{rz}|$.

There are a number of operations hindering the performance of the prototype ISAM algorithm. Using C++ instead of Matlab allows for a number of speed improvements. The 64-bit operations such as the FFT and interpolations can be replaced with 32-bit operations with a small, but tolerable, increase of quantization noise. A speed advantage is gained by replacing the 'for' loops within Matlab scripts by vectorized Intel SSE (Streaming SIMD Extentions) commands and/or compiled 'for' loops. Time-expensive, built-in Matlab interpolation and FFT functions are replaced with hardware optimized functions as found in the Intel Math Kernel Library (MKL). An FFT of the real spectrum is implemented using the customized real-to-complex FFT in the MKL. The resampling step corrects the depth dependent defocus and is crucial for the performance of the algorithm. Although, the filter in equation (72), $\tilde{\tilde{B}}(Q,k)e^{i\pi/2}$, can be highly singular which introduces noise, hence the need for regularization. Furthermore, applying the filter provides a quantitative, but not a significant qualitative change to the data. Thus, equation (72) is reduced to an unfiltered solution $$\tilde{\tilde{\eta}}^{+''}(Q,\beta) = \tilde{\tilde{S}}(Q,k)\Big|_{k=\frac{1}{2}\sqrt{\beta^2+Q^2}} \quad (74)$$

without degradation of the Fourier space resampling. The focal plane is fixed such that t$_0$=0 by imposing a restriction that the focus be placed at the center of the image. Therefore, the complex analytic signal does not need to be padded with any zeros, and thus the computation time of the FFT is reduced because the FFT is always a power of two. While the prototype functions utilized dynamically allocated memory, the real-time program allocates memory prior to imaging time. Similarly, a table of resampling coefficients for the dispersion compensation and the ISAM reconstruction are pre-calculated and stored in memory. The prototype algorithm interpolated the data by two to mitigate the high frequency roll-off of the non-uniform interpolator. Although the interpolation has good frequency response, it is not necessary, especially when speed is an issue. The phase stabilization procedures, which might be needed for long acquisition periods, are not necessary for 2-D imaging since this SD-OCT system provides good phase stability over the short duration of the scan, about 17 ms.

The key computation for ISAM is the resampling in the Fourier space. The new design is an efficient routine which requires two interpolations of the columns, one one-dimensional (1D) real-to-complex (R2C) fast Fourier transform (FFT) of the columns, and two 2D FFTs. The FFT routine from the Intel Math Kernel Library (MKL) was used for all 1D and 2D transforms. The 1D 2048-point R2C FFT is calculated for every column of the 512×2048 real-valued data, while the 2D FFT and 2D IFFT are calculated for the 512×1024 complex values.

The reindexing array in and the corresponding cubic B-spline interpolation table is pre-computed and stored in random access memory (RAM) for repeated use. The coefficients for the cubic B-spline are pre-computed. The integer part of the index used for calculation of the in the cubic B-spline is given by $$a_x[n] = \begin{cases} \lfloor i_n \rfloor + x, & 0 \le \lfloor i_n \rfloor + x \le N - 1 \\ 0, & \lfloor i_n \rfloor + x < 0 \\ N - 1, & \lfloor i_n \rfloor + x > N - 1, \end{cases} \quad (75)$$

$$x = -1, 0, 1, 2 \text{ and } 0 \le n < N$$

The fractional coefficients are given by $$f_n = i_n - \lfloor i_n \rfloor, 0 \le n < N \quad (76)$$

and $$b_{-1}[n] = (1-f_n)^3/6$$

$$b_0[n] = (4 - 6f_n^2 + 3f_n^3)/6$$

$$b_1[n] = (1 + 3f_n + 3f_n^2 - 3f_n^3)/6$$

$$b_2[n] = f_n^3/6, 0 \le n < N \quad (77)$$

Next, the Fourier resampling indices of ISAM are pre-calculated. The constants which specify the axial and transverse bandwidths of the object, based on system parameters, are $\beta_{min}$, $\beta_{max}$, $q_{min}$, and $q_{max}$, respectively. These constants are selected in accordance to the specific bandwidth parameters of the system and describe the boundaries of the Fourier space shown in FIG. 32(*c*). By defining the longitudinal bandwidth parameters of the object rather than the wavenumber, we can avoid computationally costly zeropadding of the resampled solution. However, a small loss of spectral information across the $\beta_{min}$ boundary may reduce the signal-to-noise ratio, but only marginally. In this case, $\beta_{min}$ and $\beta_{max}$ are set to be the boundaries of the optical bandwidth, $q_{min}$ is set to zero, and $q_{max}$ is set to the maximum transverse scanning frequency. More important than the exact values for, $\beta_{min}$, $\beta_{max}$, $q_{min}$, and $q_{max}$, is the ratio of the corresponding transverse and longitudinal bandwidths. The maximum and minimum wavenumber are calculated for the region of interest, $$k_{min} = \beta_{min}/2, \quad (78)$$

$$k_{max} = 0.5\sqrt{\beta_{max}^2 + q_{max}^2}. \quad (79)$$

A range of values for q[m] and β[n] is created in the 2-D Fourier space and the resampling grid kq[m,n] is pre-calculated. Notice here that M and N'=N/2 are assigned according to number of rows and columns in the complex analytic sampled Fourier data.

$$q[m] = \begin{cases} m\dfrac{2q_{max}}{M}, & 0 < m \le \dfrac{M}{2} \\ (m - M)\dfrac{2q_{max}}{M}, & M/2 < m \le M, \end{cases} \quad (80)$$

$$\beta[n] = \dfrac{n(\beta_{max} - \beta_{min})}{N'} + \beta_{min}, \, 0 \le n < N', \quad (81)$$

$$kq[m, n] = \dfrac{N'}{k_{max} - k_{min}}\left(0.5\sqrt{\beta[n]^2 + q[m]^2} - k_{min}\right) + 1, \quad (82)$$

$$0 \le n < N', \, 0 \le m < M$$

Figure 32C:
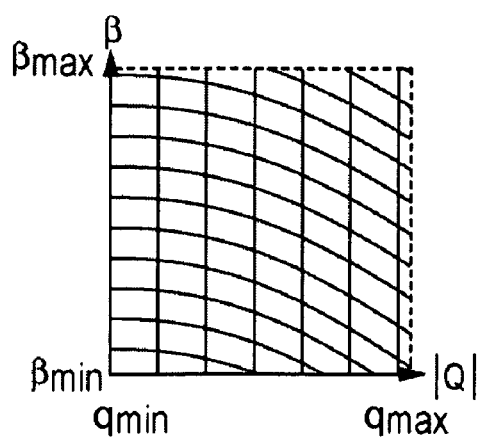

The kq[m,n] grid is used to calculate a table of values for the cubic B-spline coefficients. The values are calculated as shown above except each column of resampling parameters is different and therefore must also be saved. FIG. 32(*b*) shows the plot of the kq[m,n] grid where the curved lines represent the constant values of β[n]. This 2D grid is used to calculate another table of cubic B-spline coefficients. The spline values are calculated as shown above except each column of the resampling parameters is different and therefore 2D spline coefficients are stored in memory.

Similar to the spline coefficient calculations shown above, the reindexing array kq[m,n] and the corresponding cubic B-spline interpolation coefficient table is pre-computed and stored in random access memory (RAM) for repeated use. The integer part of the index used for calculation of the in the cubic B-spline is given by $$a'_{q,x}[m, n] = \begin{cases} \lfloor kq[m, n] \rfloor + x, & 0 \le \lfloor kq[m, n] \rfloor + x \le N' - 1 \\ 0, & \lfloor kq[m, n] \rfloor + x < 0 \\ N' - 1, & \lfloor kq[m, n] \rfloor + x > N' - 1; \end{cases} \quad (83)$$

$$x = -1, 0, 1, 2;$$

$$0 \le n < N'; \, 0 \le m < M$$

The fractional coefficients are given by $$f_{m,n} = kq[m,n] - \lfloor kq[m,n] \rfloor, 0 \le n < N'; 0 \le m < M \quad (84)$$

and $$b'_{q,-1}[m,n] = (1 - f_{m,n})^3/6$$

$$b'_{q,0}[m,n] = (4 - 6f_{m,n}^2 + 3f_{m,n}^3)/6$$

$$b'_{q,1}[m,n] = (1 + 3f_{m,n} + 3f_{m,n}^2 - 3f_{m,n}^3)/6$$

$$b'_{q,2}[m,n] = f_{m,n}^3/6, 0 \le n < N'; 0 \le m < M \quad (85)$$

Figure 34:
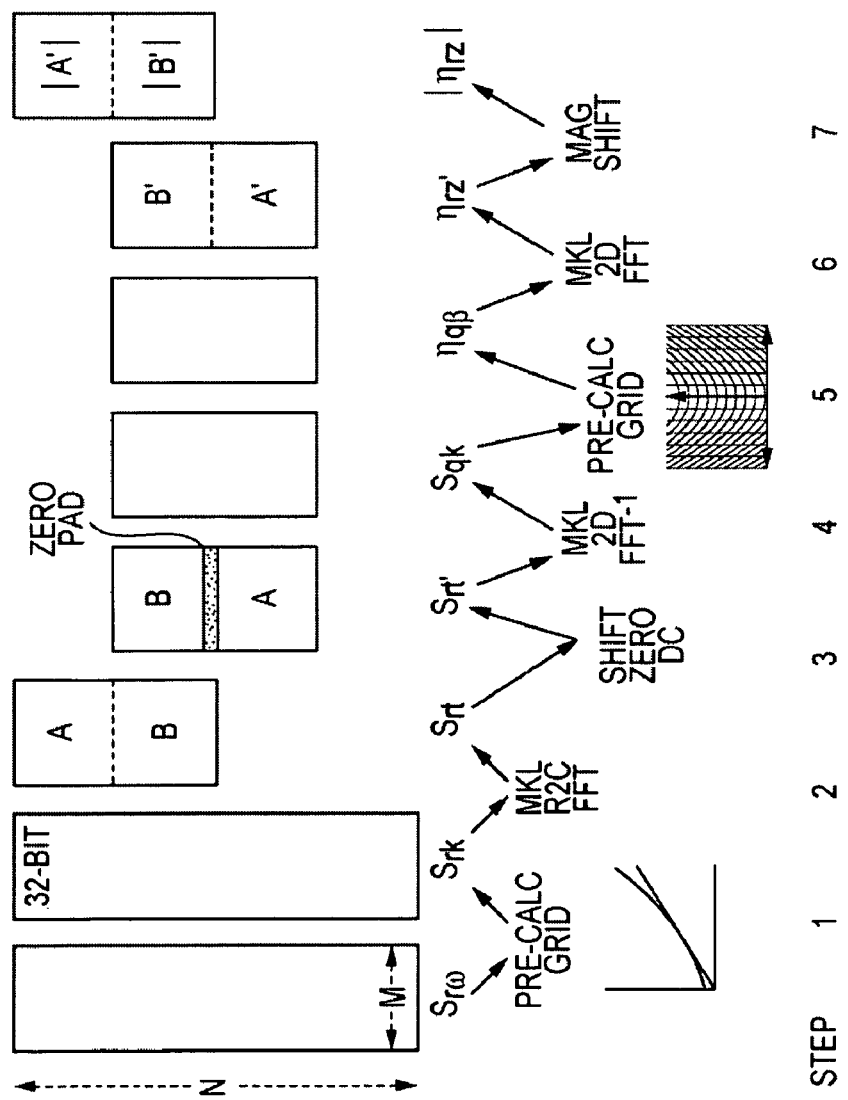
FIG. 34 is a computational flow chart for memory allocation for successive steps of ISAM processing, in accordance with embodiments of the present invention.

Using the pre-calculated tables, a flow diagram of the real-time algorithm is shown in FIG. 34.

Here $S_{r\omega}[m,n]$ is the raw interferometric data captured from the camera and has M columns and N rows. In this implementation, M=512 columns and N=2048 rows.

Step 1 The pre-calculated table is used to perform the interpolation as follows.

$$S_{rk}[m, n] = S_{r\omega}[m, a_{-1}\{n\}]b_{-1}\{n\} + \quad (86)$$

$$S_{r\omega}[m, a_0\{n\}]b_0\{n\} + S_{r\omega}[m, a_1\{n\}]b_1\{n\} + S_{r\omega}[m, a_2\{n\}]b_2\{n\},$$

for all integers $0 \le n < N$ and $0 \le m < M$.

Step 2 The real-to-complex 1-D FFT routine from the Intel Math Kernel Library (MKL) is used on all the columns.

$$S_{rt}[m, n] = \sum_{k=0}^{N-1} S_{rk}[m, k]e^{-\frac{2\pi i}{N}kn}, \quad (87)$$

$$0 \le n < N \text{ and } 0 \le m < M$$

The real-to-complex FFT will compute N/2 complex values. The new number of rows of the complex data is given by N'=N/2.

Step 3 The contribution of the noise from the average spectral intensity on the detector is removed by setting $S_{rt}[m,n]$ equal to zero at the t=0 plane. Also, $S_{rt'}[m,n]$ is circularly shifted by half such that the focus will be the new t'=0 plane.

$$S_{rt'}[m, n] = \begin{cases} S_{rt}\left[m, n + \frac{N'}{2}\right] & 0 \le n < \frac{N'}{2} \\ 0 & \frac{N'}{2} \le n < \frac{N'}{2} + 2 \\ S_{rt}\left[m, n - \frac{N'}{2}\right] & \frac{N'}{2} + 2 \le n < N' \end{cases} \quad (88)$$

and $0 \le m < M$.

Step 4 The complex 2-D inverse FFT (IFFT) of the complex analytic signal $S_{rt'}[m,n]$ is calculated $$S_{qk}[m, n] = \frac{1}{MN'} \sum_{r=0}^{M-1} \sum_{t=0}^{N'-1} S_{rt'}[r, t] e^{\frac{2\pi i}{N'} nt} e^{\frac{2\pi i}{M} mr}, \quad (89)$$

$0 \le n < N'$ and $0 \le m < M$.

Step 5 The pre-calculated table is used to perform the cubic B-spline interpolation as follows.

$$\eta_{q\beta}[m, n] = \quad (90)$$
$$S_{qk}[m, a'_{q,-1}\{m, n\}]b'_{q,-1}\{m, n\} + S_{qk}[m, a'_{q,0}\{m, n\}]b'_{q,0}\{m, n\} +$$
$$S_{qk}[m, a'_{q,1}\{m, n\}]b'_{q,1}\{m, n\} + S_{qk}[m, a'_{q,2}\{m, n\}]b'_{q,2}\{m, n\},$$
$0 \le n < N'$ and $0 \le m < M$, where the calculated cubic B-spline coefficients are from the lookup table.

Step 6 The complex 2-D FFT of the Fourier transformed object $\eta_{q\beta}[m,n]$ is calculated $$\eta_{rz'}[m, n] = \sum_{q=0}^{M-1} \sum_{\beta=0}^{N'-1} \eta_{q\beta}[q, \beta] e^{-\frac{2\pi i}{N'} \beta n} e^{-\frac{2\pi i}{M} qm}, \quad (91)$$

$0 \le n < N'$ and $0 \le m < M$.

Step 7 $\eta_{rz'}[m,n]$ is circularly shifted such that the focus is in the middle of the image, $$\eta_{rz}[m, n] = \begin{cases} \eta_{rz'}\left[m, n + \frac{N'}{2}\right] & 0 \le n < \frac{N'}{2} \\ \eta_{rz'}\left[m, n - \frac{N'}{2}\right] & \frac{N'}{2} \le n < N', \end{cases} \quad (92)$$

then the magnitude $|\eta_{rz}[m,n]|$ is displayed.

In various embodiments of the present invention, the disclosed methods determining the three-dimensional susceptibility of a sample may be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A method of forming an image of ear tissue, comprising:
   non-invasively inserting a fiber-based device into a patient's ear canal;
   illuminating the ear tissue at a focal region of a broadband optical signal;
   acquiring OCT data from the ear tissue, from a region extending beyond the focal region, while the fiber-based device is in the ear canal; and
   converting the OCT data into at least one image.

2. The method of claim 1 further comprising performing further data analysis on the image while the fiber-based device is in the ear canal.

3. The method of claim 2, wherein the further data analysis includes enhancing the image.

4. The method of claim 2, wherein the further data analysis includes classifying the ear tissue imaged using the OCT data.

5. The method of claim 4, wherein the OCT data is run through classification algorithms so as to classify the ear tissue imaged.

6. The method of claim 5, wherein the classification algorithms analyze the OCT data and classify the ear tissue imaged using an optical property which is derived from the OCT data.

7. The method of claim 6, wherein the optical property is one of a refractive index, a scattering profile, a scattering coefficient, an anisotropy factor, birefringence, a spectral shift, texture, a Doppler shift, a phase resolution, a phase-resolved Doppler measurement, a phase-resolved spectroscopic measurement, a light scattering parameter, and spectroscopic absorption.

8. The method of claim 1, wherein the fiber-based device is coupled to an otoscope.

9. The method of claim 1, wherein the ear tissue includes a biofilm.

10. A system for imaging ear tissue in real-time comprising:
- a core imaging unit which generates a low-coherence broadband optical signal; and
- a fiber-based device connected with an otoscope, wherein the fiber-based device is in communication with and receives the low-coherence broadband optical signal from the core imaging unit, illuminates ear tissue at a focal region and transmits scattered light from the ear tissue back to the core imaging unit for generating an interferometry signal; and
- a processor for receiving the interferometry signal and for generating therefrom an image of the ear tissue from a region extending beyond the focal region.

11. The system of claim 10, further comprising a core software unit which receives the interferometry signal OCT data and performs further data analysis on the interferometry signal.

12. The system of claim 11, wherein the further data analysis includes enhancing the image of the ear tissue.

13. The system of claim 10, wherein the core software unit includes classification algorithms.

14. The system of claim 13, wherein the classification algorithms analyze the interferometry signal and classify tissue imaged using an optical property which is derived from the interferometry signal.

15. The system of claim 10, wherein the otoscope is a pneumatic otoscope which comprises an ear speculum connected with a head unit.

16. The system of claim 14, wherein the fiber-based device is positioned to receive light which enters the ear speculum.

17. The system of claim 10, wherein the core imaging unit is integrated with the otoscope.

18. A method of analyzing ear tissue comprising:
- beginning a non-invasive procedure on a patient exposing middle ear tissue;
- illuminating the ear tissue at a focal region of a broadband optical signal; and
- acquiring OCT data from a region of the middle ear tissue extending beyond the focal region.

19. The method of claim 18, further comprising: analyzing the OCT data; and
- classifying the ear tissue upon analyzing the full-field OCT data.

20. The method of claim 18 further comprising upon classifying the ear tissue, indicating to a user the type of ear tissue classified.

21. The method of claim 18 further comprising ending the non-invasive procedure after the classifying of the ear tissue.

22. The method of claim 18, wherein the ear tissue is living.

23. A method of examining a patient's ear, comprising:
- illuminating the ear tissue at a focal region of a broadband optical signal.
- non-invasively acquiring OCT data from a region of the patient's middle ear extending beyond the focal region; and
- analyzing the OCT data for the presence of a biofilm in the patient's middle ear.

24. The method of claim 23, further comprising indicating to a user the presence or absence of the biofilm.

25. A method of examining a patient's ear, comprising:
- illuminating the ear tissue at a focal region of a broadband optical signal;
- non-invasively acquiring OCT data from a region of the patient's middle ear extending beyond the focal region; and
- analyzing the OCT data for the patient's middle ear condition.

26. The method of claim 25, wherein the analyzing of the data comprises analyzing the data for the patient's tympanic membrane condition.

27. The method of claim 25, wherein the analyzing of the OCT data comprises forming an image of at least a portion of the patient's middle ear.

28. An apparatus for examining a patient's ear, comprising:
- (a) a core imaging unit for illuminating tissue at a focal region and acquiring OCT data of from a region extending beyond the focal region, and
- (b) a fiber-based device, adapted for selecting as the tissue the patient's middle ear, connected to the core imaging unit.

29. The apparatus of claim 28, wherein the fiber-based device is adapted for insertion into the patient's ear canal.

30. The apparatus of claim 28, further comprising an indicator used to indicate to a user a type of tissue which has been imaged.

* * * * *

UNITED STATES PATENT AND TRADEMARK OFFICE
CERTIFICATE OF CORRECTION

PATENT NO.      : 8,115,934 B2
APPLICATION NO. : 12/040539
DATED           : February 14, 2012
INVENTOR(S)     : Boppart et al.

It is certified that error appears in the above-identified patent and that said Letters Patent is hereby corrected as shown below:

In column 59, lines 16-17
Replace "signal OCT data and"
With "signal and"

In column 60, line 33
Replace "OCT data of from"
With "OCT data from"

Signed and Sealed this
Twenty-ninth Day of May, 2012

David J. Kappos
*Director of the United States Patent and Trademark Office*